(12) United States Patent
Carmel et al.

(10) Patent No.: US 12,194,221 B2
(45) Date of Patent: Jan. 14, 2025

(54) FILTER FOR REMOVAL OF MULTIPLE SCLEROSIS-ASSOCIATED T-CELLS

(71) Applicant: BIOIMMUNATE TECHNOLOGIES LTD., Jerusalem (IL)

(72) Inventors: Sigalit Carmel, Ramat Hasharon (IL); Shimon Shteingart, Tzur Hadassah (IL); Shlomo Yitzchaik, Jerusalem (IL); Hadar Amartely, Ma'ale Adumim (IL); Omri Shmuel Alfassy, Modi'in-Maccabim-Reut (IL); Elza Snir, Jerusalem (IL)

(73) Assignee: BIOIMMUNATE TECHNOLOGIES LTD., Jerusalem (IL)

(*) Notice: Subject to any disclaimer, the term of this patent is extended or adjusted under 35 U.S.C. 154(b) by 449 days.

(21) Appl. No.: 17/620,265

(22) PCT Filed: Jun. 26, 2020

(86) PCT No.: PCT/IB2020/000541
§ 371 (c)(1),
(2) Date: Dec. 17, 2021

(87) PCT Pub. No.: WO2020/260949
PCT Pub. Date: Dec. 30, 2020

(65) Prior Publication Data
US 2022/0347369 A1 Nov. 3, 2022

Related U.S. Application Data

(60) Provisional application No. 62/875,193, filed on Jul. 17, 2019, provisional application No. 62/867,594, filed on Jun. 27, 2019.

(51) Int. Cl.
*A61M 1/36* (2006.01)
*A61M 1/34* (2006.01)
*B01D 69/14* (2006.01)
*B01D 71/68* (2006.01)

(52) U.S. Cl.
CPC ........ *A61M 1/3687* (2013.01); *A61M 1/3496* (2013.01); *B01D 69/144* (2013.01); *B01D 71/68* (2013.01)

(58) Field of Classification Search
None
See application file for complete search history.

(56) References Cited

U.S. PATENT DOCUMENTS

| | | | |
|---|---|---|---|
| 5,595,881 A | 1/1997 | Kendrick et al. | |
| 2009/0304677 A1* | 12/2009 | Ichim | A61M 1/3679 424/529 |
| 2011/0262479 A1 | 10/2011 | Burrows et al. | |

FOREIGN PATENT DOCUMENTS

| | | | | |
|---|---|---|---|---|
| JP | 2018108103 A | * | 7/2018 | ......... B01D 15/3809 |
| WO | WO-2007103572 A2 | * | 9/2007 | ............ A61M 1/16 |

* cited by examiner

*Primary Examiner* — Krishnan S Menon
(74) *Attorney, Agent, or Firm* — The Roy Gross Law Firm, LLC; Roy Gross

(57) ABSTRACT

Biological filters for removing target components from biological fluids such as removal of pathogenic cells from whole blood, are described. The filters may include a medium comprising an inert surface, with capture material disposed on the inert surface. The filter may be configured to selectively recognize, capture, and remove target cells such as pathogenic cells associated with a disease, such as an autoimmune disease or cancer. Devices, systems, apparatuses, computer readable media, and methods associated with biological filtering are also provided.

21 Claims, 38 Drawing Sheets

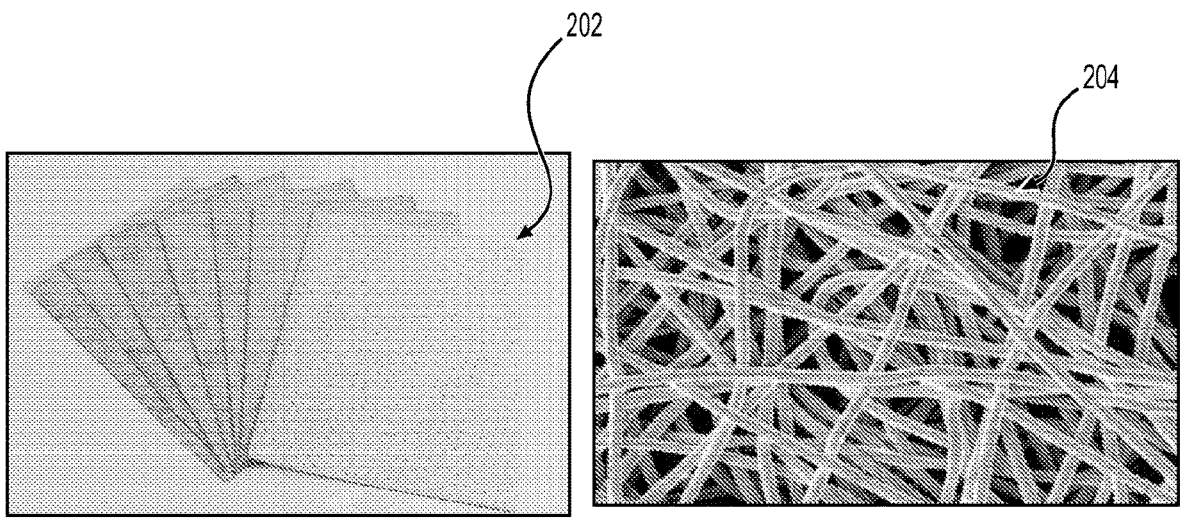
FIG. 2A
FIG. 2B
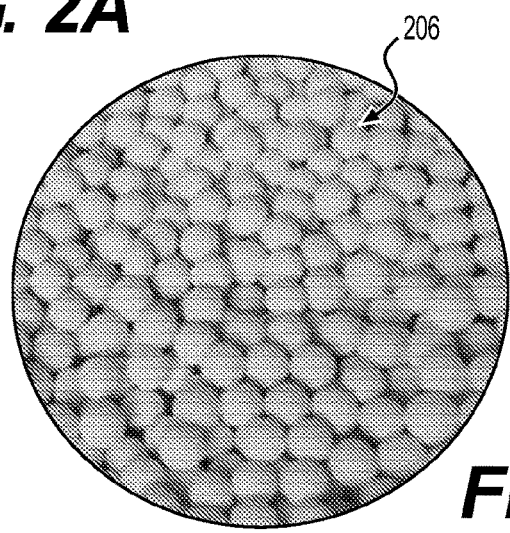
FIG. 2C
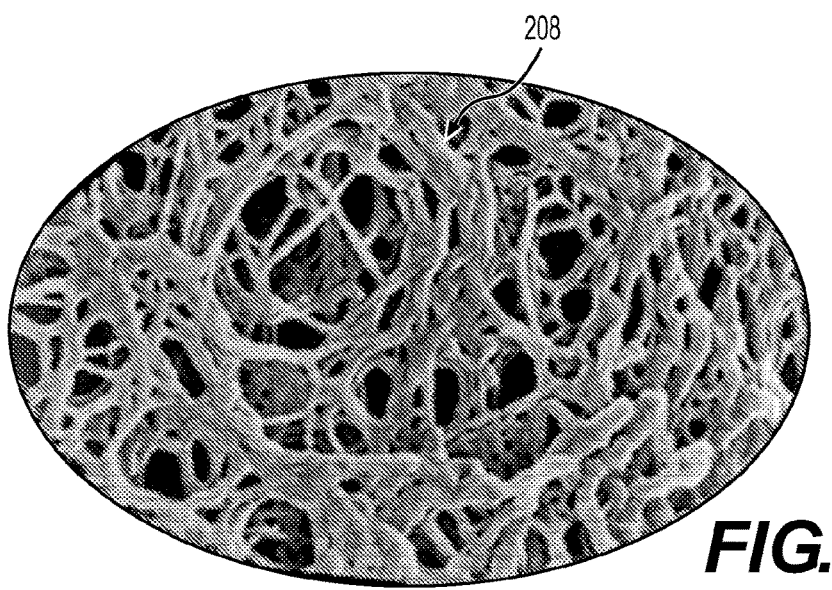
FIG. 2D

DEMYELINATION MECHANISMS

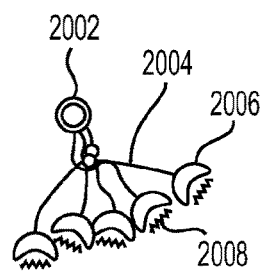
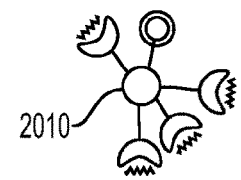
FIG. 20A     FIG. 20B
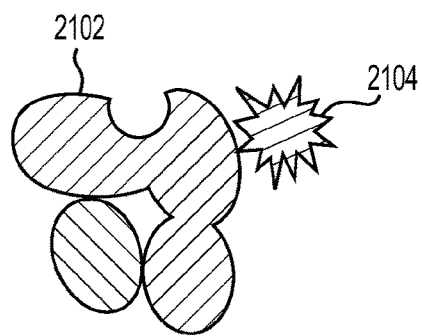
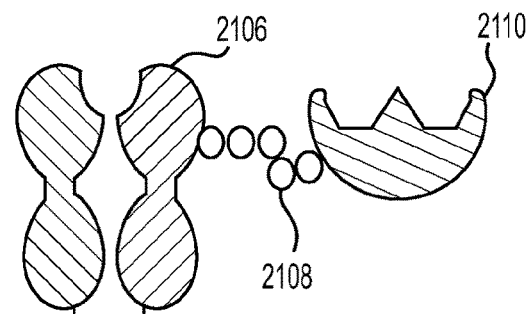
FIG. 21A     FIG. 21B

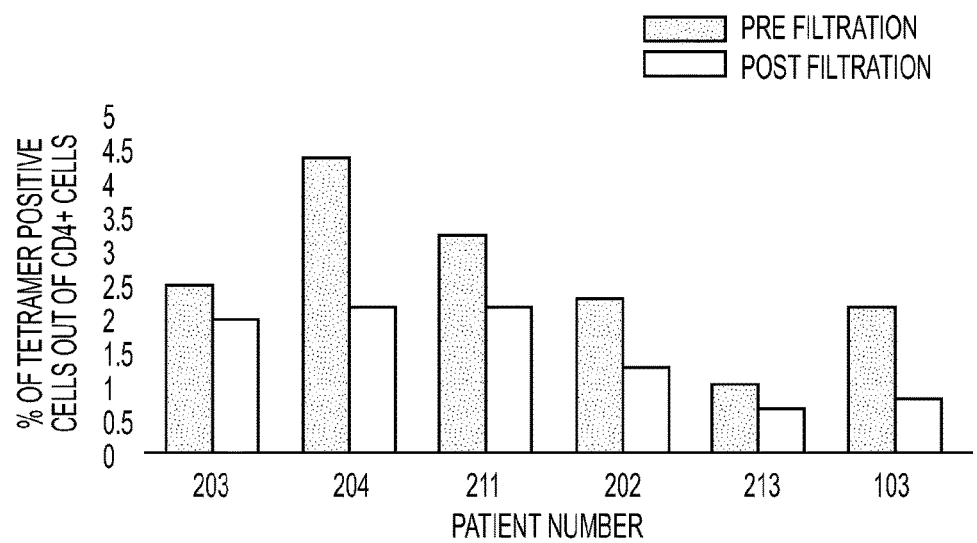
FIG. 36
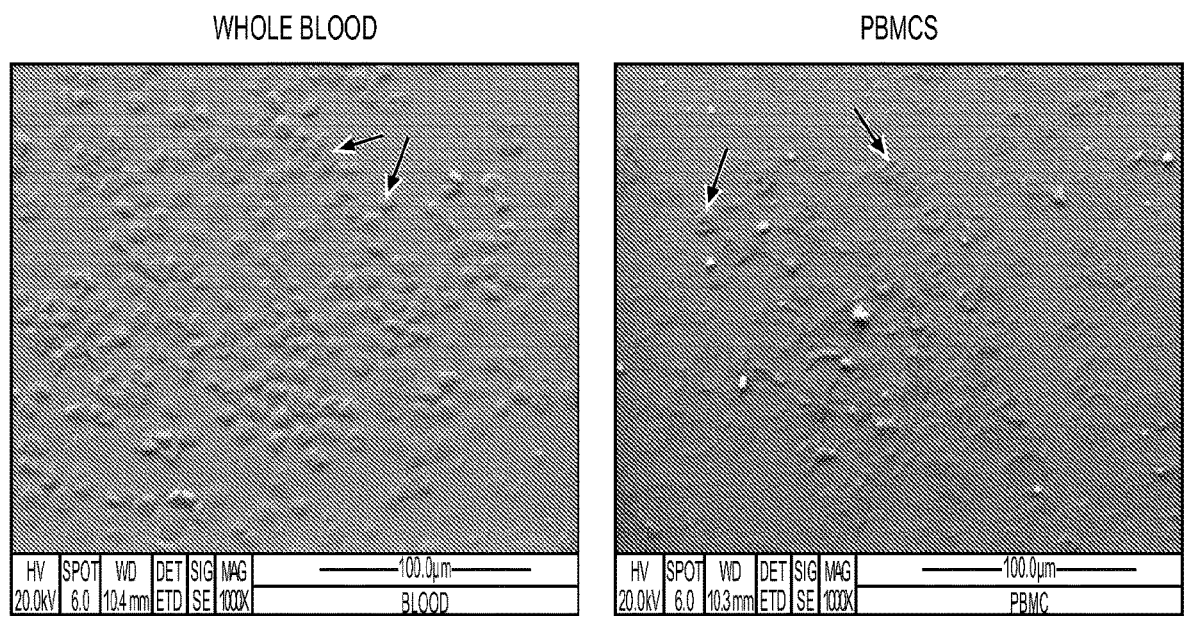
FIG. 37A  FIG. 37B

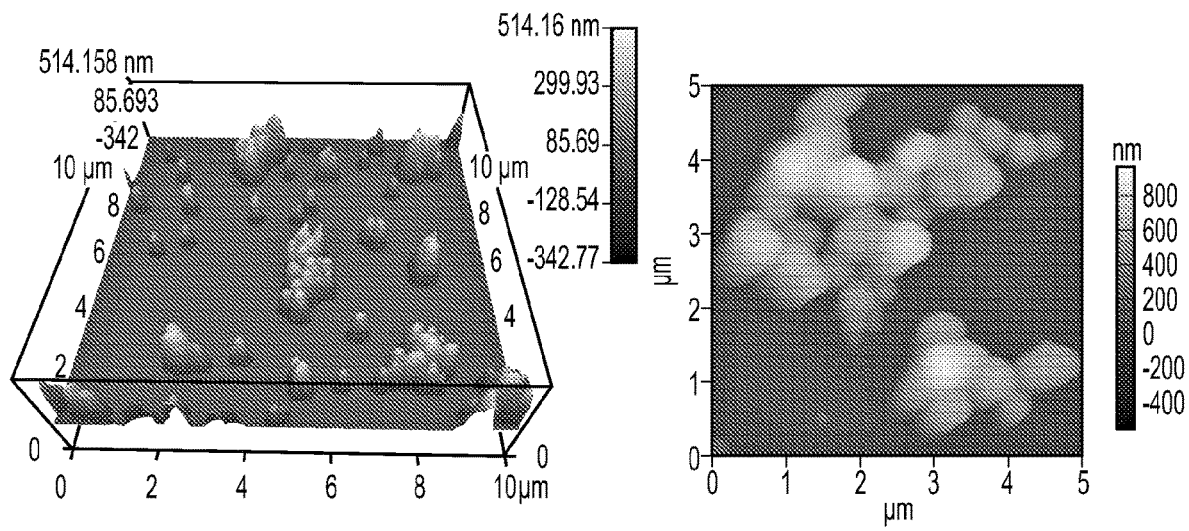
FIG. 41A  FIG. 41B
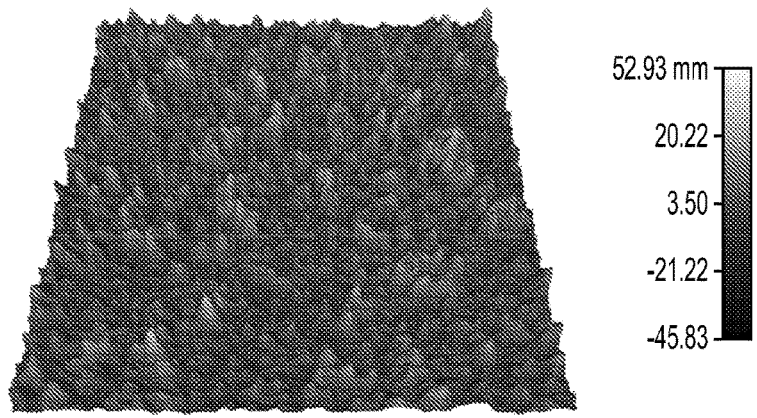
FIG. 42A
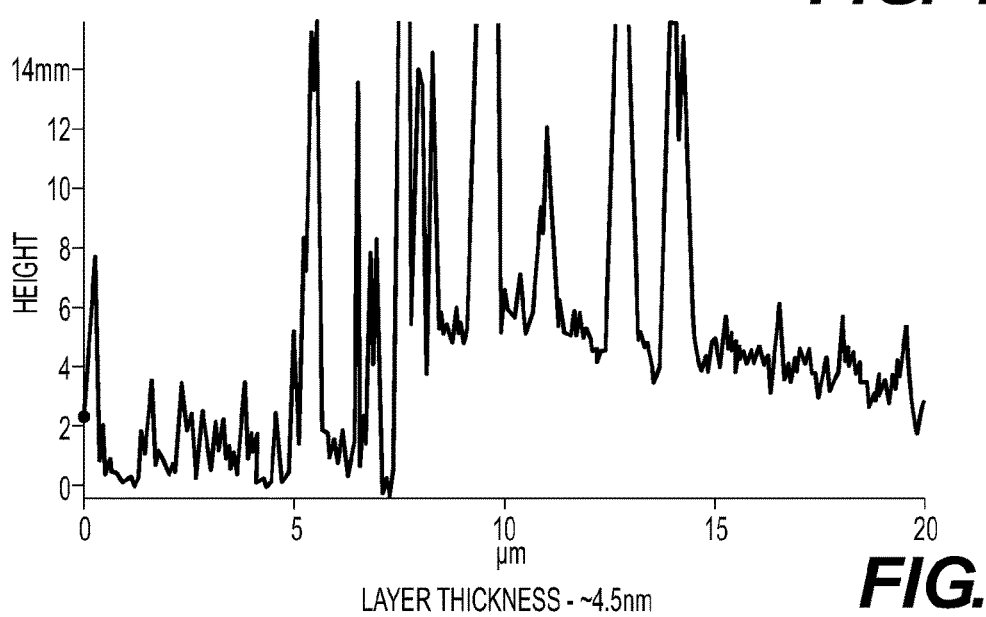
LAYER THICKNESS - ~4.5nm
FIG. 42B

FILTER FOR REMOVAL OF MULTIPLE SCLEROSIS-ASSOCIATED T-CELLS

CROSS-REFERENCE TO RELATED APPLICATIONS

This application is a national stage filing under 35 U.S.C. § 371 of International Application No. PCT/IB2020/000541 filed Jun. 26, 2020, and designating the U.S., which claims priority to U.S. Provisional Patent Application No. 62/867,594, filed Jun. 27, 2019, and U.S. Provisional Patent Application No. 62/875,193, filed Jul. 17, 2019, the entire content of each of which is incorporated herein by reference.

TECHNICAL FIELD

This disclosure relates generally to devices, systems, and methods for removing components of biological fluids. In some applications, the devices, systems, and methods may be used for the treatment of diseases such as but not limited to autoimmune diseases, cancers, other immune system related disorders or conditions, and complications related to transplantation. More particularly, aspects of this disclosure relate to devices, systems, and methods for treating diseases by modifying the cell composition of a patient's blood.

BACKGROUND

Autoimmune diseases are diseases where the immune system identifies self-antigens as foreign, thus attacking the body. This may occur in a wide spectrum of diseases, ranging from organ specific (e.g. thyroid or pancreas) to systemic diseases (e.g. Systemic lupus erythematosus). Current treatments for autoimmune diseases are focused on a global and general immunosuppression that may entail significant side effects and may causing a patient to be more prone to infectious diseases.

Multiple sclerosis (MS) is one example of a chronic progressive autoimmune disease that attacks myelinated axons in the central nervous system (CNS) to various degrees thus causing significant gradual physical disability. MS interferes with a patient's quality of life and indeed approximately 30% of the patients with MS will end up in a wheelchair or will experience other severe disabilities. There are about three million individuals worldwide with MS. In the U.S. alone, nearly 10,000 new cases of MS are diagnosed each year, resulting in a growing economic and social burden. In most patients, the disease begins as an episodic disorder and evolves over time into a progressive one. There are four main patterns of the disease. Clinically Isolated Syndrome (CIS) is a first episode of neurological symptoms that lasts for at least 24 hours. Although some people never go on to experience further neurological symptoms, in others CIS can be the first sign of what may later turn out to be multiple sclerosis. Another MS pattern is referred to as relapsing remitting MS (RRMS) characterized by acute attacks following remission in which the disease does not progress. When this form becomes progressive, it is called Secondary Progressive MS (SPMS). Primary Progressive MS (PPMS) is progressive from the start.

Current MS treatments are primarily pharmacological. These remedies tend to be accompanied by toxic effects, global immune-suppression, and various side effects such as: rash, flu like symptoms, fever, chills, cough, chest pain, abdominal pain, diarrhea, flushing, nausea, pneumonia, progressive multiple leukoencephalopathy (PML 1:1000), headache, depression, bradycardia, lymphopenia, bronchitis, diarrhea, back pains, severe headache, hypertension, transient bradycardia, immunodepression, pruritis, impaired renal function, increase in liver enzymes, ACS, sarcoma (in animal model) and death. Pharmacological treatments only slightly reduce the frequency of attacks and do not typically stop disease progression permanently.

Approximately every three minutes another person in the U.S. is diagnosed with a blood or hematological cancer. Examples of hematological cancers include leukemias, lymphomas, myelomas, myelodysplastic syndromes (MDS), and myeloproliferative neoplasms (MPNs). New cases of leukemia, lymphoma and myeloma are estimated to account for 10 percent of newly diagnosed cancer cases in the US. Many forms of lymphomas and leukemias, including highly aggressive forms such as adult T-cell leukemia/lymphoma, are associated with neoplasms of white blood cells such as natural killer (NK) cells, T-cells and B-lymphocytes. Although in recent years immunoncology, which is the artificial stimulation of the immune system to fight cancer, has presented itself as an attractive and innovative alternative to traditional therapies such as surgery, radiation therapy and chemotherapy, this approach may not be able to reach its optimum potential in the treatment of cancers where the patient's immune cells are themselves cancerous.

In view of the foregoing, it is evident that there remains a need for alternative therapies of debilitating diseases such as autoimmune diseases and cancers.

SUMMARY OF A FEW ASPECTS OF THE DISCLOSURE

Some aspects of the present disclosure relate to biological filters. Consistent with disclosed embodiments, a biological filter may include: an inert surface medium; human leukocyte antigen (HLA) proteins disposed on the inert surface medium; antigen peptides bound to the HLA proteins on the inert surface medium; wherein the antigen peptides and the HLA proteins are selected to enable antigen-specific T-cell receptors to bind to a complex of the antigen peptides and the HLA-proteins when T-cells are brought into contact with the complex, thereby securing specific T-cells to the inert surface medium via the complex.

In another aspect, the present disclosure relates to a biological filter that may be configured for cytoreduction of multiple sclerosis-associated T-cells. The filter may include: a filter medium for hosting material that selectively binds antigen-specific T-cell receptors; and wherein the hosting material includes human leukocyte antigen (HLA)-myelin-peptide complexes selected to bind with myelin-specific T-cell receptors, to thereby enable specific binding of a population of T-cells that recognize the HLA-myelin peptide complexes.

In another aspect, the present disclosure relates to an apparatus that may be configured for removing pathogenic T-cells from a patient's blood. The apparatus may include: a first stage region being configured to retain a blood separator capable of separating white blood cells from other fractions of whole blood, the blood separator having an inlet, a white blood cell outlet, and a blood fraction outlet configured to enable return of the other fractions to the patient; a first pump for conveying blood from a patient through the first stage region; a second stage region configured to retain a biological filter including human leukocyte antigen (HLA)-peptide complexes and having at least one inlet and at least one outlet, and wherein the first stage region and the second stage region are oriented to enable flow from the white blood cell outlet of the blood separator to the at least one inlet of the biological filter; a second pump for recirculating white blood cells from the at least one outlet of the biological filter to the at least one inlet of the biological filter; a plurality of electrically controllable valves for directing blood through the first stage region and the second stage region; and at least one processor configured to: control the first pump to cause blood to flow through the first stage region until a quantity of white blood cells are separated and conveyed to the second stage region; deactivate the first pump when the quantity of white blood cells is separated and conveyed to the second stage region; activate the second pump and control a plurality of valves to recirculate the quantity of white blood cells through the biological filter for a sufficient time to separate the pathogenic T-cells from non-pathogenic white blood cells; and return the non-pathogenic white blood cells to the patient.

In another aspect, the present disclosure is directed to a tubing set that may be configured for use in removing pathogenic T-cells from a patient's blood. The tubing set may include: a first stage region including a blood separator for use in separating white blood cells from other fractions of whole blood and having an inlet, a white blood cell outlet, and a blood fraction outlet; a second stage region including a biological filter containing human leukocyte antigen (HLA)-peptide complexes and having at least one primary inlet, at least one primary outlet, at least one recirculation inlet, and at least one recirculation outlet; a recirculation loop interconnecting the at least one recirculation outlet with the recirculation inlet; at least one blood withdrawal tube for conveying blood from the patient to the at least one inlet of the first stage region; at least one intermediate tube for conveying blood from the white blood cell outlet of the first stage region to the primary inlet of the second stage region; at least one first stage bypass tube for conveying a blood fraction from the blood fraction outlet of the first stage region for return to the patient; and at least one white cell return tube for conveying white blood cells from the primary outlet of the second stage region for return to the patient.

In a further aspect, the present disclosure provides a system for predictively adjusting a treatment regimen for a patient with a T-cell associated immunological disease. The system may include: at least one processor, configured to: receive first data associated with treatment of a plurality of patients sharing a common HLA and common peptides triggering activation of disease-related T-cells, wherein the first data includes a progression of common peptides that activate the T-cells over time, in that at a later progression of a disease, a greater number of different peptides activates the disease-related T-cells than at an earlier time; receive second data associated with a specific patient with the common HLA and the common peptides and who is at a stage of the disease where a first set of peptides activates a first subpopulation of disease-related T-cells and a second set of peptides does not activate a second subpopulation of disease-related T-cells; determine using the first data that the second set of peptides in the specific patient corresponds to the later progression of the disease; and take remedial action to remove the second subpopulation of disease-related T-cells from the specific patient before the second set of peptides activates the second subpopulation of disease-related T-cells.

In another aspect, the present disclosure relates to a method of removing specific T-cells, pathogenic cells, or non-pathogenic cells from a patient. The method may include: drawing biological fluid from the patient, the biological fluid containing the specific cells; extracorporeally flowing the biological fluid through a medium hosting material that selectively binds to only the specific cells, to thereby trap the specific cells with the medium; and returning the biological fluid, absent the trapped specific cells, to the patient.

In yet another aspect, the present disclosure relates to a method for producing a personalized biological filter for selective removal of pathogenic cells from a patient. The method may include: determining a human leukocyte antigen (HLA) type of the patient; identifying at least one immunogenic peptide associated with a disease of the patient; recombinantly, synthetically, or endogenously producing HLA-peptide complexes corresponding to the determined HLA type of the patient and the at least one immunogenic peptide; and binding the HLA-peptide complexes to an inert surface medium of the biological filter. In another example, a method for producing a personalized biological filter for selective removal of pathogenic cells from a patient is contemplated, the method comprising: determining a human leukocyte antigen (HLA) type of the patient; identifying at least one immunogenic peptide associated with a disease of the patient; recombinantly or endogenously producing HLA proteins corresponding to the determined HLA type of the patient; binding the HLA proteins to an inert surface medium; synthesizing the at least one identified peptide associated with the disease of the patient; and loading the identified peptides on the HLA proteins bound to the inert surface medium.

In a further aspect, the present disclosure is directed to a method of treating a patient. The method may include: determining a human leukocyte antigen (HLA) type of the patient; determining specific disease-related peptides that together with the determined HLA, trigger T-cell receptor activation in the patient; extracorporeally expose blood of the patient to a filter treated with a complex constructed of the disease-related peptide loaded on the determined HLA, to thereby cause a binding of T-cells to the filter; and returning to the patient blood with the bound T-cells removed. In some embodiments, the method may be directed to treating autoimmune diseases in patients. For example, the method may be directed to treating a patient with a T-cell associated autoimmune disease, the method comprising: obtaining human leukocyte antigen (HLA)-peptide complex data for a particular patient having an autoimmune disorder triggered by first T-cells, and not triggered by second T-cells; comparing the HLA-peptide complex data of the specific patient with HLA-peptide complex data associated with a population of patients having T-cell associated pathology, wherein the populational data includes epitope spreading information suggesting that persons with autoimmune disorders triggered by the first T-cells, will progress over time to be triggered by the second T-cells; and before the autoimmune disorder of the particular patient is triggered by the second T-cells, remove the second T-cells from the particular patient.

In yet further aspect, the present disclosure relates to a method of estimating an amount of disease-specific pathogenic T-cells in a patient. The method may include: obtaining a first biological fluid sample from the patient; stripping native peptides from a first group of human leukocyte antigens (HLAs) in the first biological fluid sample; determining at least one sequence of the stripped native peptides; comparing the determined at least one sequence with historical information to identify at least one disease-specific peptide sequence among the native peptides; loading onto a second group of HLAs, a plurality of peptides sharing the at least one disease-specific peptide sequence to form a plurality of HLA-peptide complexes; bringing the plurality of HLA-peptide complexes into contact with a second biological fluid sample; determining, for the plurality of HLA-peptide complexes brought into contact with the second biological fluid sample, a quantity of T-cells that bind to the plurality of HLA-peptide complexes; and based on the determined quantity of T-cells that bind to of the plurality of HLA-peptide complexes, estimating the amount of disease-specific pathogenic T-cells in a biological fluid volume within the patient.

Additional features and advantages of the disclosed embodiments are set forth in part in the description that follows, and in part will be evident from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

FIG. 2A illustrates sheets of inert surface media consistent with embodiments of this disclosure.

FIG. 2B illustrates fibers of inert surface media consistent with embodiments of this disclosure.

FIG. 2C illustrates beads of inert surface media consistent with embodiments of this disclosure.

FIG. 2D illustrates a sponge-like structure of inert surface media consistent with embodiments of this disclosure.

FIG. 20B schematically illustrates an HLA tetramer, consistent with embodiments of this disclosure.

FIG. 21A schematically illustrates HLA I linked to a fluorophore, consistent with embodiments of this disclosure.

FIG. 21B schematically illustrates HLA II linked to an enzyme, consistent with embodiments of this disclosure.

FIG. 36 is a chart indicating that an exemplary filtration removed 42% of specific cells from PBMCs derived from MS patients, consistent with disclosed embodiments.

FIGS. 37A-37B illustrate a filter surface with captured cells, consistent with disclosed embodiments.

FIGS. 41A-42B illustrate atomic force microscopy (AFM) results of polysulfone-poly(2-aminoethyl) acrylamide membrane films alone (FIG. 41A) and coated with protein (FIG. 41B), consistent with disclosed embodiments.

FIGS. 42A-42B illustrate atomic force microscopy (AFM) results of protein activated silicon sheets, consistent with disclosed embodiments.

DETAILED DESCRIPTION

Figure 1:
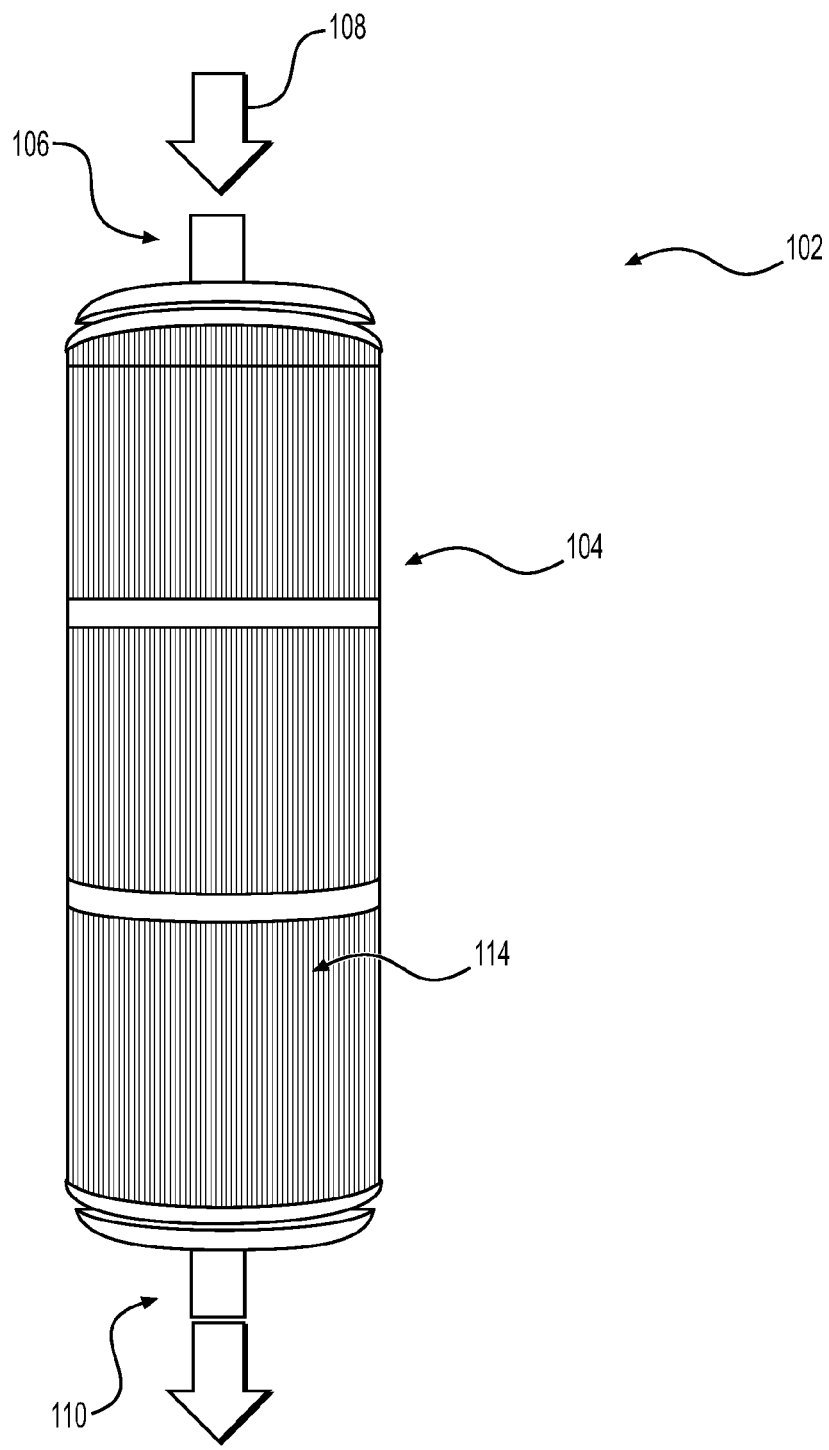
FIG. 1 illustrates an exemplary biological filter assembly consistent with embodiments of this disclosure.

Exemplary embodiments are described with reference to the accompanying drawings. Where convenient, the same reference numbers are used throughout the drawings to refer to the same or like parts. As an aid to the reader, this detailed description includes a series of topical headings, which are not to be considered limiting in any way. Rather, it is intended that aspects of this disclosure presented under any heading may be practiced together with any other aspect(s) presented under the same heading or different headings. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used in the present disclosure and in the appended claims, the singular forms "a," "an," and "the" include plural references unless the context clearly dictates otherwise. Moreover, while portions of this disclosure describe methods and structures together in examples, it is to be understood that the methods are not limited by the structures and the structures are not limited by the methods. Rather, it is contemplated that the methods may be practiced with structures other than those provided in the examples, and the structures may be used in ways different from the described methods. In addition, wherever methods are described herein, it is to be understood that such methods may be implemented in hardware, such as via at least one processor; and such methods may be implemented in software through computer readable media. Thus, the disclosures of methods herein are intended to likewise constitute disclosures of at least one processor configured to perform each method as well as non-transitory computer readable medium containing instructions to cause at least one processor to perform each method.

Overview of a Few Aspects of the Present Disclosure

Aspects of this disclosure are directed to devices, apparatuses, computer readable media, systems and methods involving removal of components of biological materials. Embodiments disclosed herein may be used, for example, for the treatment of diseases such as autoimmune diseases, cancers (including solid tumors and hematological or blood cancers), and/or post-transplantation complications such as graft vs. host disease (GVHD). Embodiments of this disclosure may involve biological filters that utilize specific MHC or HLA molecules, loaded with disease-specific peptides on the HLA groove, to identify, capture, and remove disease-specific pathogenic T-cell clones based on T-cell receptor (TCR) recognition from any type of biological fluid.

As used herein, a "major histocompatibility complex" (MHC) is a group of genes that code for proteins found on the surfaces of cells that help the immune system, specifically T-cells, recognize foreign substances. MHC proteins are found in all higher vertebrates. In human beings, the complex is also called the "human leukocyte antigen" (HLA) system. Throughout the disclosure, the terms MHC and HLA are used interchangeably. HLA proteins are typically responsible for regulating an individual's immune system and may be found on the surface of human cells. For example, HLA proteins may function by recognizing foreign, non-self substances in an individual and initiating an immune response to neutralize those substances. In order to initiate or stimulate an individual's immune response, foreign, non-self substances may be incorporated into HLA complexes for presentation to an individual's immune system. Each individual has a particular set—or type—of HLA proteins. In some embodiments, the HLA type of an individual may be determined using standard laboratory techniques in a certified clinical laboratory. For example, determination of an individual's HLA type may include analyzing a blood sample collected from the individual. Alternatively, the individual's HLA type may be determined by other suitable means.

As used herein, "pathogenic," when referring to cells, encompass both pathogenic cells and cell fragments, as well as other particles the removal of which may improve a clinical condition of a patient. Non-limiting examples of pathogenic cells are T-cells reactive against myelin basic protein (MBP) of a multiple sclerosis patient, T-cells stimulating an immune response against allogeneic or autologous transplantation, and secreted particles or cells abundant in a biological fluid which are associated with a disease. The term pathogenic cell also encompasses an abnormally high count of an otherwise healthy cell.

In some embodiments, a biological filter consistent with this disclosure may incorporate HLA monomers or multimers (e.g., dimers, tetramers, pentamer, dextramers) in a soluble form (e.g., HLA I or HLA II), which may be in a complete form (i.e., complete polypeptide) or in truncated form (i.e., truncated polypeptide), and that are attached to a capturing moiety of any kind (e.g., a peptide or an epitope thereof). In other instance, these molecules may be injected intravenously to recognize, capture, and remove specific T-cell clones. One to a few hours after injection, the patient may be connected to any filtration machine, with a unique filter consistent with this disclosure. The filter may contain special surface/molecules/reagents that react with the small capturing molecules attached to the HLA monomers or multimers. This may result in a capture of significant amounts (or substantially all) of the HLA monomers or multimers from the blood by the filter. The remainder of the blood components may be returned to the patient intact.

Methods described herein may involve identifying, capturing, and removing specific T-cell clones based on T-cell receptor (TCR) recognition without anchoring the HLA-peptide complexes to any surface or medium filter. For example, HLA molecules may be provided in a solution or other medium other than a surface or physical filter medium.

T-Cells and Autoimmune Diseases and Beyond

The immune system is composed of several types of cells, including T-cells. Certain T-cells can also mediate autoimmune diseases such as multiple sclerosis (MS) and insulin-dependent diabetes mellitus (IDDM). In both these diseases, specific organs are damaged. In the case of MS, an important ingredient of the central nervous system (CNS), called myelin, is the target of injury, while in IDDM the pancreas that produces insulin is injured to the point where the body can no longer produce insulin. These injuries appear because of a mistake in recognition of self-proteins as pathogens (non-self) by the immune system.

In an autoimmune patient's peripheral blood, especially in MS, it may be observed that the amount of peripheral T-cells is higher compared with healthy control. In addition, T-cells in MS patients have low activation thresholds, high proliferation rates, and increased survival.

Keying off these observations, some embodiments of the present disclosure seek to remove disease-specific pathogenic T-cells from the blood of patients. These specific T-cells are those which are directly responsible for the tissue damage and for the diseased condition. In the case of MS, this removal is performed to significantly slow the progression of the disease and possibly prevent neurological tissue damage in MS patients. The recognition of these T-cells by the filter is based on the existence of a special receptor that is expressed on T-cells, called a T-cell receptor (TCR). The harmful T-cells are characterized by a TCR which recognizes a component (i.e. peptide) of myelin. Recognition and binding of the myelin peptide to TCR of a T-cell can be achieved when this peptide is loaded on an HLA complex. A biological filter consistent with disclosed embodiments may therefore include a layer of HLA complex molecules which are loaded with the myelin peptide. The harmful T-cells that are responsible for disease progression bind to the filter and are thus filtered out. This filtering technology provides a non-pharmacological solution to treat diseases such as MS, and more generally may be used to remove other components of biological material.

For example, similar separation-based therapies consistent with this disclosure may be used to treat other autoimmune diseases. Examples of such other autoimmune diseases that may be treated using embodiments disclosed herein may include achalasia, Addison's disease, adult Still's disease, agammaglobulinemia, alopecia areata, amyloidosis, ankylosing spondylitis, anti-GBM/Anti-TBM nephritis, antiphospholipid syndrome, autoimmune angioedema, autoimmune dysautonomia, autoimmune encephalomyelitis, autoimmune hepatitis, autoimmune inner ear disease (AIED), autoimmune myocarditis, autoimmune oophoritis, autoimmune orchitis, autoimmune pancreatitis, autoimmune retinopathy, autoimmune urticaria, axonal & neuronal neuropathy (AMAN), Baló disease, Behcet's disease, benign mucosal pemphigoid, bullous pemphigoid, Castleman disease (CD), celiac disease, Chagas disease, chronic inflammatory demyelinating polyneuropathy (CIDP), chronic recurrent multifocal osteomyelitis (CRMO), Churg-Strauss syndrome (CSS) or eosinophilic granulomatosis (EGPA), cicatricial pemphigoid, Cogan's syndrome, cold agglutinin disease, congenital heart block, Coxsackie myocarditis, CREST syndrome, Crohn's disease, dermatitis herpetiformis, dermatomyositis, Devic's disease (neuromyelitis optica), discoid lupus, Dressler's syndrome, endometriosis, eosinophilic esophagitis (EoE), eosinophilic fasciitis, erythema nodosum, essential mixed cryoglobulinemia, Evans syndrome, fibromyalgia, fibrosing alveolitis, giant cell arteritis (temporal arteritis), giant cell myocarditis, glomerulonephritis, Goodpasture's syndrome, granulomatosis with polyangiitis, Graves' disease, Guillain-Barre syndrome, Hashimoto's thyroiditis, hemolytic anemia, Henoch-Schonlein purpura (HSP), herpes gestationis or pemphigoid gestationis (PG), hidradenitis suppurativa (HS) (acne inversa), hypogammalglobulinemia, IgA nephropathy, IgG4-related sclerosing disease, immune thrombocytopenic purpura (ITP), inclusion body myositis (IBM), interstitial cystitis (IC), juvenile arthritis, juvenile diabetes or Type 1 diabetes or insulin-dependent diabetes mellitus (IDDM), juvenile myositis (JM), Kawasaki disease, Lambert-Eaton syndrome, leukocytoclastic vasculitis, lichen planus, lichen sclerosus, ligneous conjunctivitis, linear IgA disease (LAD), lupus, Lyme disease chronic, Meniere's disease, microscopic polyangiitis (MPA), mixed connective tissue disease (MCTD), Mooren's ulcer, Mucha-Habermann disease, multifocal motor meuropathy (MMN) or MMNCB, multiple sclerosis, myasthenia gravis, myositis, narcolepsy, neonatal lupus, neuromyelitis optica, neutropenia, ocular cicatricial pemphigoid, optic neuritis, palindromic rheumatism (PR), PANDAS or Pediatric Autoimmune Neuropsychiatric Disorders Associated with Streptococcal Infections, paraneoplastic cerebellar degeneration (PCD), paroxysmal nocturnal hemoglobinuria (PNH), Parry Romberg syndrome, pars planitis (peripheral uveitis), Parsonage-Turner syndrome, pemphigus, peripheral neuropathy, perivenous encephalomyelitis, pernicious anemia (PA), POEMS syndrome, polyarteritis nodosa, polyglandular syndromes type I, II, III, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia (PRCA), pyoderma gangrenosum, Raynaud's phenomenon, reactive arthritis, reflex sympathetic dystrophy, relapsing polychondritis, restless legs syndrome (RLS), retroperitoneal fibrosis, rheumatic fever, rheumatoid arthritis, sarcoidosis, Schmidt syndrome, scleritis, scleroderma, Sjögren's syndrome, sperm & testicular autoimmunity, stiff person syndrome (SPS), subacute bacterial endocarditis (SBE), Susac's syndrome, sympathetic ophthalmia (SO), Takayasu's arteritis, temporal arteritis/giant cell arteritis, thrombocytopenic purpura (TTP), Tolosa-Hunt syndrome (THS), transverse myelitis, ulcerative colitis (UC), undifferentiated connective tissue disease (UCTD), uveitis, vasculitis, vitiligo, and Vogt-Koyanagi-Harada Disease. In one embodiment, the autoimmune disease is selected from multiple sclerosis, myasthenia gravis, Type 1 diabetes, inflammatory bowel disease (e.g., Crohn's disease, ulcerative colitis), and Lambert-Eaton syndrome.

Biological fluid filtering-based therapies consistent with this disclosure may also be applied to treatment of various cancers, including solid tumors, but particularly hematological or blood cancers such as leukemias, lymphomas, myelomas, myelodysplastic syndromes (MDS), myeloproliferative neoplasms (MPNs), and polycythemia vera (PCV).

Some disclosed embodiments may be used to treat leukemia, acute leukemia (AL), other cancers, immune system related diseases and disorders, allergy, anaphylaxis, asthma, transplant rejection (including GVHD), post transplantation states, myasthenia gravis (MG), Lambert-Eaton syndrome, multiple sclerosis (MS), polycythemia vera (PCV), thrombocytosis, other myeloproliferative diseases, and viral infections manifested on pathological cell surface.

Biological Filter

Some aspects of the present disclosure relate to filters, including biological filters and methods for producing biological filters. Nevertheless, it should be noted that aspects of the disclosure in its broadest sense is not limited to biological filters. Rather, some aspects of the foregoing disclosure do not involve filters and other aspects of the disclosure may be applied to filters other than biological filters.

The term "biological filter" refers generally to any medium, regardless of form, that uses biological mechanisms to remove biological material from biological fluid. By way of example, such a filter may include organic molecules, such as proteins. Removal of biological material may occur through any biological or chemical process, such as through binding, bonding or reacting. One such mechanism may include molecular binding. The filter may have any suitable form capable of a removal function. For example, it may be configured in the form of or to include one or more sheets of material to which biological fluid components bind, bond, or otherwise react; or other structures that result in a similar effect, such structures including but not limited to mesh, fibers, gel, beads, scaffold, or any other material with surface area configured for biological filtering. Such filters may be configured to capture cells, proteins, nucleic acids, lipids, polysaccharides, or any other biological materials. For example, the filter might include proteins or may be anchored with proteins that recognize and capture pathogenic cells or non-pathogenic cells, depending on the function that the filter is designed to accomplish. In some embodiments, pathogenic cells may have the same role as non-pathogenic cells except that they recognize self-structures and materials and attack them. By way of example, a filter may be designed to remove one or more of a host of pathogenic cells associated with a host of diseases. For example, the filter may be designed to remove pathogenic lymphocytes.

By way of non-limiting example, FIG. 1 illustrates a biological filter 102 including a housing 104, an inlet port 106 for directing biological fluid flow 108 into the housing 104, and an outlet port 110 for directing the biological fluid out of the housing. A filtering medium 114 may be contained within the housing as will be discussed later in greater detail. While the housing 104 is illustrated as cylindrical, the housing may be of any suitable shape and may be constructed of any suitable material.

Consistent with disclosed embodiments, a filter may include an inert surface medium. The term "inert" refers generally to a substance or material that does not change, absorb, or react with non-specific particles, such as non-predefined cells or soluble particles. As used herein, the term "medium" may include any substance capable of serving as a base, support, or anchor for material that selectively binds to cells. In other words, the medium "hosts" the material that selectively binds to cells. In some exemplary embodiments, the inert surface medium may include polysulfone. In other exemplary embodiments, the inert surface medium may include a polysulfone derivative, glass matrices, silicon matrices, polydimethylsiloxane (PDMS), polycarbonate, polyetherimide (Ultem), Tritan or a combination of the above or other substances. In some embodiments, the inert surface medium may further include a polyelectrolyte either alone or in combination with another of the above-identified materials or other substances or materials. In other embodiments, the inert surface medium may include at least one of polyethylene glycol (PEG), a PEG derivative, polystyrene, avidin or streptavidin. Alternatively, the surface of the filter may be somewhat or highly absorbent or reactive with non-specific particles.

FIGS. 2A-2D illustrate a few non-limiting examples of structures of inert surface media that may be used to form filtering media, such as the filtering medium 114 illustrated in FIG. 1. FIG. 2A illustrates sheets 202 of inert surface media; FIG. 2B illustrates fibers 204 of inert surface media; FIG. 2C illustrates beads 206 of inert surface media; and FIG. 2D illustrates a sponge-like structure 208 of inert surface media. Other solid, semi solid, or fluid materials may be used as the inert surface media, so long as they are capable of serving as a base for a filtering medium.

In certain embodiments, the filter may include a plurality of layers configured to permit fluid flow therebetween. Any layering structure may be used so long as fluid may contact a sufficient portion of the filtering medium to achieve an intended filtering function. Thus, with reference to FIGS. 2A-2D for example, the layering of sheets 202, fibers 204, beads 206, or portions of a sponge-like structure 208 with gaps therein are non-limiting examples of a plurality of layers configured to permit fluid flow therebetween. In the case of the sponge-like structure 208, portions on opposite sides of an interstice may be considered separate layers within the meaning of this disclosure.

Figure 3:
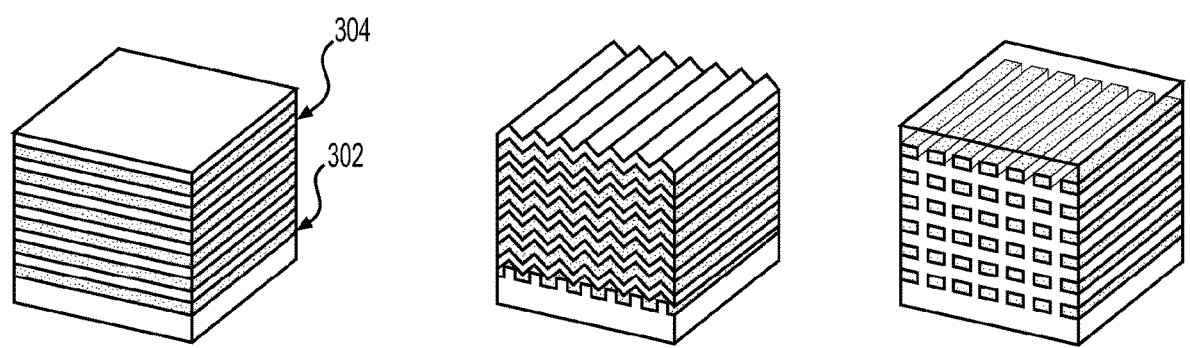
FIG. 3 illustrates exemplary layering arrangements of multilayered filters consistent with embodiments of this disclosure.

Portions of adjoining layers may contact each other or may be spaced apart from each other by, for example, scaffolding. FIG. 3 provides examples of spaced layers permitting fluid flow therebetween, where hatched areas 302 represent the filtering medium and non-hatched areas 304 represent regions through which fluid may flow. Areas 304 may be substantially void of structure or may include a porous or channeled structure therein for permitting fluid flow therethrough. As illustrated in FIG. 3, layers of a multilayered filter may be substantially planar, contoured, or arranged in a matrix of channeled rows and columns. Again, the particular structure is not necessarily critical in a broadest sense of this disclosure, so long as the structure is capable of enabling a fluid to be filtered via contact with the filtering medium.

The volume of a housing or filtering medium may be any size, depending on specifications for the desired use. In some embodiments, the housing or filtering medium may be sized so as to allow for one or more cycles of filtration, enabling batches of biological material to circulate or recirculate therethrough.

In some embodiments, the housing and filter may be configured to enable flow of biological fluid without damaging components of the biological fluid, such as cells. For example, the filter may be configured so as to not apply sheer force to biological fluid flowing therethrough. In other embodiments, the filter may be designed to regulate pressure adjustments upon fluid administration. In certain embodiments, the filter may be configured to prevent pressure build up or a pressure drop upon exposure to fluid. In some embodiments, a scaffold of the filter may be sized so as to substantially prevent blockage of flow. For example, the scaffold may be sized to prevent fluid components, such as blood clots, platelets, and protein aggregates, from blocking flow or from preferentially collecting in some areas of the housing or filter.

In some embodiments, filtration may include subjecting biological samples to more than one filter. For example, more than one filter may be connected serially or in parallel to one another. In particular embodiments, each filter in a multi-filter system may be designed to capture a specific cell type, thus enabling the capturing of multiple cell types when subjecting a biological sample to the system. By way of example, in a multi-filter system having two filters, the first filter may be designed to capture CD8+ T-cells and the second filter may be designed to capture CD4+ T-cells. These are only examples for illustrative purposes only, as filters can be designed to capture a host of biological components depending upon the intended design of the filter.

In some embodiments, filtration of biological material may be performed extracorporeally or outside the body of an individual. By way of example, filtration may be performed by drawing fluid from a vein of an individual, passing the fluid through a filter, and returning the fluid to either another vein or the same vein of the individual in a closed circuit. Alternatively, filtration may include collecting a sample from an individual, filtering the sample in a laboratory, and returning the filtered sample to the individual. In a separate embodiment, a filter may be implanted in a blood vessel in the body of an individual. Such a filter may be incorporated into a vascular stent, with the stent serving as a host medium and the HLA-peptide complexes, for example, bound to the host medium. Such a stent-based biological filter might be temporarily deployed via a balloon catheter or may be self-expanding, with the stent being removable after its filtering capacity is depleted. If implanted, the filter may, for example, be positioned in proximity to a lymphoid organ, or any other organ. In further embodiments, the implanted filter may bind cells continuously and be replaceable. For example, a port may be provided in the vasculature of a patient, and a removable filter might be accessible via the port. A septum, for example, might have a replaceable biological filter component that traps pathogens enabling the pathogens to be ultimately removed when the filter is replaced. In another example, a biological filter may be implanted within a body of a patient and connected to the patient's vasculature in a manner similar to proposed implantable artificial kidneys. In some such embodiments, the filter might remain implanted for extended periods with the filter being replaced intermittently. Alternatively or additionally, a biological filter might be refurbished within the body to minimize the need for more frequent replacement. Through injection of additional HLA-peptide complexes, for example, fresh complexes may be bound to an already implanted filter medium. In this way, it may be possible to achieve additional filtering capacity from an already implanted filtration medium. In yet another embodiment, a portable filter may be worn or carried by a patient or may be located next to a patient's bed during sleep to enable extracorporeal blood flow through the filter with or without the use of an external pump. Any of these embodiments may be used for achieving clinical results (e.g., removal of pathogens to diminish disease symptoms) or may be employed for conducting blood tests that measure particular pathogen or cell levels.

Thus, the filter may include an external element. By way of example, the external element may be cylindrically-shaped, columnar-shaped, or shaped in any other suitable form so long as it is capable of retaining a filter medium for an intended filtration purpose. The external element may be made of biocompatible materials, such as polystyrene.

In some embodiments, the biological filter may include human leukocyte antigen (HLA) proteins disposed on the inert surface medium.

In some embodiments, the HLA protein is altered from endogenous HLA protein. For example, the HLA protein may include at least one of a monomer or multimer, And other modifications and additions such as a single amino acid, a string of amino acids, an HLA protein subunit, or multiple subunits. In some embodiments, the HLA protein may be truncated or shortened from its full length. The truncated HLA protein may be further modified, for example, by adding at least one additional amino acid residue to either end of the truncated protein. As a non-limiting example, the truncated HLA protein may be altered by adding a cysteine as the C-terminal residue.

The HLA proteins may be recombinantly produced. Alternatively, or additionally, HLA proteins may be obtained endogenously from an individual, such as a patient. In certain embodiments, recombinantly designed HLA proteins may include recombinant proteins similar to proteins of a patient. For example, the HLA proteins may be HLA-typed to match a patient. In some embodiments, the HLA protein may be HLA I or HLA II. In some embodiments, recombinantly designed HLA proteins may include a peptide-binding cleft or groove for loading and binding to endogenous or synthesized peptides that may be subsequently presented.

The HLA protein may be disposed on the inert surface medium, as previously mentioned. Disposition may occur through binding, bonding, anchoring, chemical reaction, or any other manner of attachment of the HLA protein to the inert surface medium. For example, a surface of the filter may be chemically designed to enable specific molecular and chemical properties in order to react with the HLA protein. The HLA proteins may be disposed on the inert surface medium, for example, through covalent bonding, non-covalent interactions, or adsorption. Examples of non-covalent interactions include but are not limited to electrostatic interactions, van der Waals forces, π-effects, and hydrophobic effects. In particular embodiments, the HLA protein may bind to the surface of the filter via an analog. By way of example, the HLA proteins may be disposed on the inert surface through a maleimide analog. In other embodiments, the HLA protein may covalently bind to the surface of the filter via a maleimide analog. In certain embodiments, the HLA protein may be introduced to the surface of the filter in a solution in an excess amount in order to enable maximal saturation of the surface of the filter with the HLA protein. In particular embodiments, the HLA protein may bind to the surface of the filter via thiol binding, disulfide binding, amine binding, or binding of any other suitable functional group. Alternatively, the HLA protein may bind covalently to the surface of the filter at, for example, a cysteine residue.

Figure 4:
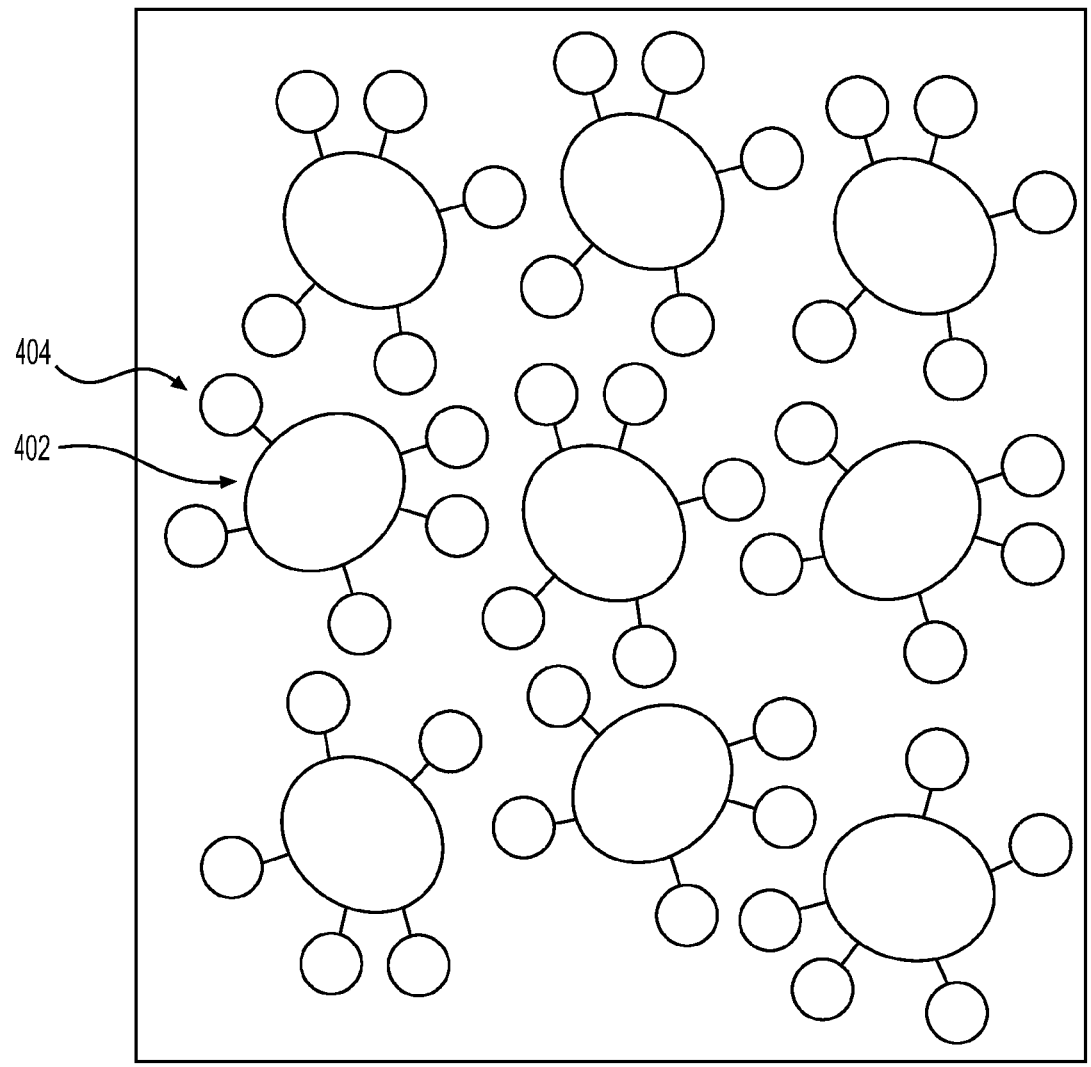
FIG. 4 is a schematic representation of inert surface media with HLA proteins attached thereto consistent with embodiments of this disclosure.

By way of schematic representation, inert surface medium 402 in FIG. 4 includes HLA proteins 404 attached thereto. The attachment mechanism may be any mechanism, as previously described, and the inert medium, while illustrated as beads in FIG. 4, can be any form of inert medium onto which the HLA proteins 404 may be connected, including but not limited to the forms illustrated in FIGS. 2A-2-D. Alternatively, the inert surface medium 402 may be fluid molecules and the HLA proteins 404 may be disposed on the fluid molecules.

Figure 5:
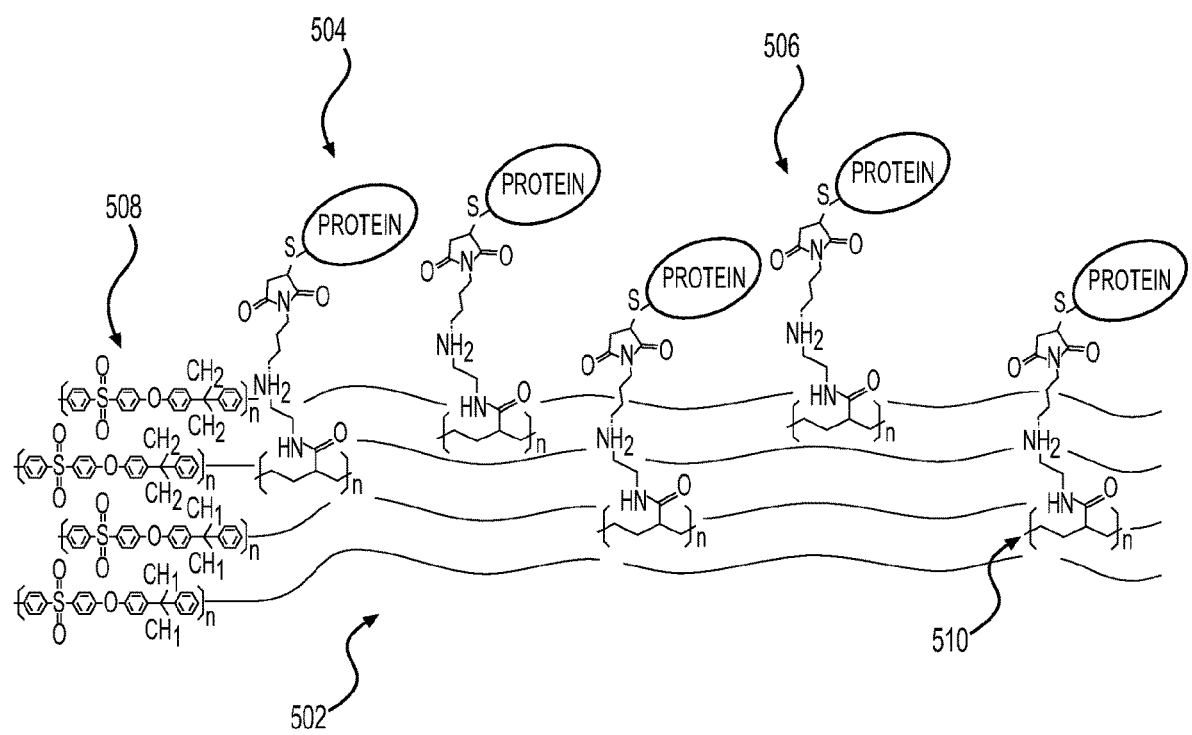
FIG. 5 is a schematic illustration of HLA proteins attached via maleimide linkers to an inert surface medium consistent with embodiments of this disclosure.

In some embodiments, the HLA proteins may be disposed on the inert surface in a manner such that anchoring locations for HLA proteins are spaced from each other by at least the width of an HLA binding groove. This spacing enables T-cells to bind to the HLA proteins. And such spacing, if maintained across a filter surface, may maximize efficiency of the filter. By way of one example in FIG. 5, HLA proteins 504 are attached via a maleimide linker 506 to the inert surface medium 502. In this example, surface medium 502 includes polysulfone 508 and poly(2-aminoethyl) acrylamide 510.

In some embodiments, antigen peptides may be bound to the HLA proteins on the inert surface medium. The term "peptide" generally refers to a short chain of amino acids (e.g., no longer than 30 amino acids, 25 amino acids, 20 amino acids, or 15 amino acids) bound together by a peptide bond between every two amino acids. In some embodiments, a peptide may be synthesized by standard procedures. In certain embodiments, the peptide may be synthesized chemically either by manual or automatic procedures. Alternatively, the peptide may be synthesized by fluorenylmethoxycarbonyl protecting group chemistry.

The term "antigen peptide" or "immunogenic peptide" refers generally to a peptide's potential for eliciting an immune response. A peptide's antigenicity or immunogenicity may be determined by standard means. In some embodiments, antigen peptides are loaded onto HLA proteins to form HLA-peptide complexes. By way of example, loading may occur through protein-peptide binding. Specifically, HLA proteins have a peptide-binding cleft that enables protein-peptide binding to occur. The peptide-binding cleft is formed by two protein subunits, α1 and α2 for HLA I, and a1-b1 for HLA II. When the peptide-binding cleft is formed, antigen peptides are able to bind to the HLA protein by amino acid residue interactions between the peptide-binding cleft and the antigen peptide. Exemplary interactions include hydrogen bonding, ion interactions, hydrophobic interactions, and pie stacking. Antigen peptides are able to bind with the HLA peptide-binding cleft, forming HLA-peptide complexes.

In some embodiments, antigen peptides may be associated with disease in patients and may be loaded onto HLA proteins to form HLA-peptide complexes capable of selectively binding antigen-specific T-cell receptors. For example, after loading as discussed above, antigen peptides may be recognized by T-cells of an individual's immune system and initiate a T-cell attack. In these instances, antigen peptides that form a complex with HLA proteins are capable of selectively binding antigen-specific T-cell receptors.

In some embodiments, the antigen peptides and the HLA proteins are selected to enable antigen-specific T-cell receptors to bind to a complex of the antigen peptides and the HLA-proteins when T-cells are brought into contact with the complex, thereby securing specific T-cells to the inert surface medium via the complex. T-cells are brought into contact with the HLA-peptide complex via a space that enables interaction between the complex and the desired T-cell to capture. The contact may occur through fluid flow, such as the flow of blood or constituents of blood such as plasma or particular blood cells. The recognition is based on highly specific attachment of only the desired T-cells that express the specific T-cell receptor that interacts with the specific HLA-peptide complex.

The term "antigen-specific T-cell receptors" refers generally to receptor proteins on the surface of T-cells that bind to specific antigens. T-cells have unique T-cell receptors on their surface that cause specific T-cells to bind specific antigens and other T-cells to not bind to the same antigen but instead bind to a different antigen. This process is generally referred to as selective binding. The relationship between T-cells with receptors that only recognize specific antigens allows selective binding of T-cells with antigen-specific receptors to only bind a specific antigen. In some embodiments, the HLA-peptide complex disposed on the inert surface medium includes an antigen peptide selected to bind to a specific T-cell receptor. Once the antigen-specific T-cell receptor selectively binds and forms a complex with the HLA-peptide complex, the specific T-cells are thereby secured to the inert surface medium via the complex.

In some embodiments, disease-associated antigenic peptides may be self-peptides, or non-foreign peptides specific to an individual. In particular embodiments, the antigen peptides may be synthetically produced. Synthetic production of antigen peptides may be done manually or automatically. For example, antigen peptides may be synthetically produced using fluorenylmethoxycarbonyl protecting group (FMOC) chemistry. Antigen peptides may also be recombinantly produced. Recombinantly produced antigen peptides may be similar to naturally occurring peptides, or they may be altered. In particular embodiments, antigen peptides may be recombinantly produced in frame with the HLA protein. For example, the same plasmid used to recombinantly produce HLA protein according to the aspects of the invention can be used to recombinantly produce the antigen peptide.

In some embodiments, disease-associated antigenic peptides may include proteins specific to a damaged tissue/organ of an individual. For example, such peptides may be derived from cells of the central nervous system. In particular examples, such peptides may include those that form part of the myelin sheath that surrounds axons in the central nervous system of an individual. Alternatively, disease-associated antigenic peptides may include proteins common to most or all cell types. By way of example, such peptides may include cytoplasmic, cytoskeletal, nuclear, or membrane proteins.

Antigen peptides may be associated with a variety of diseases. For example, an antigen peptide may be derived from a protein associated with multiple sclerosis. Such antigen peptides may be derived from myelin oligodendrocyte glycoprotein (MOG), myelin basic protein (MBP), myelin proteolipid protein (PLP), opalin protein, oligodendrocyte-specific protein (OSP), myelin-associated glycoprotein (MAG), or a combination thereof. In certain embodiments, the antigen peptide may be $MBP_{87-99}$, $MBP_{85-99}$, $MBP_{83-96}$, $MBP_{217-231}$, $MBP_{88-102}$, $MBP_{282-296}$, $PLP_{91-110}$, $PLP_{131-151}$, $PLP_{283-252}$, $PLP_{263-277}$, $PLP_{58-72}$, $PLP_{13-27}$, $OPALIN_{46-60}$, $OPALIN_{27-41}$, $OPALIN_{127-141}$, $MOG_{210-224}$, $MOG_{29-43}$, $MOG_{176-190}$, $MOG_{225-239}$, $OSP_{74-88}$, $OSP_{114-128}$, $MAG_{8-22}$, $MAG_{467-481}$, $MAG_{529-543}$, or a combination thereof.

Disease-associated antigenic peptides may be identified or analyzed by standard methods. In some embodiments, the identified peptides may be quantified. Alternatively, the amino acid sequence of such peptides may be determined. Such peptides may be compared to a database of antigens to derive relevant information about the peptides. For example, a peptide's binding affinity for a particular HLA may be measured. Thus, identifying or analyzing an antigenic peptide may include comparing the peptide with a database of disease-related antigenic peptides that includes peptide binding affinities for HLA complexes. In certain embodiments, identification or analysis of peptides may include examining peptides separated from HLA complexes collected from tissue of a diseased individual. For example, peptides from cerebrospinal fluid of a diseased individual may be examined. Alternatively or additionally, tissue from a diseased individual may be collected. A population of HLA complexes with connected or loaded peptides may be isolated from cells of the diseased individual. The peptides may then be separated from the HLA complexes by, for example, chemical means. The separated peptides may then be sequenced and analyzed for frequency in order to be linked to the particular disease of the individual. Using these mechanisms, a filter, as previously described, may be personalized to treat a disease of a specific individual.

Biological Filter for Cytoreduction of MS-Associated T-Cells

Consistent with disclosed embodiments, the biological filter as described above may be used for the cytoreduction of specific cells. For example, the filter may be used for cytoreduction of pathogenic cells or non-pathogenic cells. As used herein, the term "cytoreduction" generally refers to a procedure through which specific cells, or groups of cells are removed from a composition, thus lowering their relative percentage in the total population of cells. The reduction is achieved by a specific recognition of a unique cell subset, in other words, specific clonal cytoreduction rather than applying standard techniques that are not able to discriminate between different cells with different biological or physical properties. In some embodiments, the cells include T-cells. For example, the filter may be configured to remove pathogenic T-cells associated with a disease or associated with recognition of certain structures of proteins or peptides. In a particular embodiment, the biological filter may be used for the cytoreduction of multiple sclerosis-associated T-cells.

Disclosed filters may be used on a patient. As used herein, the term "patient" may refer to a subject with a disease or other affliction. A patient may be a human or any other mammal. In some embodiments, a method of removing specific T-cells is contemplated. The term "specific T-cells" may refer to a group of T-cells expressing a particular T-cell antigen receptor, specific clone of T-cells. The group of T-cells expressing a particular T-cell antigen may be targeted for removal if, for example, the group is identified as causing or otherwise impacting the patient's affliction. In other embodiments, the specific T-cells may include a plurality of groups of T-cells, wherein each group expresses a different T-cell antigen receptor and the groups expressing different T-cell antigen receptors may be targeted for removal.

In some embodiments, T-cells which do not express the particular T-cell antigen receptor or receptors being targeted may not be removed. As will be appreciated by one skilled in the art, the term "T-cell" may include any type of lymphocyte which develops in the thymus gland and which plays a central role in the immune response. In some embodiments, the specific T-cells may include one or more of helper CD4+ T-cells, cytotoxic CD8+ T-cells, naïve T-cells, memory T-cells, regulatory CD4+ T-cells, natural killer T-cells, mucosal associated invariant T-cells and/or gamma delta T-cells. Alternatively or additionally, the specific T-cells may include at least one of CD4+ cells or CD8+ cells.

Targeted T-cells may be either pathogenic or non-pathogenic. Pathogenic T-cells may play a similar role as non-pathogenic T-cells except that pathogenic T-cells may recognize self-structures and materials and attack them. The term "pathogenic" is as defined above. By targeting and removing pathogenic cells, the disease in the patient may be mitigated. Non-pathogenic T-cells may be targeted for removal, for example, if it is anticipated that a particular affiliation will evolve to a point where non-pathogenic T-cells in the present may become pathogenic in the future. Thus, proactive removal of non-pathogenic cells may prevent later manifestations of disease.

The pathogenic cells may be associated with any one or any combination of the autoimmune diseases described above. In certain embodiments, the pathogenic cells may be associated with autoimmune diseases including but not limited to multiple sclerosis (MS), lupus, celiac, Sjogren's syndrome, polymyalgia rheumatica, scleroderma, Ankylosing spondylitis, type 1 diabetes, alopecia areata, vasculitis, autoimmune hepatitis, autoimmune lymphoproliferative syndrome (ALPS), autoinflammatory Diseases, Goodpasture syndrome, Lambert-Eaton syndrome, antiphospholipid syndrome (APS), neuromyelitis optica (NMO), paraneoplastic syndromes, primary biliary cholangitis, Stiff-person syndrome (SPS), antiphospholipid antibody syndrome (APS), or temporal arteritis. In a particular embodiment, the autoimmune disease is multiple sclerosis.

Figure 6:
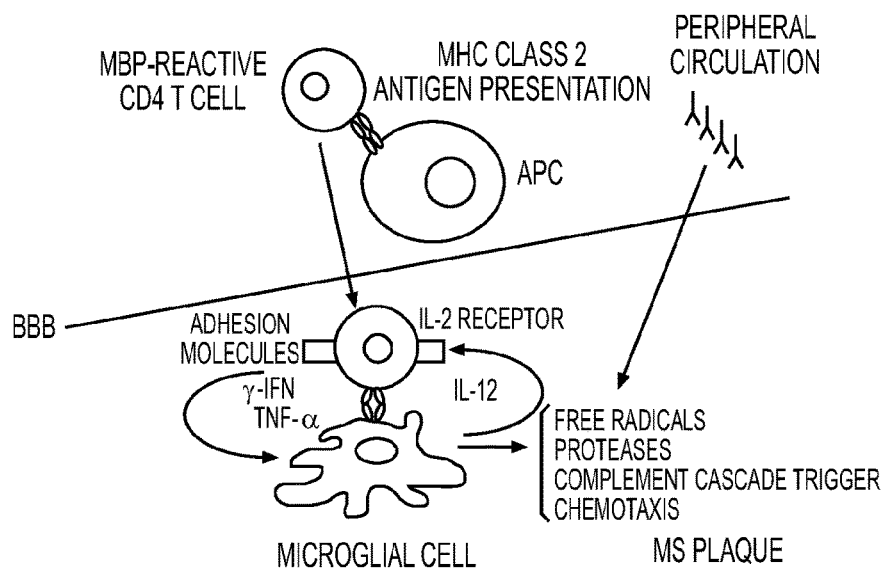
FIG. 6 is a schematic illustration of the molecular pathogenesis of multiple sclerosis.

Studies have shown that the adaptive immune system is strongly implicated in the molecular pathogenesis of multiple sclerosis. As illustrated in FIG. 6, autoantigens derived from CNS proteins such as myelin trigger activation of the immune system, causing components such as T-cells, B cells, and macrophages to infiltrate across the blood brain barrier, resulting in inflammation, demyelination, gliosis, and neuroaxonal degeneration. There is currently no cure for the disease.

Aspects of the filter may include a medium hosting material that selectively binds to antigen-specific T-cell receptors. As defined above, the term "medium" may include any substance capable of serving as a base, support, or anchor for material that selectively binds to cells. Because the binding material is anchored to the medium, when the cells become bound to the binding material, the cells effectively become trapped on the medium to which the binding material is anchored. The material that selectively binds to cells may vary depending on the intended use of the filter. By way of example, the binding material on the medium may be configured to capture cells, proteins, nucleic acids, lipids, polysaccharides, or any other biological materials. Details of the medium are discussed in other paragraphs herein and are not repeated to avoid repetition. "Selective binding" as used herein refers to any biological or chemical process where a target preferentially combines in a manner causing the target to be removed from the environment in which it was located. In a broad sense, binding encompasses any process of combination, adherence, coupling, or reaction that causes the target cells to be removed.

Many types of surface media may be used, including solids, semi-solids or fluids. If solid or semi-solid, the medium can have any form. Examples provided in FIGS. 2A-2D include sheet material, fibers, beads, and sponge-like material. Other examples include mesh structures, liquid and gels. Similarly, the make-up of the medium can vary depending on intended use. By way of example only, the medium may be characterized in one or more of the following ways: inert, non-synthetic; synthetic; a polymer; a high performance thermoplastic; polysulfone; a polysulfone derivative; a glass matrix; a silicon matrix; polydimethylsiloxane (PDMS); polycarbonate; polyetherimide (Ultem); Tritan; a polyelectrolyte; polyacrylic acid; or poly(2-aminoethyl) acrylamide. Alternatively or additionally, the medium may include polyacrylic acid present at about 5% to about 40% mass percentage; polysulfone present at about 60% to about 95% mass percentage; polystyrene; polyethylene glycol (PEG) or a PEG derivative; PEG density maximized by generating six-arm star shaped molecules of PEG that can be intermolecularly crosslinked; and/or avidin, streptavidin or any variation thereof. Again, these are only examples and are not to be considered limiting of this disclosure in its broadest sense.

Figure 7A:
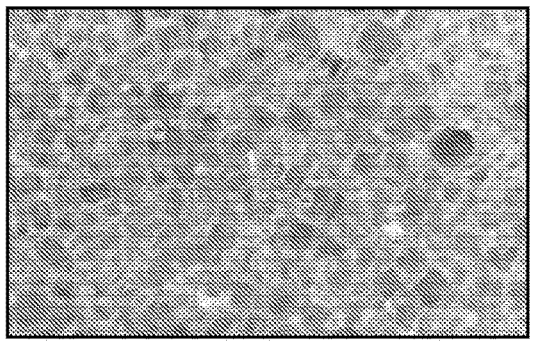
FIG. 7A illustrates a PDMS medium, consistent with embodiments of this disclosure.
Figure 7B:
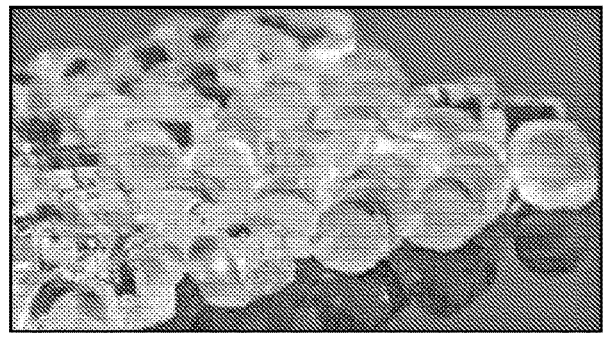
FIG. 7B illustrates a polycarbonate medium, consistent with embodiments of this disclosure.
Figure 7C:
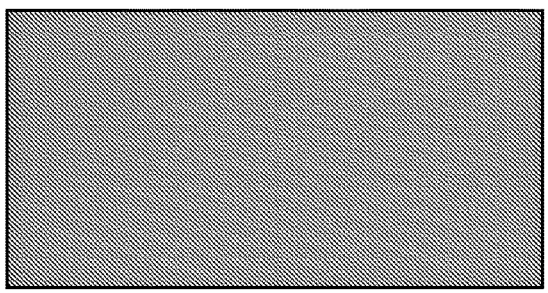
FIG. 7C illustrates an Ultem medium, consistent with embodiments of this disclosure.
Figure 7D:
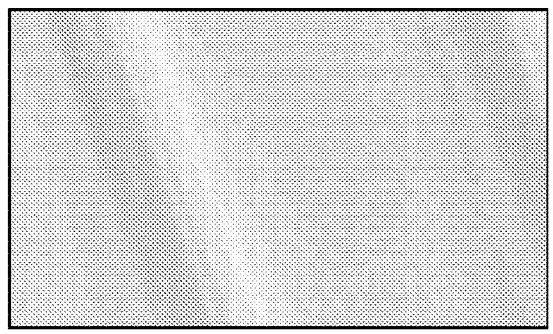
FIG. 7D illustrates a Tritan medium, consistent with embodiments of this disclosure.

By way of schematic representation, FIGS. 7A-7D show non-limiting examples of the medium consistent with embodiments of this disclosure. FIG. 7A shows PDMS material; FIG. 7B shows polycarbonate material; FIG. 7C shows Ultem material; and FIG. 7D shows Tritan material.

The medium may host a binding material that selectively binds to and captures, biological material, such as cells. For example, the cells may be pathogenic T-cells, and may be attached to the medium in any way, including through covalent bonding, non-covalent interactions or adsorption. Non-covalent interactions may include hydrogen bonding, ionic interactions, hydrophobic interactions, or pie stacking. In certain embodiments, the binding material may include a protein. For example, in some embodiments, the protein may include an antibody. In a particular embodiment, the protein may include a human leukocyte antigen (HLA). While binding material may selectively bind to only specific cells, the binding material may be initially bound to a host medium. Therefore, use of the phrase "selectively binds to only the specific cells" refers to the selective binding of the cell (or other biological material) capture process and not to the mechanism connecting the host medium to the binding material, which connection may occur through binding.

In some embodiments, the selectively binding host material includes an HLA. The HLA may be bound to a peptide to form an HLA-peptide complex. The HLA-peptide complex may recognize a specific epitope on the biological material (e.g., T-cells.). In certain embodiments, the peptide bound to the HLA may be derived from a protein implicated in a disease. In one example, the binding material includes HLA-myelin-peptide complexes selected to bind with myelin-specific T-cell receptors, to thereby enable specific binding of a population of T-cells that recognize the HLA-myelin-peptide complex. The HLA-myelin-peptide complex may be disposed on the filter in medium in any way, including through covalent bonding, non-covalent interactions or adsorption. As used herein, the term "disposed" may generally refer to the process by which a protein of choice can be connected via chemical reaction (or other mechanism) to a desired surface. The surface may be chemically designed to confer it with specific molecular and chemical properties in order for it to react with the protein. The disposition may occur when the surface is introduced to a solution including the proteins of interest, preferably in an excess amount to enable maximal saturation of the surface with proteins.

If by way of example, the medium may include avidin, streptavidin or any variation thereof, the capture material may be linked to a biotin, which may interact with the avidin, streptavidin, or variation thereof on the surface of the medium, thereby anchoring the capture material to the medium. By way of another example, the medium may include a free carboxyl group, amine group, maleimide group, or any other functional group, which may interact with a functional group on the capture material, thereby anchoring the capture material to the medium. In yet another example, the medium includes a blend of polysulfone and polyacrylic acid and the capture material may be a protein, which may be bound to the medium via the carboxyl group of the polyacrylic acid. Further, the blend of polysulfone and polyacrylic acid may be modified to include an amine group and the protein may be bound to the medium via reaction with the amine group. In a further example, the blend of polysulfone and polyacrylic acid may be modified to include a maleic acid, a maleimide group or an analog thereof. The maleic acid, a maleimide group or analog thereof may be elongated with a carbohydrate linker. The capture material may be bound to the medium via reaction with the maleic acid, a maleimide group or analog thereof. In a particular embodiment, the HLA-peptide complexes are disposed on the medium through maleic acid, maleimide or a maleimide analog.

Figure 8:
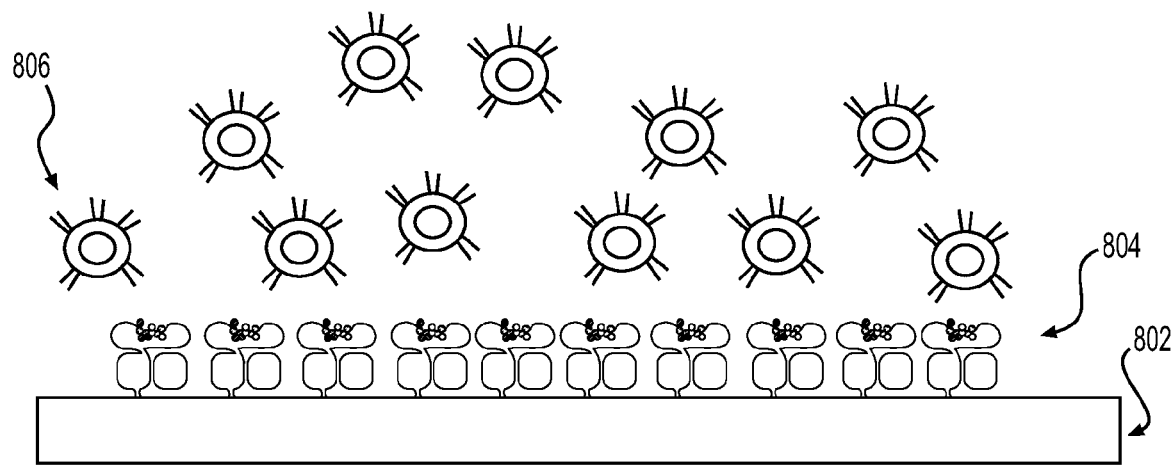
FIG. 8 schematically illustrates an exemplary biological filter for cytoreduction of multiple sclerosis-associated T-cells consistent with embodiments of this disclosure.

By way of schematic representation in FIG. 8, a medium 802 including HLA-myelin-peptide complexes 804 that recognize T-cell receptors on a group of T-cells 806. The medium 802, while illustrated in sheet form, can be in any form including but not limited to the forms illustrated in FIGS. 2A-2D.

As described above, the term "human leukocyte antigen" (HLA) refers generally to a system or complex of proteins encoded by an individual's major histocompatibility (MHC) gene complex. Three classes of HLA proteins are found in humans: HLA I, HLA II and HLA III. These three classes of HLA proteins differ in various ways, including structurally, in expression patterns, and in target recognition. As used herein the term "HLA I" generally refers to the HLA class that is composed of an a chain and a β2-microglobulin chain, is expressed in all nucleated cells, and interacts with CD8+ T-cells in vivo. As used herein, the term "HLA II" generally refers to the HLA class that is composed of an a chain and a β chain, is expressed in antigen-presenting cells, and interacts with CD4+ T-cells in vivo. HLA proteins are typically responsible for regulating an individual's immune system and may be found on the surface of human cells. For example, HLA proteins may function by recognizing foreign, non-self substances in an individual and initiating an immune response to neutralize those substances. In order to initiate or stimulate an individual's immune response, foreign, non-self substances may be incorporated into HLA complexes for presentation to an individual's immune system. Each individual has a particular set—or type—of HLA proteins. In some embodiments, the HLA type of an individual may be determined using standard laboratory techniques in a certified clinical laboratory. For example, determination of an individual's HLA type may include analyzed a blood sample collected from the individual. Alternatively, the individual's HLA type may be determined by other suitable means. As used herein, the term "HLA typing" generally refers to the process by which the HLA set of an organism is determined. For example, HLA typing may be performed via DNA sequencing, microlymphocytotoxicity assays, or via hybridization of DNA to oligonucleotide probes, which identifies one or more HLA types of the patient. For example, HLA typing may include testing for antibodies targeted to specific HLA proteins. Some methods for HLA typing define HLA alleles and allele groups using DNA-based methods. Different DNA-based molecular techniques may be used depending on the clinical application. Some HLA typing procedures may involve reverse SSO (rSSO) or sequenced based typing (SBT). Any technique that can be used to determine an HLA type is within the scope of this disclosure. Many labs perform HLA typing services, and determining an HLA type within the meaning of this disclosure may include performing the typing procedure or sending a body fluid sample to a lab that performs the procedure and returns the results. In some embodiments, the capture material may include an HLA protein and may further include a peptide to form an HLA-peptide complex. The HLA-peptide complex may be disposed on the medium, for example, through maleic acid, maleimide or an analog thereof.

In some embodiments, the HLA-peptide complex may recognize a T-cell receptor on a specific group of T-cells, thereby capturing the T-cells on the medium. In other embodiments, it is contemplated that a plurality of different HLA-peptide complexes may each recognize a different T-cell receptor or a different T-cell clone, on a plurality of different groups of T-cells.

The term "T-cell receptor" (TCR) generally refers to a protein complex found on the surface of T-cells. Due to genetic recombination, TCRs exhibit remarkable diversity, with each type of T-cell receptor recognizing specific antigen peptides bound to HLA, thereby initiating a signal cascade that activates other components of the immune system in vivo.

In some embodiments, immunogenic peptides may be associated with a variety of diseases, including, for example, autoimmune diseases. Disease-associated immunogenic peptides may be identified or analyzed by standard methods as described previously. In some embodiments, the autoimmune disease is MS. For example, the immunogenic peptides may be derived from myelin proteins, including, but not limited to, myelin oligodendrocyte glycoprotein (MOG), myelin basic protein (MBP), or myelin proteolipid protein (PLP), opalin protein, oligodendrocyte-specific protein (OSP), myelin-associated glycoprotein (MAG), or a combination thereof. As described previously, exemplary embodiments of immunogenic peptides include $MBP_{87-99}$, $MBP_{85-99}$, $MBP_{83-96}$, $MBP_{217-231}$, $MBP_{88-102}$, $MBP_{282-296}$, $PLP_{91-110}$, $PLP_{131-151}$, $PLP_{283-252}$, $PLP_{263-277}$, $PLP_{58-72}$, $PLP_{13-27}$, $OPALIN_{46-60}$, $OPALIN_{27-41}$, $OPALIN_{127-141}$, $MOG_{210-224}$, $MOG_{29-43}$, $MOG_{176-190}$, $MOG_{225-239}$, $OSP_{74-88}$, $OSP_{114-128}$, $MAG_{8-22}$, $MAG_{467-481}$, $MAG_{529-543}$, or a combination thereof. Alternatively or additionally, complexes of HLA proteins and peptides derived from other myelin-associated proteins may also be utilized, including, but not limited to, myelin-associated glycoprotein (MAG), oligodendrocyte-specific protein (OSP) and myelin-associated oligodendrocytic basic protein (MOBP). In some embodiments, HLA proteins complexed with peptides derived from non-myelin MS-associated proteins are also contemplated. By way of example, such antigen peptides may be derived from an aquaporin channel protein, αB-Crystallin, transaldolase-H, S-100 (105), and 2',3'-cyclic nucleotide-3'-phosphodiesterase (CNPase).

In some embodiments, the HLA protein in an HLA-peptide complex may be HLA-typed to match a patient. As described previously, HLA typing may be determined using methods including, but not limited to, DNA sequencing, microlymphocytotoxicity assays, or hybridization of DNA to oligonucleotide probes. For example, genomic DNA may be purified from the organism, amplified using polymerase chain reaction (PCR), and then sequenced to determine the HLA type of the organism. In another example, genomic DNA may be purified from an organism, amplified using PCR, and hybridized with sequence-specific probes. In some embodiments, the sequence-specific probes may be conjugated to a fluorochrome to enable detection of the duplex using chemiluminescence. In some embodiments, the HLA type of an individual organism is determined, and HLA proteins of the same type are recombinantly produced for use in the biological filter.

The antigen peptides are complexed with HLA proteins via the peptide-binding groove of HLA proteins. As used herein, the term "peptide-binding groove" generally refers to the region within an HLA protein that facilitates attachment of an antigen peptide. Antigen peptides of varying lengths may bind to the HLA protein. By way of example, the antigen peptide may include 8-10 amino acids or 13-18 amino acids.

Figure 9:
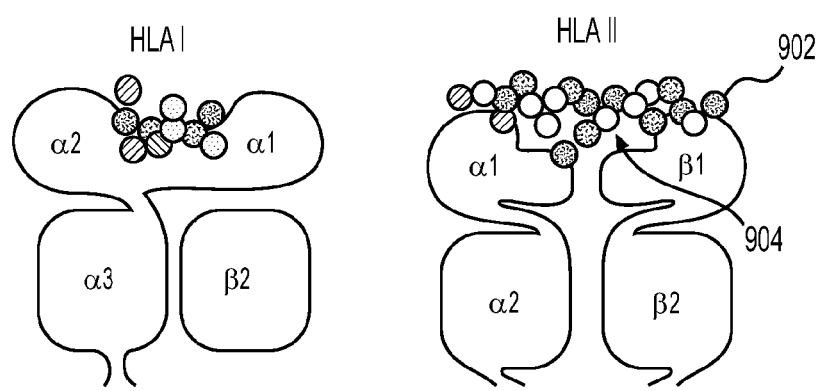
FIG. 9 schematically illustrates antigenic myelin peptides bound to HLA I and HLA II, respectively, consistent with embodiments of this disclosure.

By way of schematic representation, FIG. 9 illustrates HLA I and HLA II proteins bound to myelin-derived antigen peptides where myelin-derived antigen peptides 902 are illustrated adjacent the HLA peptide-binding grooves 904.

In some embodiments, HLA-peptide complexes may be recombinantly designed or may be obtained endogenously from an individual, such as a patient. In some embodiments, the HLA proteins include HLA I and/or HLA II. By way of example, the HLA proteins of the HLA-peptide complexes may be further modified, either genetically or in vitro. For example, the HLA protein may be truncated, which may result in a C-terminal cysteine. The HLA-peptide complex may react with maleimide or an analog thereof on the medium, thereby anchoring the HLA-peptide complex to the medium. In a preferred embodiment, the HLA-peptide complexes are disposed on the filter medium in a manner such that anchoring locations for the complexes are spaced from each other by at least a width of an HLA binding groove.

In certain embodiments, the filter may include a plurality of layers configured to permit fluid flow therebetween, as described previously and with reference to FIGS. 2A-2D. Portions of adjoining layers may contact each other or may be spaced apart from each other by, for example, scaffolding, as described above and depicted in FIG. 3.

Apparatus for Removing Pathogenic T-Cells from a Patient's Blood

Some aspects of the present disclosure may involve an apparatus for removing pathogenic T-cells from a patient's blood, such an apparatus that incorporates one or more biological filters as described above. The apparatus might be deployed in a medical facility, such as an outpatient clinic, similar in some respects to a kidney dialysis center, where patients can receive periodic extracorporeal blood treatments. In order to efficiently treat patients, these outpatient clinics may be equipped with apparatuses that can remove specific pathogenic T-cells. This procedure may occur, for example, using an apparatus that implements a two-stage process. Thus, various apparatuses may be provided, consistent with this disclosure, for removing pathogenic T-cells from a patient's blood. As described earlier, the pathogenic T-cells may be those that correlate to a specific disease. For example, "pathogenic T-cells" may be cells that cause diseases, disorders or other abnormal medical conditions, such as autoimmune diseases, cancers, and post-transplantation complications. A filter used in the apparatus may be designed to trap those specific pathogenic T-cells to remove them from the blood, thereby mitigating symptoms of the disease.

Figure 10:
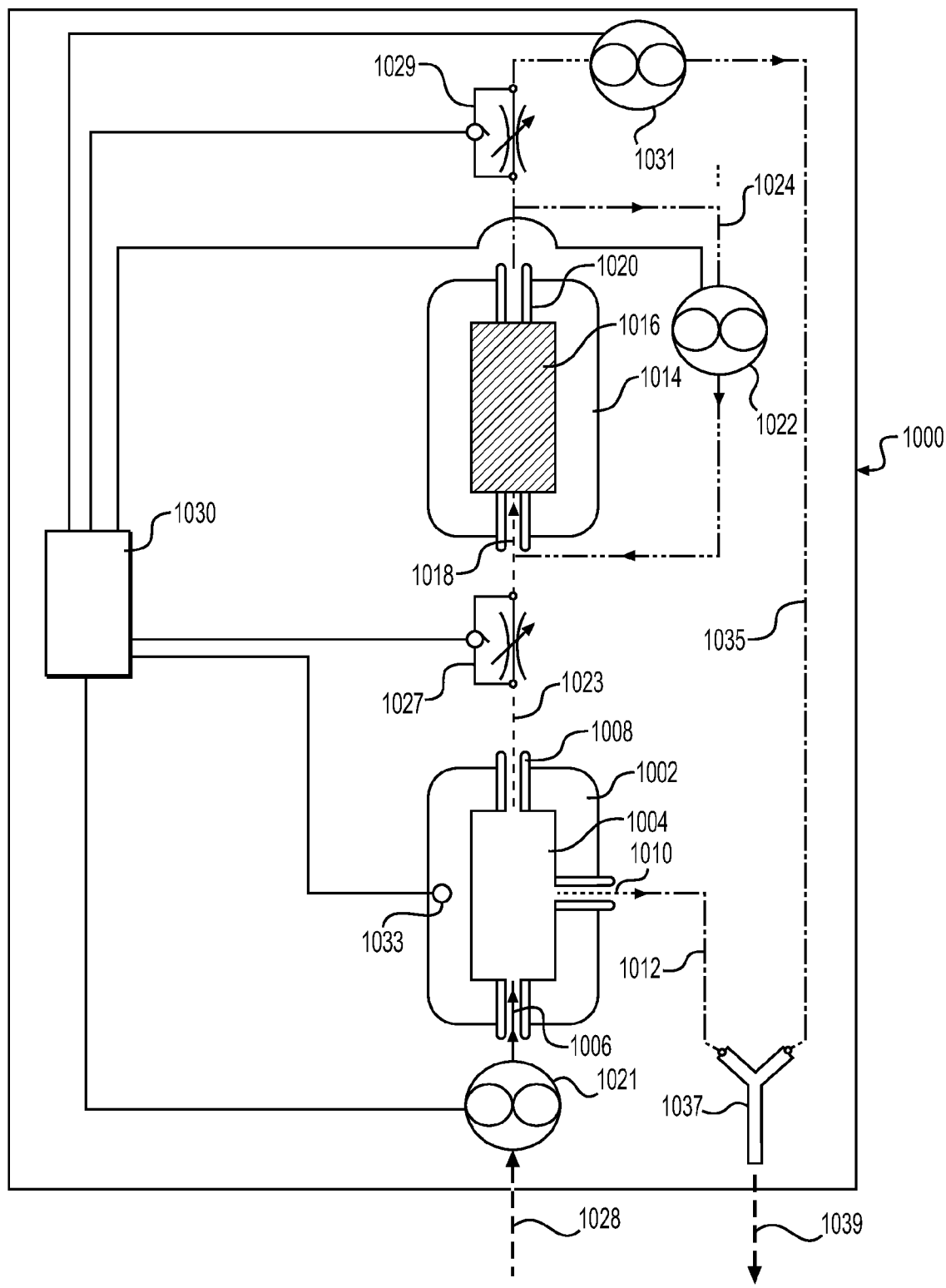
FIG. 10 is a schematic representation of an exemplary two-stage apparatus for removing pathogenic T-cells from a patient's blood, consistent with embodiments of this disclosure.

By way of a non-limiting example, FIG. 10 is a schematic representation of an apparatus 1000 for removing pathogenic T-cells from a patient's blood supplied by inlet conduit 1028. The inlet conduit 1028 may be directly connected to a patient via a needle or shunt in the patient. Alternatively, inlet conduit 1028 may be connected to a blood reservoir. The apparatus may have varying configurations depending on intended use and specific functional requirements.

According to some embodiments, such an apparatus may include a first stage region being configured to retain a blood separator capable of separating white blood cells from other fractions of whole blood, the blood separator having an inlet, a white blood cell outlet, and a blood fraction outlet configured to enable return of the other fractions to the patient. As used herein, the term "first stage region" refers to a portion of the apparatus associated with the separation of at least one fraction of blood from at least another fraction of blood, and more specifically, separating white blood cells from other fractions of whole blood. The separation may be achieved through a blood separator which may employ any mechanical, chemical or other means of achieving a division of blood constituents. That is, the separator is not limited to any particular principles so long as it is capable of separating white blood cells for later filtering.

In one example, the blood separator may be configured to facilitate an apheresis or other centrifugal function for mechanically causing blood to separate into at least two portions. Thus, the first stage may include components associated with rotating a blood container. These components may include a rotation assembly driven by a motor, and mechanical structure for grasping a blood container. The blood container itself may be part of a disposable tubing set.

The inlet of the blood separator may be a location where blood enters the stage. For example, it may be located in an area or structure configured to retain or contain a disposable tube for supplying whole blood to the first stage. Similarly, the white blood cell outlet and a blood fraction outlet may be respectively located in areas or structures configured to retain or contain disposable tubes for separately conveying white blood cells and other blood fractions out of the first region. As will be discussed later in greater detail, the white blood cells (or a fraction thereof containing T-cells) may proceed to filtering while the other blood fractions may be designated for return to the patient, either directly or via an intermediate collection chamber. While the first stage is discussed above in connection with a disposable tubing set, in some configurations the conduits and/or separator need not be disposable.

The exemplary apparatus 1000 of FIG. 10, may include a first stage region 1002, in which blood separator 1004 is located having inlet region 1006, which blood cell outlet region 1008, and blood fraction outlet region 1010. When a disposable tubing set is used, the upstream portion of fractional blood outlet conduit 1012 may pass through the blood fraction outlet section 1010 to return the blood fractions of blood (less the white blood cells) to the patient through the Y-junction 1037 to the 1039 outlet. This can occur through a flow connection to the vasculature of the patient or may occur by first storing the blood in a chamber before return to the patient. Similarly, the upstream end of white blood cell conduit 1023 may pass through the white blood cell outlet region 1008 for conveyance to a filtering stage.

Figure 11A:
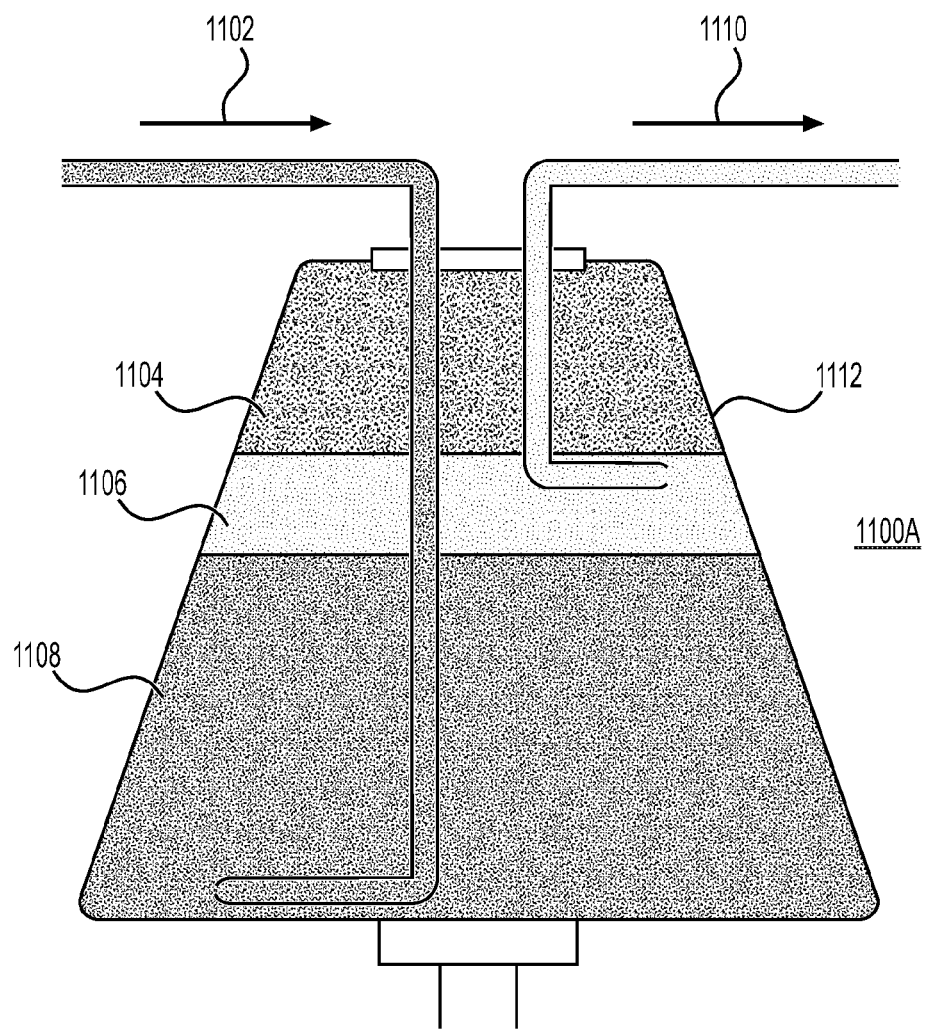
FIG. 11A is a schematic representation of an exemplary apheresis blood separator consistent with embodiments of this disclosure.

By way of example, blood separator 1004 may be configured to separate blood using apheresis, centrifugation, or filtration. In other words, the blood separator may be an apheresis system, a centrifugation system, or a filtration system, examples of each which are provided in FIGS. 11A-11O. In the exemplary apheresis system 1100A depicted in FIG. 11A, whole blood may enter a spinning container 1112 via inlet conduit 1102. and stratifies into plasma 1104, leukocytes or white blood cells 1106, and erythrocytes 1108. White blood cells 1106 may then be drawn off via outlet conduit 1110 which may connect to white blood cell outlet 1008 in FIG. 10 to supply white blood cells to the inlet region 1018 of blood filtration region 1014.

Figure 11B:
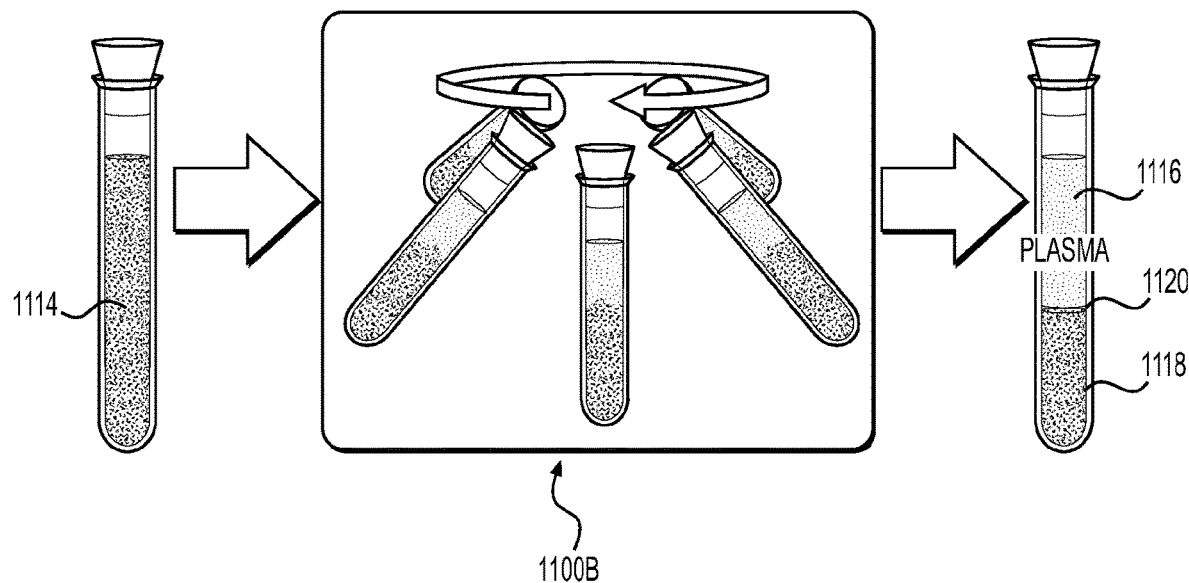
FIG. 11B illustrates an exemplary centrifugal blood separator consistent with embodiments of this disclosure.
Figure 11C:
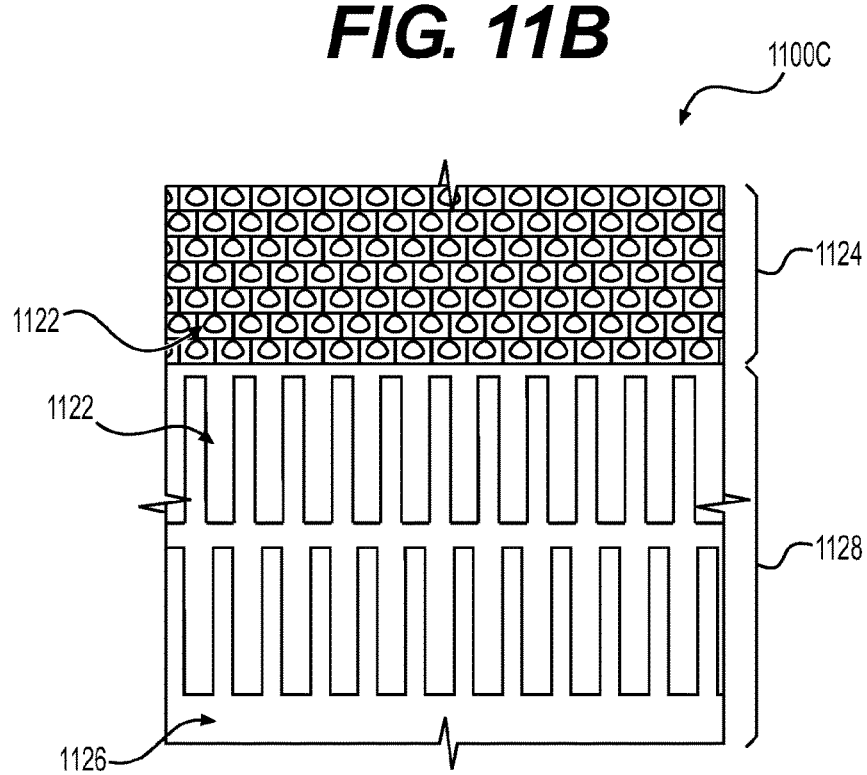
FIG. 11C illustrates an exemplary filtration blood separator consistent with embodiments of this disclosure.

In the exemplary centrifugation system 1100B depicted in FIG. 11B, centrifugal force is applied, similar to the prior apheresis embodiment, to separate the components of whole blood 1112 into plasma 1114, erythrocytes 1116, and leukocytes and platelets 1118. The exemplary filtration system 1100C depicted in FIG. 11C includes a plurality of cell capture structures 1124 and a plurality of filters 1128 that together separate whole blood cells 1122 and plasma 1126.

Consistent with some embodiments, a first pump may be provided for conveying blood from a patient through the first stage region. The first pump may be located upstream of an inlet area of the first stage in order to drive blood into the first stage region. Alternatively, the first pump may be downstream of the first stage for causing blood to enter the first stage through negative pressure. While any form of pump may be used, in a preferred embodiment the pump may be a peristaltic pump. By way of one example, peristaltic pump 1021 may be provided as illustrated in FIG. 10 for conveying blood from inlet conduit 1028 to first stage 1002.

Consistent with disclosed embodiments, there may be provided a second stage region configured to retain a biological filter including human leukocyte antigen (HLA)-peptide complexes and having at least one filter inlet area and at least one filter outlet area, and wherein the first stage region and the second stage region are oriented to enable flow from the white blood cell outlet region of the blood separator to the at least one inlet of the biological filter second stage region. As used herein, the term "second stage region" refers a portion of the apparatus associated with filtration. For example, the second stage region may be an area of the apparatus configured to retain a biological filter. A biological filter including human leukocyte antigen (HLA)-peptide complexes is described in greater detail herein and is therefore not repeated in the discussion of this embodiment. A filter retained in the second stage region has an inlet that flow-connects to the white blood cell outlet of the first stage. Since T-cells are contained in the white blood cell fraction, this configuration may maximize the effectiveness of the filter, obviating the need to introduce other fractions of blood into the filter when those other fractions are known not to contain the targets of filtration. Non-white blood cell fractions may make their way to the filter, and if this happens, the system would still perform, but to a lesser degree of efficiency.

By way of one example, FIG. 10 illustrates second stage region 1014 configured to retain a biological filter 1016 including human leukocyte antigen (HLA)-peptide complexes and having at least one inlet 1018 and at least one outlet 1020. The first stage region 1002 and the second stage region 1014 are oriented to enable flow from the white blood cell outlet 1008 of the blood separator 1004 to the inlet 1018 of the biological filter 1016. All embodiments of the biological filter and the HLA-peptide complexes as described herein are suitable for use in the second stage region 1014. The same principles described herein with respect to filtering T-cells may be applied to the filtration of other biological materials and is to be considered within the scope of this disclosure.

In one embodiment, the biological filter may include a plurality of layers, such as the layers depicted in FIG. 3, as well as other embodiments of multi-layered biological filters as described herein, such as FIGS. 2A-2D. Each layer of the biological filter may include human leukocyte antigen (HLA)-peptide complexes thereon, as the greater the surface area exposed to the complexes, the more efficient the filter. In one embodiment, the biological filter 1016 may be configured to selectively bind pathogenic T-cells, such as disease-specific pathogenic T-cells. To "selectively bind" means that in order for a specific T-cell with a specific T-cell receptor to identify its target peptide (epitope), the peptide has to be bound to an HLA protein. For instance, the biological filter 1016 may include human leukocyte antigen (HLA)-peptide complexes where the peptides in the complexes are antigen peptides that may be associated with a variety of diseases, such as multiple sclerosis. Antigen peptides associated with multiple sclerosis may be derived from the exemplary proteins described previously. Examples of the antigen peptide have also been described previously.

Consistent with disclosed embodiments there may be provided a second pump for recirculating white blood cells from the at least one outlet of the biological filter to the at least one inlet of the biological filter. The function of the second pump is to provide the white blood cells with an ability to make multiple passes through the biological filter 1016. With each pass, more pathogenic T-cells will bind to the filter. The recirculation may continue for a period of time sufficient to remove enough pathogenic T-cells to accomplish the design specifications of the system, which itself may depend on the type of filter and the treatment parameters for a particular patient.

By way of example, apparatus 1000 in FIG. 10 may include second pump 1022 for recirculating white blood cells from the outlet 1020 of the biological filter to the inlet 1018 of the biological filter. As with the first pump 1021, the second pump 1022 may also be a peristaltic pump. In order to enable recirculation, electronically controllable valves 1027 and 1029 may be capable of isolating filter 1016 so that activation of pump 1022 causes recirculation. The values 1027 and 1029 may be regulated by controller 1030, as will be discussed later in greater detail.

In a particular embodiment, the second stage region 1014 is sized so that the biological filter 1016 may contain about 3-50 ml of the white blood cell fraction. The apparatus of FIG. 10 may permit blood to be processed in batches. After a batch of white blood cells pass from the first stage to the second stage, flow might be restricted to the second stage until batch processing in the second stage is completed, as will be discussed later in greater detail.

Consistent with disclosed embodiments there may be provided a plurality of electronically controllable valves for directing blood through the first stage region and the second stage region. An electronically controllable valve may include any device that regulates the flow of fluid in response to an electrical signal. Thus, "a plurality of electrically controllable valves" refers two or more electrically controllable valves that each regulate, direct, or control the flow of the patient's whole blood, white blood cells, non-pathogenic white blood cells, and/or other fractions of whole blood (i.e., plasma, erythrocytes). For example, while the biological filter 1016 is doing its work, one or more valves may be used to prevent additional white blood cells from entering the filter. While recirculation through the biological filter is not required in all embodiments, when recirculation is employed, valves may be used to isolate the filter, permitting white blood cells to recirculate.

With reference to the example of FIG. 10, the apparatus 1000 may include valves 1027 and 1029, as previously discussed. Similarly, peristaltic pump 1021, when deactivated, may effectively serve as a valve.

Disclosed embodiments may include at least one processor. "At least one processor" may constitute any physical device or group of devices having electric circuitry that performs a logic operation on an input or inputs. For example, the at least one processor may include one or more integrated circuits (IC), including application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations. The instructions executed by at least one processor may, for example, be pre-loaded into a memory integrated with or embedded into the controller or may be stored in a separate memory. The memory may include a Random Access Memory (RAM), a Read-Only Memory (ROM), a hard disk, an optical disk, a magnetic medium, a flash memory, other permanent, fixed, or volatile memory, or any other mechanism capable of storing instructions. In some embodiments, the at least one processor may include more than one processor. Each processor may have a similar construction, or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact. By way of example, in FIG. 10, processor 1030 is illustrated. Although illustrated schematically as a single block, processor 1030 may include a single processor or a plurality of processors co-located or spread across multiple locations within the apparatus, 1000. Additionally, some or all processing functions may be performed remote from apparatus 1000, such as locations accessible via a communications network.

Consistent with some embodiments, the at least one processor may be configured to control the first pump to cause blood to flow through the first stage region until a quantity of white blood cells are separated and conveyed to the second stage region. The at least one processor may be configured to control components such as pumps and valves by sending electronic signals to the pumps and valves. Those signals may be sent by the at least one processor in order to cause the apparatus to comply with a treatment protocol. For example, at least one processor may send an activation signal to a pump to cause blood to enter the first stage for separation and enabling separated white blood cells to flow to a second stage for filtering.

By way of one example illustrated in FIG. 10, processor 1030 may be configured to control the first pump 1021 to cause blood to flow through the first stage region 1002 until a quantity of white blood cells is separated and conveyed to the second stage region 1014. The processor 1030 may also control blood separator 1004 to cause the separation to occur. For example, if blood separator 1004 is associated with a motor (not illustrated) for turning a centrifugal separation chamber or compartment, processor 1030 may control that motor. As the blood separates, the white blood cells may exit white blood cell outlet region 1008 and enter biological filter 1016 via conduit 1023. An electronically controllable valve 1027 may be located in the path of conduit 1023 for regulating the flow of white blood cells into and out of second stage region 1014. The force of pump 1021 may cause white blood cells to flow through white blood cell conduit 1023. Alternatively or additionally, another pump (not shown) may be located in white blood cell conduit 1023 to facilitate white blood cell flow to the second stage region 1014.

In some disclosed embodiments the at least one processor may be configured to deactivate the first pump when the quantity of white blood cells is separated and conveyed to the second stage region. Deactivation of the first pump may occur because the biological filter in the second stage may have limited capacity for filtering. As such, the biological filtering may occur in batches, where, during filtering of any given batch, additional new white blood cells are not introduced into the biological filter. To accomplish this, once the biological filter in the second stage is at capacity, the processor may deactivate a pump (or close a valve) supplying the biological filter with additional white blood cells. This may also occur by closing a valve on an inlet side of the biological filter to prevent additional white blood cells from entering the filter. The processor may limit the quantity of white blood cells entering the biological filter based on a program run by the processor. That program might rely, for example, on feedback from the system such as flow or quantity sensors. For example, a flow sensor may determine when a volume of white blood cells passing to the second stage is within a target parameter for the filter. Or, a volume sensor in the first stage or the second stage may detect when a volume of separated white blood cells reaches a target parameter.

In some alternative variations, the pump supplying the first stage may continue to operate along with the blood separator, even after capacity is reached in the biological filter in the second stage region. In such variations, the pump may continue to run in order to prepare a next batch of white blood cells for supply to the biological filter. Therefore, deactivation of the pump need not occur simultaneously with the beginning of batch filtering in the second stage. Moreover, a buffering reservoir (not shown) for white blood cells may hold separated white blood cells readied for filtering. The second stage may be supplied with white blood cells via the buffering reservoir. At some point, either simultaneously with the beginning of filtering of a new batch, while a batch is being filtered, or during the last batch of filtering, the pump supplying the first stage may be deactivated by the at least one processor although filtering in the second stage is ongoing.

By way of one example illustrated in FIG. 10, processor 1030 may deactivate first pump 1021 after the quantity of white blood cells separated by blood separator 1004 coincides with either a capacity of the biological filter 1016, or meets an operational parameter of the system. This may be detected, for example, by sensor 1033 associated with first stage 1002. Sensor 1033 may detect a volume of collected white blood cells (or relevant fraction thereof) in blood separator 1004 or an amount of white blood cells that have exited blood separator 1004. When the quantity meets a system parameter, further white blood cell flow to the biological filter 1016 may be restricted. As mentioned above, pump 1021 may continue to run during at least some of the time when filtering simultaneously occurs in second stage 1014. If pump 1021 continues to run during filtering, processor 1030 may be programmed to close valve 1027 in order to prevent white blood cell from entering the biological filter 1016.

In some embodiments, the at least one processor may be configured to activate the second pump and control a plurality of valves to recirculate the quantity of white blood cells through the biological filter for a sufficient time to separate the pathogenic T-cells from non-pathogenic white blood cells. Particularly when a system is designed for use with a filter requiring multiple white blood cell passes, in order to remove a sufficient quantity of pathogenic T-cells, a bypass loop may be provided to recirculate white blood cells through the filter. This may occur by including a valve on either side of the second stage and proving a pump in the bypass loop that circulates white blood cells from an outlet of the biological filter to an inlet of the biological filter. A valve, as used herein can be a traditional valve, or it can be any structure that prevents flow. In some instances, an inactive pump can be considered a valve for this purpose, if flow is restricted through the inactive pump. The at least one processor may be programmed to keep the valves surrounding the biological filter closed and the recirculating pump running for a period consistent with the particular use case or design parameter. For example, the recirculation time may be a function of the size/capacity of the filter, the amount of desired filtering, and the state of the filter. For example, as a filter ages, more recirculation may be necessary to achieve a desired target. The processor may keep track of a quantity of white blood cells already filtered or an amount of time a filter was used, and may increase a recirculation time as a function of either of these parameters or any other parameter indicating the health of the filter.

As illustrated in the example of FIG. 10, processor 1030 may be configured to control valve 1027 and 1029, respectively upstream and downstream of biological filter 1016. When both of those valves are closed and pump 1022 is activated by processor 1030, white blood cells are caused to recirculate through biological filter 1016. If valve 1029 is omitted, pump 1031 may be considered a valve as it prevents flow passage. Similarly, valve 1027 could be replaced with a pump that would likewise constitute a valve when the pump is deactivated.

The at least one processor may also be configured to return the non-pathogenic white blood cells to the patient. This may occur directly by evacuating the biological filter to a tubing set connected to the arterio-venous system of a patient, or may occur indirectly by supplying the filtered white blood cells to a container from which the white blood cells may be later returned to the patient.

Return of non-pathogenic white blood cells may occur, by way of example, using the apparatus of FIG. 10. After complying with a recirculation program implemented by processor 1030, valve 1029 may be opened and pump 1031 activated to evacuate filtered white blood cells from biological filter 1016. Pump 1031 may be a peristaltic pump that delivers treated white blood cells back to the patient via treated white blood cell conduit 1035. In order to minimize the number of skin-puncturing needles or other cannulas required, a Y-junction 1037 may be employed so that both the blood fraction conveyed by fractional blood outlet conduit 1012 and the filtered white blood cells conveyed by conduit 1035 may return to the patient through a single vein.

Disclosed embodiments may include at least one valve controllable by the at least one processor to prevent white blood cells from being returned to the patient while the second pump is activated to recirculate the quantity of white blood cells through the biological filter of the second stage. Any valve or other structure that acts as a valve may be used to prevent return of white blood cells to the patient during recirculation. By way of example, valve 1029 may be closed by controller 1030 to prevent white blood cell return to the patient during recirculation of white blood cells through biological filter 1016.

Some embodiments may include at least one valve controllable by the at least one processor to prevent white blood cells from traveling from the first stage region to the second stage region while the second pump is activated to recirculate the quantity of white blood cells through the biological filter of the second stage. As discussed earlier, when a batch of white blood cells is being filtered in the second stage, it may be preferable to restrict further addition of white blood cells from entering biological filter 1016. This may be particularly preferable if the biological filter is already at its volume capacity. Any structure that restricts flow to the second stage region may be considered a valve. By way of example, valve 1027 in white blood cell conduit 1023 is one such structure that when closed by processor 1030, prevents white blood cells from traveling to the second stage region. Similarly, a pump (not shown) in the path of white blood cell conduit 1023 might also act as a valve if deactivated by processor 1030.

Additionally according to some embodiments of this disclosure at least one processor may be configured to control the plurality of electrically controllable valves to cause white blood cells to be processed in batches in the second stage region, to permit a first batch of white blood cells to recirculate in the second stage region and thereafter be returned to the patient before the at least one processor permits a second batch of white blood cells to enter the biological filter of the second stage. As previously discussed, this batch process may be advantageous when a filter is used that is incapable of sufficiently removing pathogenic T-cells in a single pass through the filter. By including a bypass from an outlet of the filter to an inlet of the filter, white blood cells can make multiple passes through the filter, increasing removal of pathogenic T-cells. This may be facilitated in the example of FIG. 10 by controller 1030 configured to close, during a recirculation process, valves 1027 and 1029, and to activate recirculation pump 1022. Following sufficient recirculation, which could be timed by processor 1030, valve 1029 may be opened and pump 1031 activated to return the batch of filtered white blood cells to the patient. Then, processor 1030 might open valve 1027 and activate either pump 1021 or another pump (not shown) in the path of white blood cell conduit 1023, to introduce additional white blood cells into the second stage region 1014. Prior to a batch being released from the second stage, processor 1030 might anticipate the need for more separated white blood cells and might activate pump 1021 and a mechanism associated with blood separator 1004 so that separated white blood cells are ready for transfer to biological filter 1016 once the biological filter 1016 is evacuated of a prior batch of white blood cells. In some embodiments the at least one processor may be configured to control at least one valve to add erythrocytes and saline before returning the other fractions of whole blood to the patient. This may occur through connection of the apparatus to one or more reservoirs (not shown) for supplying erythrocytes and/or saline to the blood fractions. For example, in FIG. 10, a controllable valve might be included in the path of fractional blood outlet conduit 1012 which might be connected to one or more reservoirs (not illustrated). Controller 1030 might regulate the added valves to introduce erythrocytes and/or saline to fractional blood outlet conduit 1012 (or some other location) for delivery to the patient with the returning whole blood fractions.

Similarly, the at least one processor may be configured to control at least one valve to supply anticoagulant to the second stage region. Anticoagulants may be beneficial to prevent clot formation during the recirculation process. By way of example, an anticoagulant reservoir (not shown) might be located in flow connection with conduits 1023 or 1024, with a metering valve (not shown) controlled by processor 1030.

Some disclosed embodiments may further includes a blood blending device and wherein the at least one processor is configured to control the blood blending device to blend the other fractions of whole blood and/or the non-pathogenic white blood cells prior to returning to the patient. Examples of blood blending devices include mixers, such as vortex mixers, that gently shake or agitate the other fractions of whole blood and/or the non-pathogenic white blood cells without disrupting any components or cells contained therein. Such a device may be included downstream of Y-junction 1037 or may replace Y-Junction 1037 in the example of FIG. 10. In yet another example, disclosed embodiments may include an arterial blood pressure control unit (not illustrated). Such a device may be used to ensure proper regulation of pressure as blood or its components is returned to the patient. It too may be located on the downstream end of the system, proximate Y-junction 1037 in FIG. 10, and may be controlled by the processor 1030.

Disclosed embodiments may also include a tubing set for use in removing pathogenic T-cells from a patient's blood. Such a tubing set may be disposable and may include tubing segments and other disposable components. Alternatively, the tubing set or portions thereof such as the biological filter, may be reusable with the same patient. The tubing set may include one or more of a first stage region including a blood separator, a white blood cell outlet, and a blood fraction outlet. The tubing set may also include a second stage region including a biological filter containing human leukocyte antigen (HLA)-peptide complexes and having at least one primary inlet, at least one primary outlet, at least one recirculation inlet, and at least one recirculation outlet. A recirculation loop in the tubing set may interconnect the at least one recirculation outlet with the recirculation inlet. At least one blood withdrawal tube may be configured to convey blood from the patient to the at least one inlet of the first stage region. At least one intermediate tube may be configured for conveying blood from the white blood cell outlet of the first stage region to the primary inlet of the second stage region. At least one first stage bypass tube may convey a blood fraction from the blood fraction outlet of the first stage region for return to the patient. And at least one white cell return tube may be configured for conveying white blood cells from the primary outlet of the second stage region for return to the patient.

Figure 12A:
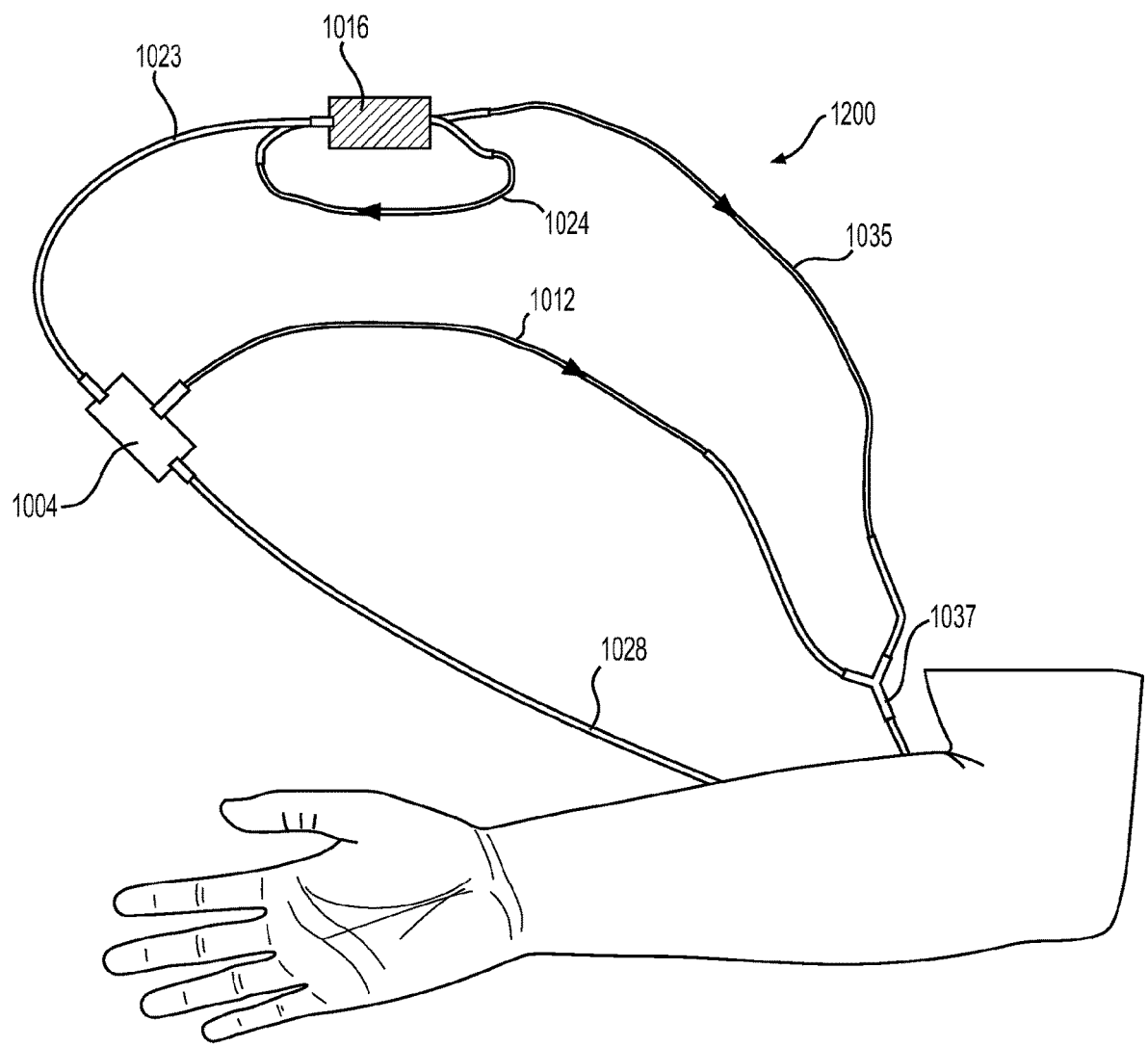
FIG. 12A schematically illustrates an exemplary two-stage tubing set for removing pathogenic T-cells from a patient's blood, consistent with embodiments of this disclosure.

FIG. 12A provides one example of a tubing set 1200 for use in removing pathogenic T-cells from a patient's blood. For consistency, like components in FIG. 10 share the same reference numerals. The tubing set 1200 may include a blood separator 1004 and a biological filter 1016, connected in the following manner. An inlet conduit 1028 connects an inlet of blood separator 1004. On an opposite distal end of inlet conduit 1028 there may be disposed some form of connector (not shown) for connecting the inlet conduit to a source of blood. In one embodiment that connector may be a needle; in another it may be a luer connector or any other type of connector or cannula for collecting blood from a reservoir or a patient. The blood separator may have at least two outlets, one for white blood cells and at least one other fractional blood outlet. A fractional blood outlet conduit 1012 is connected to the fractional blood outlet for return of the blood fractions to the patient. An area of the tubing set containing the blood separator 1004 may be considered a first stage region of the tubing set. White blood cell conduit 1023 is connected to an inlet of biological blood filter 1016, and a recirculation loop 1024 connects an outlet of the biological filter 1016 with the inlet of the same filter. A treated white blood cell conduit 1035 is connected to an outlet of the biological blood filter for returning the treated white blood cells to a patient. An area of the tubing set containing the biological filter 1016 may be considered a second stage region of the tubing set.

Conduits 1035 and 1012, like conduit 1028 may include one of the same type of connectors/needles/cannulas as previously described for returning blood components directly to the patient or to a reservoir for indirect return to the patient. Alternatively, as illustrated in FIG. 12A, conduits 1012 and 1035 may be connected to a Y-junction 1037 which connects on an outlet end of the Y-junction 1037 to a connector as previously described.

The conduits of the tubing set may be made of flexible plastic and may be sized so that the tubes may fit within the races of peristaltic pumps employed in an apparatus for treating blood.

Figure 12B:
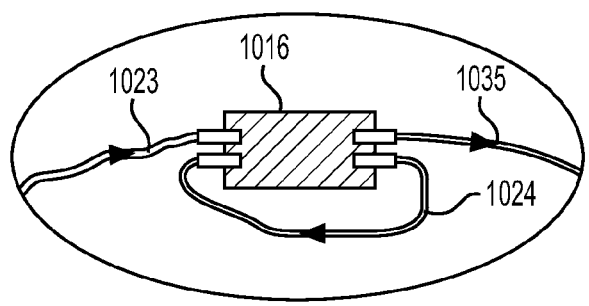
FIG. 12B schematically illustrates an exemplary second stage region of a two-stage tubing set, consistent with embodiments of this disclosure.
Figure 12C:
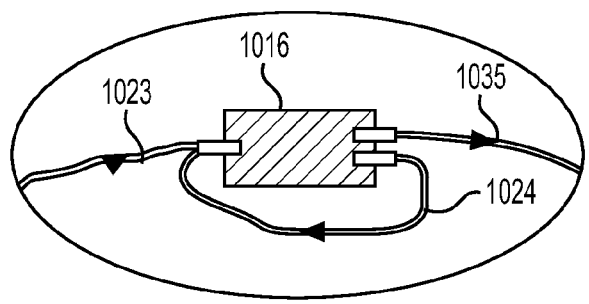
FIG. 12C schematically illustrates an exemplary second stage region of a two-stage tubing set, consistent with embodiments of this disclosure.
Figure 12D:
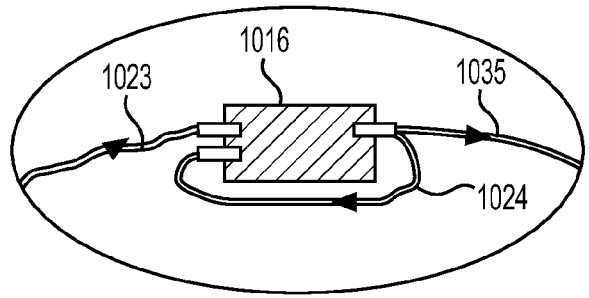
FIG. 12D schematically illustrates an exemplary second stage region of a two-stage tubing set, consistent with embodiments of this disclosure.

The illustration of FIG. 12A is but one example, and variations are contemplated within this disclosure. The primary inlet of the biological filter (i.e., of the second stage region) and the recirculation inlet may be common. For example, in FIG. 12B, a pair of inlet conduits and a pair of outlet conduits share common filter inlets and outlets, respectively. It is to be understood that each conduit might be connected at a unique inlet or might be connected to a junction that feeds a single inlet. Alternative exemplary variations of biological filter connections are illustrated in FIGS. 12B-12D.

Only a single biological filter is illustrated in FIG. 10. It is contemplated that two or more filters might be employed to speed the treatment process. In a multiple filter embodiment, a single blood separator might supply two or more filters. Alternatively, multiple blood separators might be employed. In the case of multiple filters connected to a single blood separator, multiple white blood cell conduits like 1023 might supply the multiple filters. In that embodiment, an associated treatment apparatus might include a valving system for controlling the flow of blood to each of the biological filters. That valving system might include a separate controllable valve on each white blood cell conduit, each valve being controlled by processor 1030.

Regardless of embodiment, the length of each conduit may be sized to enable the blood separator 1004 and the biological blood filter 1016 to assume preassigned positions in their respective first stage regions and second stage regions on an associated apparatus with enough conduit length to fit within interposed peristaltic pumps, such as pumps 1021, 1022, and 1031 of FIG. 10.

System for Predictively Adjusting a Treatment Regimen for a Patient with T-Cell Associated Immunological Disorder The present disclosure contemplates preventive measures whereby T-cells that may become pathogenic in the future can be predicted and prophylactically removed, for example, by using a biological filter described herein. To this end, the present disclosure provides a system for predictively adjusting a treatment regimen for a patient with a T-cell associated immunological disease. Once the T-cells that may become pathogenic are identified, a patient who is already being treated for a disease can have his or her treatment regimen adjusted accordingly so that the future progression of the disease can be arrested before its development. While the present disclosure provides examples of adjusting treatment regimens of T-cell associated immunological diseases, it should be noted that the aspects of the disclosure in their broadest sense are not limited to T-cell associated immunological diseases. Rather, the foregoing principles may be applied to treat other diseases as well.

The term "system" according to the present disclosure may include any device or group of devices that contain at least one processor capable of accessing and processing data. In a broadest sense, a system may be characterized by a processor. Or, a system may have multiple components. For example, a system may be a suitably programmed computer, the computer including at least a processing unit and a memory unit. One or more computer programs can be loaded into the memory unit and can be executed by the processing unit. The loaded program(s) may cause the computer to execute commands. The present disclosure further contemplates a machine-readable memory tangibly embodying a program of instructions executable by the machine for executing one or more methods of this disclosure. For example, a computer program product may be embodied in a non-transitory computer-readable medium and executable by at least one processor, the computer program product including instructions for causing the at least one processor to execute the commands. The present disclosure also contemplates a system where a suitably programmed computer may be connected to one or more input devices and/or one or more output devices. An exemplary system may include a computer that is connected to a flow cytometer or a system incorporating the same that counts, sorts, and detects cells such as T-cells; a protein chromatography system such as a liquid chromatography system that isolates HLA, antigen peptides, and/or HLA-peptide complexes from a biological fluid; and/or a system that detects and measures and detects binding of T-cells and HLA-peptide complexes in a patient such as fluorescence anisotropy, ITC, light scattering techniques or a suitable absorption spectroscopic system. Exemplary output devices that may be connected to a system of this disclosure include one or more of a display the may be useful in providing a notification to a medical professional of a possible disease progression, a transmitter capable of transmitting such a notification over a network, an interface for outputting instructions for making a customized filter for a patient, or a 3D printer or other machine for manufacturing biological filters.

The system may be configured to adjust a treatment regimen. A "treatment regimen" may include any course of medical treatment. For example, a biological filter may be selected or custom-designed in connection with a treatment regimen for removing a certain type of T-cells from a patient. An adjustment to a treatment regimen might involve changing one or more of the number of T-cells targeted for removal or the type of T-cell targeted for removal. Such adjustments may be made predictively as discussed later in greater detail. By way of another example, a treatment regimen may involve a defined duration, dosage, route of administration (e.g., oral, intra-venous, etc.) and/or one or more therapeutic agents or devices designed to cure a disease, and/or manage or alleviate its symptoms so as to improve the health of a patient. For instance, a treatment regimen may include a pharmaceutical drug taken orally, which may entail specific dosages of the active ingredient in the oral composition (e.g., tablet, capsule, solution) at specific frequencies (e.g., every 8 hours, every 12 hours), for specific durations (e.g., 6 weeks, 12 weeks), and with specific conditions when a patient is administered the drug (e.g., fed state, fast state). The foregoing regimen examples are provided for illustration only, and they may or may not be mutually exclusive.

According to some disclosed embodiments, a system may include at least one processor. The term "at least one processor" is as defined previously, which may include any physical device or group of devices having electric circuitry that performs a logic operation on an input or inputs. In some embodiments, the at least one processor may include more than one processor. As described previously, each processor may have a similar construction, or the processors may be of differing constructions that are electrically connected or disconnected from each other and may be separate circuits or integrated in a single circuit. When more than one processor is used, the processors may be configured to operate independently or collaboratively, may be co-located or located remote from each other, and may be coupled electrically, magnetically, optically, acoustically, mechanically or by other means that permit them to interact.

Figure 13:
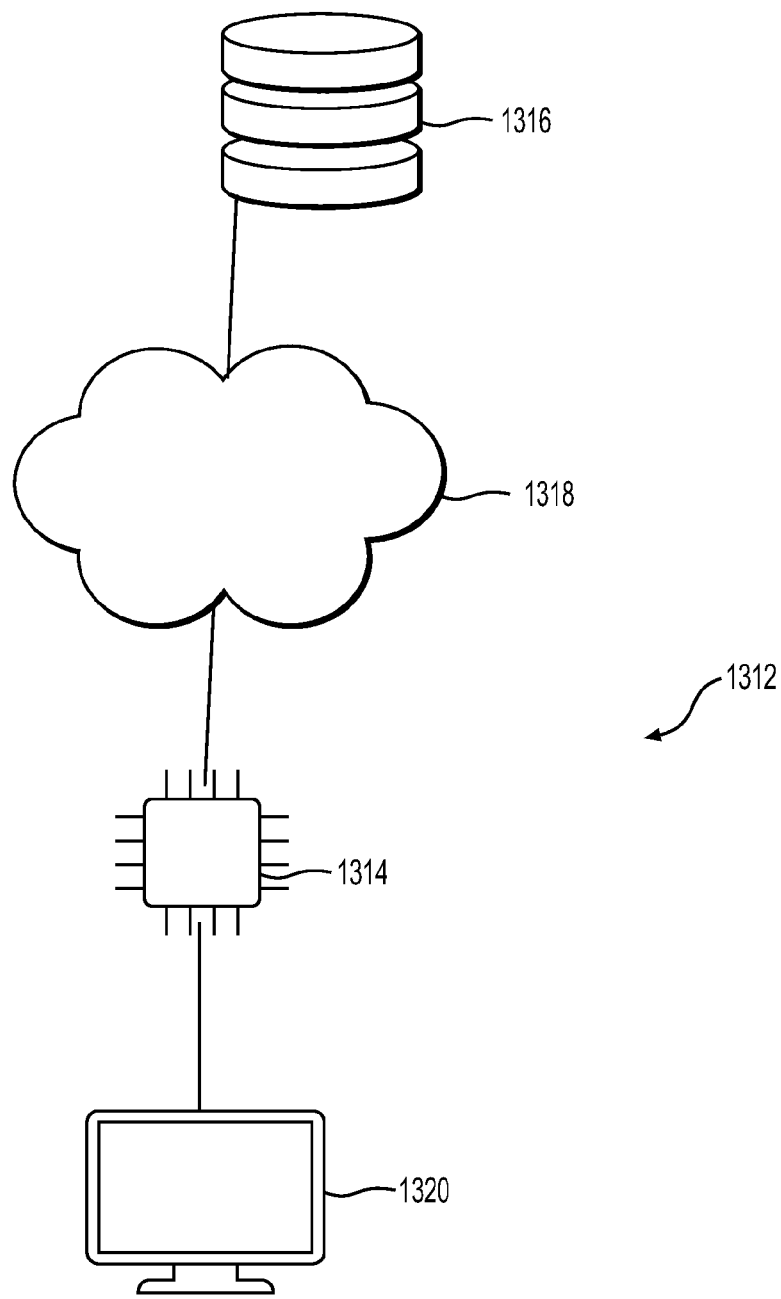
FIG. 13 is a schematic diagram of a system that may be used to implement methods consistent with some embodiments of this disclosure.

By way of example, FIG. 13 illustrates a system 1312, having at least one processor 1314. Although illustrated schematically as a single block, processor 1314 may include a single processor or a plurality of processors co-located or spread across multiple locations within the system, 1312. Processor 1314 may be connected to one or more servers 1316 via a network 1318. Alternatively or additionally, processor 1314 may be connected to a data storage device or memory (not shown) on the processor side of network 1318. In such situations, server 1316 may not be required as part of the system or may be augmented with local memory. Some or all processing functions may be performed remote from the at least one processor 1314 or even remote from system 1312.

Consistent with the disclosed embodiments, at least one processor may be configured to receive first data associated with treatment of a plurality of patients sharing a common HLA and common peptides triggering activation of disease-related T-cells. First data may include for example, information about certain pattern of how a disease progressed in patients sharing common HLA and common peptides triggering activation of disease-related T-cells. Additionally or alternatively, first data may include information about how patients sharing such commonalities reacted to one or more treatment regimens. For example, the first data might reflect likelihoods that patients sharing commonalities are likely to have had previously inactivated T-cells become activated over the course of a treatment or over a disease progression. And first data might include information on treatments that were effective in removing the T-cells likely to become activated. Further, first data may include probabilities and/or information from which probabilities of certain disease progressions in certain patients may be ascertained. First data may also include other patient-related information about the plurality of patients such as genetic information, information about current or prior diseases or conditions, or any other health or biologically-related information. The "first data associated with treatment" may involve information related to effects of a current treatment regimen on a medical condition, such as changes in symptoms experienced by the patient, changes in blood chemistry, or any other biological effect.

Figure 14:
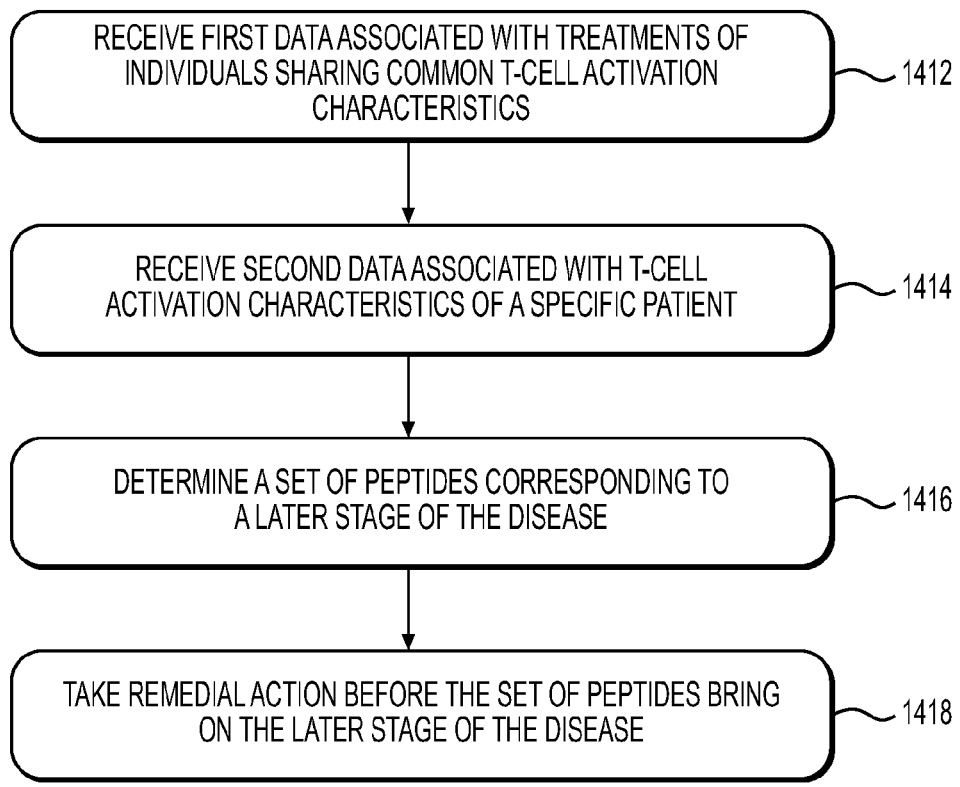
FIG. 14 is a block diagram of an exemplary proactive treatment method consistent with the present disclosure.

By way of one example, first data may be received as reflected in block 1412 of FIG. 14. First data may be stored on one or more servers 1416 as illustrated in FIG. 13, and/or may be stored in a data structure. A data structure consistent with the present disclosure may include any collection of data values and relationships among them. The data may be stored linearly, horizontally, hierarchically, relationally, non-relationally, uni-dimensionally, multi-dimensionally, operationally, in an ordered manner, in an unordered manner, in an object-oriented manner, in a centralized manner, in a decentralized manner, in a distributed manner, in a custom manner, or in any manner enabling data access. By way of non-limiting examples, data structures may include an array, an associative array, a linked list, a binary tree, a balanced tree, a heap, a stack, a queue, a set, a hash table, a record, a tagged union, ER model, and a graph. For example, a data structure may include an XML database, an RDBMS database, an SQL database or NoSQL alternatives for data storage/search such as, for example, MongoDB, Redis, Couchbase, Datastax Enterprise Graph, Elastic Search, Splunk, Solr, Cassandra, Amazon DynamoDB, Scylla, HBase, and Neo4J. A data structure may be a component of the disclosed system or a remote computing component (e.g., a cloud-based data structure). Data in the data structure may be stored in contiguous or non-contiguous memory. Moreover, a data structure, as used herein, does not require information to be co-located. It may be distributed across multiple servers, for example, that may be owned or operated by the same or different entities. Thus, the term "data structure" as used herein in the singular is inclusive of plural data structures.

Storing the first data in one or more network accessible servers such as servers 1416 may enable first items of the first data to be aggregated from many sources via the Internet, for example, when network 1418 includes the Internet. As the amount of first data from differing patients grows, the predictive accuracy of the system is likely to increase. Alternatively, first data may be stored locally, in a memory device particularly associated with processor 1414. Regardless of where first data is stored, it may be received by processor 1414 which may perform functions discussed herein in greater detail.

A "plurality of patients sharing a common HLA and common peptides triggering activation of disease-related T-cells" may refer to a population of patients from whose data predictions may be made (e.g., less than or equal to about 10, about 20, about 50, about 100, about 500, about 1000, about 5000, about 10,000, about 25,000, about 50,000, about 75,000, about 100,000, etc. and including any integer between 10 and 100,000 or more), usually suffering from the same T-cell associated immunological disease or same category thereof, whereby upon encounter between the specific T-cell (and its unique T-cell receptor) with a corresponding peptide as presented by an HLA-peptide complex (from any type, from any cell origin), a series of biochemical cascade takes place, leading the T-cell to become activated and able to execute protection or immune attack against a specific target (peptide), which includes an aberrant immune response such as an autoimmune response.

Consistent with disclosed embodiments, data may include a progression of common peptides that activate the T-cells over time, in that at a later progression of a disease, a greater number of different peptides activates the disease-related T-cells than at an earlier time. For example, in initial stages of a disease's progression, a smaller group of peptides may activate T-cells that trigger a disease. Over time however, the list of peptides that activate T-cells that trigger the disease may change or grow. Such a progression may not be unique to a particular patient but may be exhibited across a group of patients who have a progression of disease-triggering peptides common to the group. The data received may include such information. Thus, a system in accordance with the present disclosure may aim to remedy a treatment regimen that may not effectively treat the disease in a patient because the disease changes over its progression such that pathogenic T-cells may later be activated by different or additional peptides. In such circumstances, the data associated with treatment may include information regarding the peptides that are common to the plurality of patients and activate the patients' disease-related pathogenic T-cells at one or more different stages of the disease. The plurality of patients sharing the common HLA and common peptides activating the disease-related T-cells may be individuals who each not only share the same disease, but also share the same or similar peptides that activate the T-call causing the disease.

In some embodiments, at least one processor that may be configured to receive second data associated with a particular patient with the common HLA and the common peptides and who is at a stage of the disease where a first set of peptides activates a first subpopulation of the disease-related T-cells and a second set of peptides does not activate a second subpopulation of the disease-related T-cells. Receiving the second data may include accessing data about a specific patient. The specific patient may be the subject of a treatment, and a medical professional may be interested in determining whether, in the future the specific patient may be subject to a disease progression where certain peptides not currently activating T-cells may do so as the result of a progression of the disease. The second data may include, for example, information characterizing the peptides currently triggering the disease in the specific patient. Or, if the specific patient is not yet exhibiting symptoms of the disease, the second data may include information about peptides expected to activate the specific patient's T-cells. Alternatively or additionally, the second data may include information about the specific patient's HLA type or any other biological or health information that might correlate to the disease.

By way of example, as depicted at block 1414 of FIG. 14, second data may be received, the second data associated with T-cell activation characteristics of a specific patient. In the exemplary embodiment of FIG. 13, the second data may be received by processor 1314. Such receipt may occur when a medical professional enters the data into memory for access by processor 1314 or may occur as the result of data imported over a network. The second data may include information received from analytical medical equipment used to characterize a patient's medical condition. This may occur for example, via a data connection between processor 1314 and the medical equipment (not shown). In some embodiments, the second data may include various types of data received by processor 1314. These types of data may include information about the patient's peptides, HLAs and other biological or health information about the specific patient.

In certain embodiments, the second data may be determined by analyzing information related to HLA typing and associated peptides. Methods and techniques that can be utilized to determine the HLA type and the associated peptides and the subsequent data analysis include but are not limited to the procedures described in Example 8 in this disclosure. For example, the HLA typing may be based on either a buccal swab DNA test or blood analysis and wherein the information related to peptides may be based on analysis of tissue-specific and disease-related biological fluid. In another example, analyzing associated peptides may include stripping peptides from HLA complexes and determining peptide sequences. Removing the peptides that are bound to the patient's HLAs may be accomplished via several different ways, including protein chemistry techniques such as altering the pH value of the biological fluid in order to disrupt the interactions between the peptides and the HLAs, denaturation of the peptides using agents such as DMSO. In some embodiments, when the specific patient has MS, analyzing data related to associated peptides may include analyzing cerebrospinal fluid peptide data. When a patient has a T-cell associated immunological disease such as MS, systems and methods provided herein may predictively adjust treatment regimens for removing T-cells. In the case of MS, the adjustment may relate to peptides derived from myelin or a non-myelin CNS protein including an aquaporin channel. Myelin may include a mixture of proteins rather than a single protein and may include proteins such as myelin oligodendrocyte glycoprotein (MOG), myelin basic protein (MBP), myelin proteolipid protein (PLP), opalin protein, oligodendrocyte-specific protein (OSP), myelin-associated glycoprotein (MAG), or a combination thereof. Non-limiting examples of myelin peptides include the exemplary peptides described previously.

Following biosynthesis, proteins often undergo post-translational modification. Likewise, peptides that are bound to HLAs in HLA-peptide complexes may be derived from proteins that may have undergone post-translational modifications such as phosphorylation and glycosylation, or may contain one or more mutations (e.g., amino acid substitutions, deletions, insertions), or may be truncated. Accordingly, disclosed embodiments of the present disclosure include embodiments of a system where the first set of peptides and the second set peptides may be variations of a same peptide. "Variations of a same peptide" may include copies of a same peptide that may have undergone modifications and mutations as described above. Alternatively, the first set of peptides and the second set of peptides may be different from each other. In addition to removal of the patient's second subpopulation of the disease-related T-cells that are inactive against second set of peptides, disclosed embodiments may further include removal of the patient's first subpopulation of the disease-related T-cells that are active against the first set of peptides. The present disclosure is not limited by the manner in which the first and second subpopulation of the disease-related T-cells are removed. For example, the remedial action may be taken to remove the first subpopulation of disease-related T-cells and the second subpopulations of disease-related T-cells simultaneously. Alternatively, the remedial action may be taken to remove the first subpopulation of the disease-related T-cells and the second subpopulation of the disease-related T-cells sequentially, for example, the second subpopulation of the disease-related T-cells followed by the first subpopulation of the disease-related T-cells, or vice versa.

Disclosed embodiments may involve determining using the first set of data that the second set of peptides in the specific patient corresponds to the later progression of the disease. For example, data derived from one or more patients reflected in the first set of data might indicate a likelihood that a disease will progress in a manner such that other peptides (a second set) not currently triggering a disease in the particular patient may do so in the future. In the simplest way, this may be determined by locating a single patient exhibiting a progression phenomenon. For more reliable prediction, it may be beneficial to determine that a group of individuals whose information is reflected in the first data, exhibited the progression.

In alternative embodiments, additional information may be used to assist in determining that the second set of peptides in the specific patient correspond to a later progression of a disease. Although not required, the additional information may include data on other factors that correlate to disease progression. For example, the first set of data may include a host of information about a population and about biological and health information related to individuals in the population. A machine learning algorithm run on the first data might identify relationships between one or more pieces of biological or health information and a particular disease progression. In this way, through artificial intelligence, accuracy of prediction may be enhanced.

Machine learning algorithms or models may be trained using training examples. Some non-limiting examples of such machine learning algorithms may include classification algorithms, data regressions algorithms, segmentation algorithms, support vector machines, random forests, nearest neighbors algorithms, deep learning algorithms, artificial neural network algorithms, convolutional neural network algorithms, recursive neural network algorithms, linear machine learning models, non-linear machine learning models, ensemble algorithms, and so forth. For example, a trained machine learning algorithm may comprise an inference model, such as a predictive model, a classification model, a regression model, a clustering model, a segmentation model, an artificial neural network (such as a deep neural network, a convolutional neural network, a recursive neural network, etc.), a random forest, a support vector machine, and so forth. In some examples, the training examples may include example inputs together with the desired outputs corresponding to the example inputs. Further, in some examples, training machine learning algorithms using the training examples may generate a trained machine learning algorithm, and the trained machine learning algorithm may be used to estimate outputs for inputs not included in the training examples. In some examples, engineers, scientists, processes and machines that train machine learning algorithms may further use validation examples and/or test examples. For example, validation examples and/or test examples may include example inputs together with the desired outputs corresponding to the example inputs, a trained machine learning algorithm and/or an intermediately trained machine learning algorithm may be used to estimate outputs for the example inputs of the validation examples and/or test examples, the estimated outputs may be compared to the corresponding desired outputs, and the trained machine learning algorithm and/or the intermediately trained machine learning algorithm may be evaluated based on a result of the comparison. In some examples, a machine learning algorithm may have parameters and hyper parameters, where the hyper parameters are set manually by a person or automatically by an process external to the machine learning algorithm (such as a hyper parameter search algorithm), and the parameters of the machine learning algorithm are set by the machine learning algorithm according to the training examples. In some implementations, the hyper-parameters are set according to the training examples and the validation examples, and the parameters are set according to the training examples and the selected hyper-parameters.

In some embodiments, trained machine learning algorithms (also referred to as trained machine learning models) may be used to analyze inputs and generate outputs. In some examples, a trained machine learning algorithm may be used as an inference model that when provided with an input generates an inferred output. For example, a trained machine learning algorithm may include a classification algorithm, the input may include a sample, and the inferred output may include a classification of the sample (such as an inferred label, an inferred tag, and so forth). In another example, a trained machine learning algorithm may include a regression model, the input may include a sample, and the inferred output may include an inferred value for the sample. In yet another example, a trained machine learning algorithm may include a clustering model, the input may include a sample, and the inferred output may include an assignment of the sample to at least one cluster. In an additional example, a trained machine learning algorithm may include a classification algorithm, the input may include an image, and the inferred output may include a classification of an item depicted in the image. In some examples, the trained machine learning algorithm may include one or more formulas and/or one or more functions and/or one or more rules and/or one or more procedures, the input may be used as input to the formulas and/or functions and/or rules and/or procedures, and the inferred output may be based on the outputs of the formulas and/or functions and/or rules and/or procedures (for example, selecting one of the outputs of the formulas and/or functions and/or rules and/or procedures, using a statistical measure of the outputs of the formulas and/or functions and/or rules and/or procedures, and so forth).

In some embodiments, artificial neural networks may be configured to analyze inputs and generate corresponding outputs. Some non-limiting examples of such artificial neural networks may include shallow artificial neural networks, deep artificial neural networks, feedback artificial neural networks, feed forward artificial neural networks, autoencoder artificial neural networks, probabilistic artificial neural networks, time delay artificial neural networks, convolutional artificial neural networks, recurrent artificial neural networks, long short term memory artificial neural networks, and so forth. In some examples, an artificial neural network may be configured manually. For example, a structure of the artificial neural network may be selected manually, a type of an artificial neuron of the artificial neural network may be selected manually, a parameter of the artificial neural network (such as a parameter of an artificial neuron of the artificial neural network) may be selected manually, and so forth. In some examples, an artificial neural network may be configured using a machine learning algorithm. For example, a user may select hyper-parameters for the an artificial neural network and/or the machine learning algorithm, and the machine learning algorithm may use the hyper-parameters and training examples to determine the parameters of the artificial neural network, for example using back propagation, using gradient descent, using stochastic gradient descent, using mini-batch gradient descent, and so forth. In some examples, an artificial neural network may be created from two or more other artificial neural networks by combining the two or more other artificial neural networks into a single artificial neural network. In a broadest sense, determining using the first data that the second set of peptides in the specific patient corresponds to the later progression of the disease does not require machine learning or artificial intelligence.

As implemented by way of example, determining using the first data that the second set of peptides in the specific patient corresponds to the later progression of the disease may occur at block 1416 in FIG. 14. This function may be achieved using, by way of example only, processor 1314 in FIG. 13. In that situation, the first set of data may be located on server 1316, and processor 1314 may retrieve relevant data and arrive at the determination. Alternatively, processor 1314 might be used to send information about the specific patient via network 1318 to server 1316, or to one or more processors, not shown, associated with server 1316. In this way, the determination may occur at a location remote from the processor 1314, and the determination, which may include additional related information, may be returned to processor 1314.

Regardless of where the processor making the determination is located, it may be configured to confirm that the second set of peptides, which does not yet activate the disease-related T-cells are predicted to do so later, are indeed associated with a later stage of the disease. This determination may be done, for example, by comparing the peptides that do not yet activate the disease-related T-cells with the known biomarkers of the more advanced stages of the disease. For instance, multiple sclerosis can be divided into 3 main patterns as described herein.

In some embodiments, determining that the second set of peptides corresponds to the later progression of the disease may include comparing disease-related parameters including years from onset, EDSS and treatment; HLA typing analysis; and analysis of peptides presented by corresponding HLA proteins. These disease related parameters may be factors that aid in predicting disease progression, particularly when such factors correlate to disease pattern. The correlations may be identified with machine learning, as described earlier.

Once it is confirmed that the peptides that do not yet activate the disease-related T-cells in the one or more patients, measures may be undertaken to prevent further progression of the disease in the specific patient. In a system embodiment, this may occur with the aid of at least one processor. For example, at least one processor may be configured to take remedial action to remove the second subpopulation of the disease-related T-cells from the patient before the second set of peptides activates the second subpopulation of the disease-related T-cells. Taking "remedial action" may include developing a preventive strategy. For example, a biological filter in accordance with the present disclosure may be used as a prevention therapy to enable removal of the pathogenic T-cells from the circulation of a patient, even before these cells are activated towards specific targets in the body. In this instance, taking remedial action may involve determining characteristics of such a filter for a particular patient. Additionally or alternatively, taking remedial action may include one or more of outputting such characteristic information to a display, transmitting over a network such characteristic information to a medical professional or organization, transmitting the characteristic information to a filter manufacturer to enable filter construction for the specific patient, or outputting the characteristic information to memory associated with a machine or system that constructs biological filters.

By way of example, remedial action is depicted in block 1418 of FIG. 14, and may be implemented by way of example, by processor 1314 (or another processor accessed via a network such as the Internet). In one sense, the remedial action might include displaying information about the disease progression on a display, such as display 1320.

The remedial action may include adjusting treatment of the patient based on the identified second set of peptides. In one embodiment, adjusting may involve notifying a healthcare entity of a need for a treatment protocol change so that the healthcare entity may then take the appropriate action. In another embodiment adjusting may involve developing instructions that enable a machine to manufacture a biological filter reflecting a change in patient treatment from a filter previously used with the patient.

Thus, in one sense, a remedial action may simply include outputting an instruction to remove the second subpopulation of the disease-related T-cells. Such instruction may be generated using a computer program that is readable by a computer for executing commands. The instructions may be provided in a form that requires further translation, or they may include output the data for use in building a filter that includes second set of peptides.

Consistent with some disclosed embodiments, at least one processor may be further configured to identify additional sets of common peptides that do not activate the disease-related T-cells; determine that the additional sets of peptides correspond to the later progression of the disease; and take remedial action to remove the additional subpopulations of the disease-related from the patient before the additional sets of peptides activate the additional subpopulations of the disease-related T-cells. For example, the progression of a disease may change more than once over time. That is, as a disease progresses, an additional set of peptides, other than the first and second set, may trigger, or may be expected to trigger T-cell activation. In such instances, embodiments of the invention may identify these additional sets of peptides and initiate remedial action to remove them before they have opportunity to activate T-cells. The remedial action taken with the additional peptides may be similar to those taken with the second set of peptides. Thus, in some embodiments, treatment may be adjusted based on the identified additional sets of peptides. This may occur, as described earlier by outputting an instruction to remove the additional subpopulations of the disease-related T-cells. Such instruction may be generated using a computer program that is readable by a computer for executing commands, to one or more output devices or systems as described above. In a further example, the at least one processor may be further configured to take remedial action, where the remedial action includes outputting data for use in building a filter that includes the additional sets of peptides. The additional sets of common peptides that do not activate the disease-related T-cells but will potentially become active as the disease progresses may be removed together with first and/or second sets of peptides, or after. In one embodiment, the remedial action is taken to remove the first, the second and the additional subpopulations of disease-related T-cells simultaneously.

While the foregoing embodiments are discussed in connection with a system for predictively adjusting treatment, it is to be understood that the reference to a system is for illustrative purposes only. The same principles may be implemented in a method or in computer readable media, both of which are within the scope of this disclosure. For example, the process illustrated in FIG. 14 may occur without the use of a processor or a system, or with a different system. Similarly, the process illustrated in FIG. 14 and the associated description herein may be implemented in computer readable media that contain instructions for causing at least one processor to perform such a method.

Method of Removing T-Cells from a Patient

Disclosed embodiments may involve a method of removing cells from a patient or more generally for removing cells from biological fluid. The fluid can be any of the approximately 40+biological fluids. As used herein, the term "biological fluid" refers to a bodily fluid or fluid that is derived from the body of a mammal, such as human. Non-limiting examples of biological fluids include whole blood, serum, plasma, cerebrospinal fluid, synovial fluid, alveolar lavage fluid, pancreatic juice, gastrointestinal lavage fluid, peritoneal lavage, lymph, bone marrow, amniotic fluid, semen, pleural fluid, breast milk, pericardial fluid, saliva, feces, bile, and urine.

The removed cells may be T-cells, non-T-cells, pathogenic cells, or non-pathogenic cells, depending on the intended purpose of the removal. One non-limiting example of a purpose for cell removal may include removing particular cells that are known or suspected to trigger a disease. By removing the triggering cells, the disease might be mitigated.

Such a method may involve drawing biological fluid containing the target cells from the patient. The biological fluid containing the specific cells can then be extracorporeally flowed through a medium hosting material that selectively binds to only the specific cells. In this way, the specific cells can be trapped by the medium, and the rest of the biological fluid that is not trapped can be returned to the patient. In this way, target cells in a patient's blood or other biological fluid can be removed.

For illustrative purposes, reagents and instruments are described below in connection with a few examples. It is to be understood that the examples, reagents and instruments are exemplary only.

Disclosed methods may be used on a patient. The term "patient" may include a human or other mammal. In some embodiments, a method of removing specific T-cells is contemplated. The term "specific T-cells" has also been described previously.

In some embodiments, T-cells which do not express the particular T-cell antigen receptor or receptors being targeted may not be removed. The term "T-cell" as described above may include any type of lymphocyte which develops in the thymus gland and which plays a central role in the immune response. In some embodiments, the specific T-cells may include one or more of helper CD4+ T-cells, cytotoxic CD8+ T-cells, memory T-cells, regulatory CD4+ T-cells, natural killer T-cells, mucosal associated invariant T-cells and/or gamma delta T-cells. Alternatively or additionally, the specific T-cells may include at least one of CD4+ cells or CD8+ cells.

Targeted T-cells may be either pathogenic or non-pathogenic. Pathogenic T-cells may play a similar role as non-pathogenic T-cells except that pathogenic T-cells may recognize self-structures and materials and attack them. As used herein, the term "pathogenic cells" may refer to any cell, either endogenous or foreign, which may be associated with a disease or other affliction. By targeting and removing pathogenic cells, the disease in the patient may be mitigated. Non-pathogenic T-cells may be targeted for removal, for example, if it is anticipated that a particular affiliation will evolve to a point where non-pathogenic T-cells in the present may become pathogenic in the future. Thus, proactive removal of non-pathogenic cells may prevent later manifestations of disease.

The pathogenic cells may be associated with any one of the autoimmune diseases described herein. In certain embodiments, the pathogenic cells may be associated with autoimmune diseases including but not limited to multiple sclerosis, lupus, celiac, Sjögren's syndrome, polymyalgia rheumatica, Akylosing spondylitis, type 1 diabetes, alopecia areata, vasculitis, autoimmune hepatitis, autoimmune lymphoproliferative syndrome (ALPS), autoinflammatory diseases, Goodpasture syndrome, Lambert-Eaton syndrome, antiphospholipid syndrome (APS), neuromyelitis optica (NMO), paraneoplastic syndromes, primary biliary cholangitis, Stiff-person syndrome (SPS), antiphospholipid antibody syndrome (APS), or temporal arteritis.

In other embodiments, the pathogenic cells may be associated with a cancerous disease, such as a hematological cancer. Hematological cancers may include leukemia, Non-Hodgkin lymphoma, Hodgkin lymphoma, multiple myeloma, or any other cancer of blood cells. In other embodiments, the cancerous disease may be solid. Solid cancers may include lung, breast, colorectal, pancreatic, liver, prostate, or any other solid tumor forming in a tissue.

A method of removing specific T-cells, pathogenic cells, or non-pathogenic cells may include drawing biological fluid from the patient. When the biological fluid includes blood, references to blood herein may include either whole blood or a blood fraction. As used herein, the term "blood" may refer to a body fluid present in humans and other organisms that transports substances including nutrients and oxygen to cells and transports metabolic waste products away from cells. The term "blood fraction" as used herein may refer to subcomponents of whole blood. Blood fractions may include one or more of plasma, white blood cells, red blood cells, and platelets. The biological fluid may also include cerebrospinal fluid (CSF). As used herein, "CSF" may refer to the clear, colorless fluid found in the brain and spinal cord. In some embodiments, the biological fluid may include bone marrow. As used herein, the term "bone marrow" may refer to the semi-solid tissue found in the spongy or cancellous portion of bones, and which may produce white blood cells, red blood cells and platelets. In other embodiments, the biological fluid may include synovial fluid. As used herein, the term "synovial fluid" may refer to the non-Newtonian fluid found in the cavity of synovial joints, and which may provide lubrication for joint surfaces. In other embodiments, the biological fluid may include fluid obtained from an alveolar lavage. As used herein, "alveolar lavage fluid" may refer to fluid which is introduced to the lungs and subsequently collected. In some embodiments, the biological fluid may include peritoneal fluid. As used herein, the term "peritoneal fluid" may refer to liquid in the abdominal cavity and which may lubricate the tissues that line the abdominal wall and pelvic cavity. Thus, as used herein, the term "drawing" as it related to biological fluid refers to any mechanism for removing the biological fluid from the patient.

Figure 15:
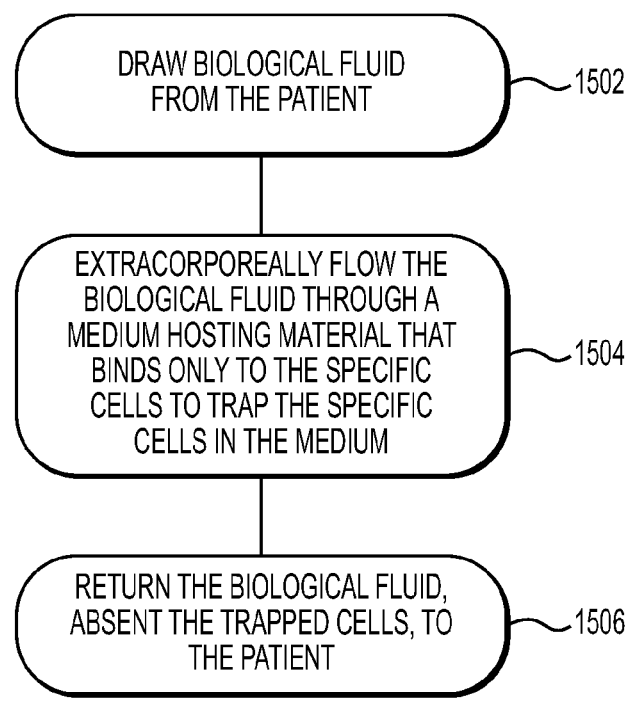
FIG. 15 illustrates an exemplary method for removing specific cells from biological fluid consistent with embodiments of this disclosure.

This concept is conveyed by way of example at block 1502 in FIG. 15, where biological fluid is generally indicated as being drawn from a patient. Such a process of drawing biological fluid from a patient may include, for example, aspiration and/or drainage. Aspiration may include removal by suction of fluid from an organism and may be performed, for example via a needle or catheter. If the biological fluid is blood, the blood may be removed by inserting a needle into a vein, the needle being connected to a collection container or a tubing set.

Disclosed embodiments may further include extracorporeally flowing the biological fluid through a medium hosting material that selectively binds to only the specific cells, to thereby trap the specific cells with the medium. The terms "medium" and "selective binding" were described previously. In block 1504 of FIG. 15, when biological fluid is extracorporeally flowed through a host medium, the specific cells (or in other embodiments other target materials) may preferentially attach in any way in order to trap the target material (e.g., specific cells). In a broad sense, binding encompasses any process of combination, adherence, coupling, or reaction that causes the target cells to be removed.

Many types of surface media may be used, including solids, semi-solids or fluids. If solid or semi-solid, the medium can have any form. Examples provided earlier in FIGS. 2A-2D include sheet material, fibers, beads, and sponge-like material. Other examples include mesh structures, liquids and gels. However, these are only examples. The method may be practiced without regard to a specific host material.

Similarly, the make-up of the medium can vary depending on intended use. By way of example only, the medium may be characterized in one or more of the following ways: inert, non-synthetic; synthetic; a polymer; a high performance thermoplastic; polysulfone; a polysulfone derivative; a glass matrix; a silicon matrix; polydimethylsiloxane (PDMS); polycarbonate; polyetherimide (Ultem); Tritan; a polyelectrolyte; polyacrylic acid; or poly(2-aminoethyl)acrylamide. Alternatively or additionally, the medium may include polyacrylic acid present at about 5% to about 40% mass percentage; polysulfone present at about 60% to about 95% mass percentage; polystyrene; polyethylene glycol (PEG) or a PEG derivative; PEG density maximized by generating six-arm star shaped molecules of PEG that can be intermolecularly crosslinked; and/or avidin, streptavidin or any variation thereof. Again, these are only examples and are not to be considered limiting of this disclosure in its broadest sense.

Figure 16:
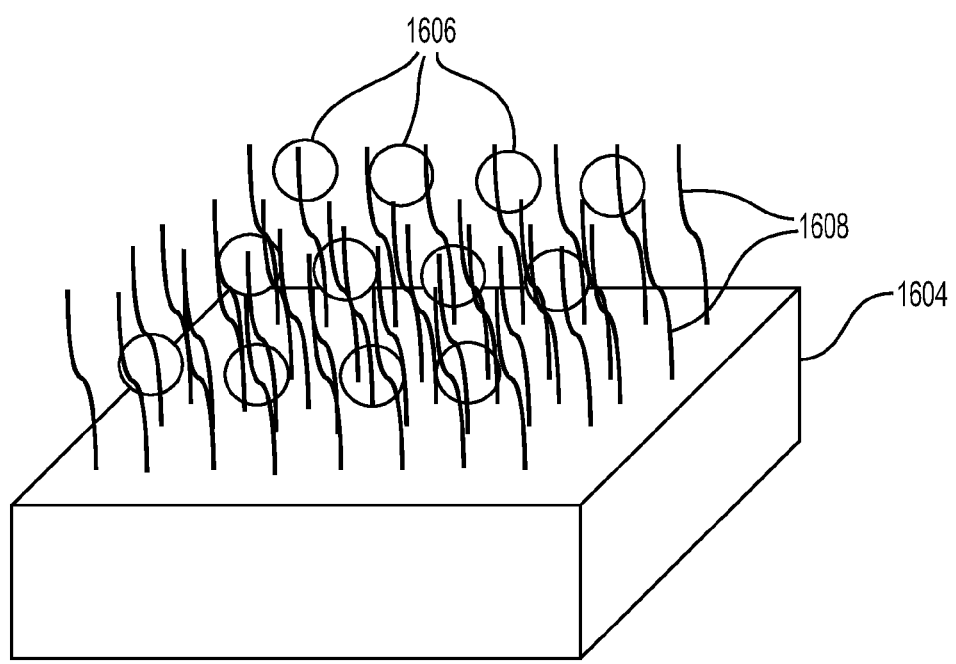
FIG. 16 schematically illustrates a medium hosting material that captures specific cells consistent with embodiments of this disclosure.

By way of schematic representation, FIG. 16 shows an exemplary embodiment of a medium having an inert surface 1604. By way of one example, the inert surface may include streptavidin. The medium 1604, while illustrated as a sheet, can be in any form including but not limited to the forms illustrated in FIGS. 2A-2D.

As illustrated in FIG. 16, the medium 1604 may host a binding material 1608 that selectively binds to and captures, biological material, such as cells 1606. For example, the cells 1606 may be pathogenic T-cells, and may be attached to the medium in any way, including through covalent bonding, non-covalent interactions or adsorption. Non-covalent interactions may include hydrogen bonding, ionic interactions, hydrophobic interactions, or pie stacking. In certain embodiments, the binding material 1608 may include a protein, and in this instance, reference numeral 1608 may depict a protein. In some embodiments, the binding material 1608 includes an antibody, and in this instance, reference numeral 1608 may depict an antibody. For example, the antibody may recognize a specific epitope on the biological material (e.g., cells 1606), thereby capturing the biological material and immobilizing it on the medium. The term "antibody" as used herein may include Fab, Fab', F(ab')2, Fabc, Fv fragment, or any other antigen-binding fragment; or antigen-binding antibody portion thereof. In certain embodiments, the antibody may include a monoclonal antibody, a polyclonal antibody, a recombinant antibody, a chimeric antibody, a humanized antibody, a human antibody, or an antigen-binding fragment or antigen-binding portion thereof. The medium may include a plurality of different antibodies that recognize a plurality of different antigens on a plurality of different biological materials.

While binding material 1608 may selectively bind to only specific cells, the binding material 1608 may be initially bound to host medium 1604. Therefore, use of the phrase "selectively binds to only the specific cells" refers to the selective binding of the cell (or other biological material) capture process and not to the mechanism connecting the host medium 1604 to the binding material 1608, which connection may occur through binding.

In some embodiments, the selectively binding host material includes a human leukocyte antigen (HLA). The HLA may be bound to a peptide to form an HLA-peptide complex. In one example, the HLA-peptide complex may recognize a specific epitope on the biological material (e.g., T-cells.). If by way of example, the medium may include avidin, streptavidin or any variation thereof, the capture material may be linked to a biotin, which may interact with the avidin, streptavidin, or variation thereof on the surface of the medium, thereby anchoring the capture material to the medium. By way of another example, the medium may include a free carbonyl group, amine group, maleimide group, or any other functional group, which may interact with a functional group on the capture material, thereby anchoring the capture material to the medium. In yet another example, the medium includes a blend of polysulfone and polyacrylic acid and the capture material may be a protein, which may be bound to the medium via the carboxyl group of the polyacrylic acid. Further, the blend of polysulfone and polyacrylic acid may be modified to include an amine group and the protein may be bound to the medium via reaction with the amine group. In a further example, the blend of polysulfone and polyacrylic acid may be modified to include a maleic acid, a maleimide group or an analog thereof. The maleic acid, a maleimide group or analog thereof may be elongated with a carbohydrate linker. The capture material may be bound to the medium via reaction with the maleic acid, a maleimide group or analog thereof.

Figure 17A:
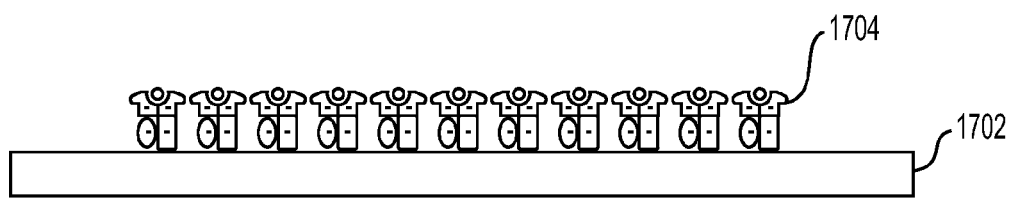
FIG. 17A schematically illustrates a medium hosting HLA-peptide complexes consistent with embodiments of this disclosure.
Figure 17B:
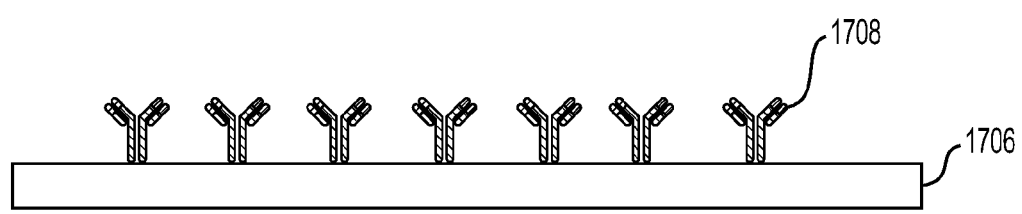
FIG. 17B schematically illustrates a medium hosting antibodies consistent with embodiments of this disclosure.

By way of schematic representation, a medium 1702 including HLA-peptide complexes 1704 and a medium 1706 including antibodies 1708 are shown in FIGS. 17A-17B. The media 1702 and 1706, while illustrated in sheet form, can be in any form including but not limited to the forms illustrated in FIGS. 2A-2D.

In some embodiments, the capture material may include an HLA protein, and may further include a peptide to form an HLA-peptide complex. The HLA-peptide complex may be disposed on the medium, for example, through maleic acid, maleimide or an analog thereof.

In some embodiments, HLA-peptide complexes may be recombinantly designed and expressed. For example, the HLA protein may be designed to include a fusion protein or a tag. In another example, the HLA protein may be designed to include a cysteine residue at the C-terminus. In some embodiments, the HLA protein may be linked to a C-terminal cysteine via a peptide linker. Alternatively, HLA-peptide complexes may be obtained endogenously from an individual, such as a patient. In some embodiments, the HLA proteins include HLA I and/or HLA II. In some embodiments, the HLA proteins of the HLA-peptide complexes may be truncated. In certain embodiments, the truncation results in a C-terminal cysteine. The HLA-peptide complex may react with maleimide or an analog thereof on the medium, thereby anchoring the HLA-peptide complex to the medium. In certain embodiments, recombinantly designed and expressed HLA complexes may comprise recombinant proteins similar to proteins of an individual. In preferred embodiments, the recombinantly designed and expressed or endogenous HLA complexes may comprise type I or II HLA proteins. In some embodiments, recombinantly designed HLA proteins may include a peptide-binding cleft or groove for loading and binding to endogenous or synthesized peptides that may be subsequently presented. In certain embodiments, the endogenous or synthesized peptides to be loaded may be disease-associated immunogenic peptides. In some embodiments, the specific T-cells include T-cell receptors that are specific for antigen peptides derived from a protein associated with an autoimmune disease including any one of the exemplary autoimmune diseases described herein. In certain embodiments, the autoimmune disease may include multiple sclerosis, type 1 diabetes, myasthenia gravis, or Crohn's disease. In some embodiments, HLA-peptide complex may recognize a specific T-cell receptor on a group of T-cells, thereby capturing the T-cells. In some embodiments, the T-cells may include CD4+ and/or CD8+ T-cells. In some embodiments, the HLA-peptide complex may include a plurality of different HLA-peptide complexes, each recognizing a different T-cell receptor on a plurality of groups of T-cells.

Extracorporeally flowing the biological fluid through a medium may include flowing the biological fluid through the medium once or recirculating the biological fluid a plurality of times or continuously for a time period. Multiple passes may be necessary because in any one pass, the full volume of biological fluid may not contact a filter surface sufficiently to bind a sufficient percentage of the cells to be removed. Of course, the amount of recirculation, if any, is a function of the specific filter design and the particular use case.

Disclosed embodiments may also include returning the biological fluid, absent the trapped cells, to the patient. The return of cells may occur after a sufficient period of time has passes to ensure that a desired volume of targeted cells is removed by the filter. In block 1506 of FIG. 15, the cells may be returned in any manner. For example, they may be returned via a tubing set extending from an outlet of the filter to the patient, or, for example, the cells may be collected and returned at a later time. To facilitate efficiency of the filter, in the case of blood for example, the blood may first go through an initial separation to segregate portions of the blood containing T-cells from those portions that do not. Then, the T-cell portion can be circulated through the biological filter while the remaining portions might be immediately returned to the patient or held for later return.

These processes may be facilitated through the use of one or more peristaltic pumps, and one or more reservoirs. In certain embodiments, the biological fluid may be enriched before returning to the patient. By way of example, nutrients or a pharmaceutical composition may be added prior to return.

Method for Producing a Personalized Biological Filter for Selective Removal of Pathogenic Cells from a Patient Some disclosed embodiments relate to methods of producing a personalized biological filter for removal of pathogenic cells from a patient. Such biological filters, in accordance with the embodiments disclosed herein, may be useful for treating a disease of a patient caused by pathogenic cells, such as T-cells. Pathogenic cells that would otherwise attack self-proteins in the body causing activation of those cells and destruction of self-proteins and cells, may be removed using a biological filter containing HLA-peptide complexes, including the specific immunogenic peptides. Since disease triggering HLA-peptide complexes may vary from patient to patient, a filter may be personalized to the biology of a particular patient. For example, analyses may be performed on the patient to determine one or more HLA types of the patient and to determine identities of one or more pathogenic peptides. Then, a filter may be constructed with the HLA-peptide complex(es) unique to the patient's disease, thereby rendering the filter personalized to the patient. Alternatively, varying filters may be maintained in stock with common combinations HLA-peptide complexes, and the appropriate filter may be selected after analysis of the patient is performed. Such a filter specifically selected and attached together from stock to match a unique HLA-peptide complex combination of a patient is considered a personalized filter within the meaning of this disclosure. As discussed below, a biological filter consistent with this disclosure may include HLA-peptide complexes bound to an inert filter surface medium. This example and others are discussed below in greater detail.

The filter may have any suitable form capable of a removal function. For example, it may be configured in the form of or to include one or more sheets of material to which biological fluid components bind, bond, or otherwise react; or other structures that result in a similar effect. Such structures may include, for example, mesh, fibers, gel, beads, scaffold, or any other material with surface area configured for biological filtering.

Biological filters consistent with embodiments of this disclosure may be configured to capture cells, proteins, nucleic acids, lipids, polysaccharides, or any other biological materials. For example, the filter might include proteins or may be anchored with proteins that recognize and capture pathogenic cells or non-pathogenic cells, depending on the function that the filter is designed to accomplish. In some embodiments, pathogenic cells may have the same role as non-pathogenic cells except that they recognize self-structures and materials and attack them. By way of example, a filter may be designed to remove one or more of a host of pathogenic cells associated with a host of diseases. For example, the filter may be designed to remove pathogenic lymphocytes.

Figure 18:
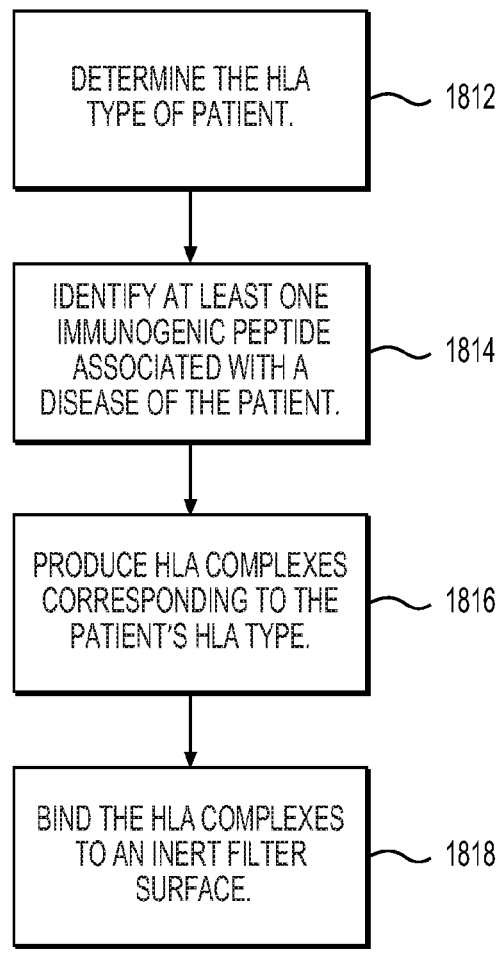
FIG. 18 illustrates in block form various steps of an exemplary method of producing a personalized biological filter for selective removal of pathogenic cells consistent with embodiments of this disclosure.

Consistent with some disclosed embodiments, a method of producing a personalized biological filter may include determining an HLA-type of the patient. HLA typing for a particular patient may be performed using any procedure that identifies one or more HLA types of the patient as described previously. Thus, identification of the HLA type of a patient is generally reflected, by way of example, in block 1812 of FIG. 18, without limitation as to the manner in which the HLA type is obtained, or the biological fluid from which it is obtained. Examples of such fluids include, without limitation, blood, cerebrospinal fluid, or any other suitable body fluid from which HLA typing may be determined, including all examples of biological fluids previously described herein.

In some embodiments, the method of producing a personalized biological filter may include identifying at least one immunogenic peptide associated with a disease of the patient or identifying at least one clone of cells that is recognized and activated by immunogenic peptides associated with a disease of the patient. The term peptide generally refers to a short chain of amino acids bound together by a peptide bond. A peptide's immunogenicity may be determined by standard means. In one exemplary process for identifying at least one immunogenic peptide, a collected fluid sample from a patient may be processed to separate cells from fluid. The cells may then be lysed to a collect a protein fraction. This may result in a mixture of all the proteins expressed by the cells, resulting in a collection of many HLA-peptide complexes. Immunoprecipitation may then be performed on the protein fraction by introducing antibodies into the protein mixture that are known to bind to HLA complexes. In this way, the HLA complexes may be separated from the rest of the proteins. Next, peptide stripping may be performed on the HLA-peptide complexes to dissociate the proteins from the HLAs. Mass spectrometry may then be performed on each stripped peptide to identify the peptides associated with a specific disease. More particularly, mass spectroscopy reveals an identifying sequence for each peptide. Those sequences may then be compared with sequences already known to be associated with a protein linked to a disease. For example, the sequences may be fed into a search engine that looks up the sequence to determine if the related peptide is associated with a disease. In the case of multiple sclerosis, for example, myelin related proteins would be identified. In a broadest sense, embodiments of this disclosure are not limited to a particular mechanism for identifying specific disease-related peptides. Thus, block 1814 of FIG. 18 generally refers to identifying at least one immunogenic peptide associated with a disease, without specifying a particular method of doing so.

An even more specific group of HLA-peptide complexes may be identified by using a bioinformatics database to identify the peptides with the strongest bonding affinity to the patient's HLAs. Once these top candidates are identified, a test surface or group of test surfaces may be constructed and anchored with separate areas on which synthesized HLA-peptide complexes may be bound. The patient's blood fraction called PBMC's (Peripheral Blood Mono Nuclear Cells) may then be stained on the test surface areas. This process may then reveal which HLA-peptide complexes bind to the T-cells and determines the amount of T-cells from a certain clone are in the blood. For example, by marking the PBMC's and using a process such as fluoroscopy, it may be possible to gauge the volume of T-cells that bind to each test area. The HLA-peptide complexes associated with the areas of highest bonding signaling may reflect an amount of peripheral T-cells to be removed. Significant bonding indicates the HLA-peptide complexes that should be included in a personalized treatment filter for the patient.

In certain embodiments, a plurality of disease-associated immunogenic peptides may be identified or analyzed. For example, a series of HLA-peptide complexes may be identified as triggering a disease. If so, many such complexes may be tested to determine the extent to which they trigger disease. In some embodiments, the identified peptides may be quantified. If so, those that pass a threshold (e.g., volume that bind to T-cells in a test) may be selected for use in a filter. Identification of the peptides may be achieved through amino acid sequencing. Additionally, such peptides may be compared to a database of disease-related immunogenic peptides to derive relevant information about the peptides. For example, as discussed in more detail herein, a peptide's binding affinity to a particular HLA expressed in a patient may be determined though the use of commercially or publicly available databases. In some embodiments, a peptide's binding affinity for a particular HLA may be quantified. By quantifying the binding affinity, it may be possible to select the peptide-HLA combinations with the highest binding affinity, thereby guiding the design of a biological filter.

Thus, in some embodiments, identifying or analyzing an immunogenic peptide may include comparing the peptide with a database of disease-related immunogenic peptides that includes peptide binding affinities for HLA complexes. When the HLA types of the patient are included in the analysis, such comparisons may help narrow the pool of HLA-peptide complexes that trigger disease in that patient.

In certain embodiments, identification or analysis of peptides may be determined through cerebrospinal fluid analysis or tissue-specific disease related analysis. By way of example, tissue from a diseased individual may be collected. A population of HLA complexes with connected or loaded peptides may be isolated from cells of the diseased individual. The peptides may then be separated from the HLA complexes by, for example, chemical means. The separated peptides may then be sequenced and analyzed for frequency in order to be linked to the particular disease of the individual. Such identification of at least one immunogenic peptide associated with a disease of the patient is generally reflected, among other identification methods, in block 1814 in FIG. 18.

A method of producing a personalized biological filter may include recombinantly or endogenously producing HLA complexes corresponding to the determined HLA type of the patient and the at least one immunogenic peptide. The HLA type may include HLA I or HLA II or both. The particular complexes to be produced may be based on analyses of the binding affinity between HLAs expressed by the patient and the at least one identified immunogenic peptide. One or more combinations of HLAs and immunogenic peptides may be selected for production. Endogenous production of HLA complexes may involve obtaining endogenous HLA complexes from the patient. Recombinant production of HLA complexes may involve incorporating recombinant DNA of interest into a system capable of transcribing the DNA into mRNA and translating the mRNA into an amino acid sequence corresponding to the recombinant HLA complex. An example of a DNA plasmid is pET-21d (+) or any other available expression vector, that can be transfected into bacteria expression systems such as *E. coli* (e.g. BL21 or B834 strains) for protein production. Other expression systems can include but are not limited to insect cells, mammalian cells, cell free expression system or any other suitable system.] Recombinant HLA complexes may be altered from endogenous HLA complexes. Production of HLA complexes corresponding to the patient's HLA type is reflected, by way of example, in block 1816 in FIG. 18.

In some embodiments, the HLA complexes may include an HLA protein and an antigen peptide that is immunogenic. The immunogenic peptide, which may be identified as discussed herein, may be associated with a disease of the patient. The HLA complexes may be obtained endogenously from the patient. The HLA complexes may include recombinantly produced HLA proteins and immunogenic peptides according to the description above. The HLA complexes may include recombinantly produced HLA proteins and/or synthetically produced immunogenic peptides. An immunogenic peptide may be synthesized by standard procedures. In certain embodiments, the immunogenic peptide may be synthesized chemically either by manual or automatic procedures. In certain embodiments, the immunogenic peptide may be synthesized by fluorenylmethoxycarbonyl protecting group chemistry.

Aspects of this disclosure may further involve synthesizing at least one identified peptide associated with the disease of the patient. For example, when the disease is MS, such peptides may include those that form part of the myelin sheath that surrounds axons in the central nervous system of an individual. Alternatively, disease-associated peptides may include proteins common to most or all cell types. By way of example, such peptides may include cytoplasmic, cytoskeletal, nuclear, or membrane proteins.

A method of producing a personalized biological filter may include binding HLA complexes to an inert filter surface of the biological filter. Consistent with disclosed embodiments, a filter may include an inert material on which HLA complexes may be bound. The term "inert" is as described previously. In some embodiments, the filter may include at least one of polysulfone, a polysulfone derivative, glass matrices, silicon matrices, polydimethylsiloxane (PDMS), polycarbonate, polyetherimide (Ultem), Tritan, or a combination of the above or other substances. In other exemplary embodiments, the filter includes polysulfone. The filter may further include a polyelectrolyte or any polymeric additive either alone or in combination with another of the above-identified materials or other substances or materials. In other embodiments, the inert filter surface may include at least one of polyethylene glycol (PEG), a PEG derivative, polystyrene, avidin or streptavidin. Alternatively, the surface of the filter may be somewhat or highly absorbent or reactive with non-specific particles.

In certain embodiments, the filter may include a plurality of layers configured to permit fluid flow therebetween. Any layering structure, such as the structures described in FIG. 3, may be used so long as fluid may contact a sufficient portion of the filtering medium to achieve an intended filtering function.

The HLA complexes may be bound to the inert filter surface by any mechanism that permits the TCR of the target T-cell to bind to the HLA-peptide complex.

Binding may occur through bonding, anchoring, chemical reaction, or any other manner of attachment of the HLA complexes to the inert filter surface. For example, the inert filter surface may be chemically designed to enable specific molecular and chemical properties in order to react with the HLA complexes. The HLA complexes may be disposed on the inert filter surface, for example, through covalent bonding, non-covalent interactions, or adsorption. Examples of non-covalent interactions include but are not limited to electrostatic interactions, van der Waals forces, π-effects, and hydrophobic effects. In particular embodiments, the HLA complexes may bind to the inert filter surface via an analog. By way of example, the HLA complexes may be disposed on the inert surface through a maleimide analog. In other embodiments, the HLA complexes may covalently bind to the surface of the filter via a maleimide analog. In certain embodiments, the HLA complexes may be introduced to the surface of the filter in a solution in an excess amount in order to enable maximal saturation of the inert filter surface with the HLA complexes. In particular embodiments, the HLA complexes may bind to the inert filter surface via thiol binding, disulfide binding, amine binding, or binding of any other suitable functional group. Alternatively, the HLA complexes may bind covalently to the inert filter surface at, for example, a cysteine residue. Such binding of HLA complexes to an inert filter surface is reflected, by way of example, in block 1818 in FIG. 18.

In some aspects of the invention, the method of producing a personalized biological filter may further include loading an identified peptide onto the HLA complex bound to the insert filter surface. Peptides may be loaded onto HLA proteins to form HLA-peptide complexes as previously described herein.

The timing of loading an identified peptide onto the HLA complex and the binding of the HLA complex to the inert filter surface may be altered depending on the requirements of the particular implementation. In some embodiments, the loading and binding occur sequentially. That is, either the identified peptides are loaded onto the HLA complexes first before binding to the inert surface material, or the HLA complexes are bound to the inert surface material first, and the peptides are loaded thereafter. In other embodiments, the loading and binding occur substantially simultaneously.

A personalized biological filter may be used to selectively remove pathogenic cells from a patient. As mentioned earlier, removal of pathogenic cells from a patient may occur through any biological or chemical process. In some embodiments, this may involve flowing blood from the patient over the HLA complexes bound to the inert filter surface to thereby capture pathogenic cells. Pathogenic cells may be captured by the HLA complexes bound to the inert filter surface by any means, including binding, bonding, or reacting to the pathogenic cells. A personalized biological filter may be also be implemented as a stent coated with HLA protein complexes, inserted into blood vessel or in any place in the body. Periodically, the stent can be removed. A biological filter may be coated with streptavidin or any other chemical material and after injection of HLA proteins complexes conjugated with biotin, to the blood the patient is connected to an apheresis machine in order to remove the HLA complexes by specific binding of biotin streptavidin. By way of non-limiting example, the pathogenic cells may be associated with any one of the autoimmune diseases, cancers (solid tumor or hematological cancers) and post-transplantation complications disclosed herein. In one embodiment, the pathogenic cells may be associated with at least one of leukemia, acute leukemia, cancer, myasthenia gravis (MG), Lambert-Eaton syndrome, multiple sclerosis (MS), polycythemia vera (PCV), Thrombocytosis, Scleroderma, type 1 diabetes, psoriasis, Crohn's disease, or Multiple Sclerosis. In other aspects of the invention, the biological filter may be used to capture pathogenic cells associated with at least one of myeloproliferative diseases or viral, bacterial, fungi or parasitic infections.

Method of Treating a Disease in a Patient

Some disclosed embodiments relate to treatment of a patient and methods thereof. In some embodiments, patient treatment may refer to providing or offering personalized medicine to the patient. In some embodiments, a patient may be treated for disease. For example, the patient may be treated for various cancers, either hematological or solid tumors. Alternatively, in some embodiments, the patient may be treated for an autoimmune disease. In the context of autoimmune disease, treatment may entail down-regulation of a patient's immune system. Alternatively, treatment of autoimmune disease may include targeting one or more damage-causing agents and removing them from a patient's body. In some embodiments, the damage-causing agent may be pathogenic cells. While the present disclosure provides examples of specific diseases for treatment, it should be noted that aspects of the disclosure in their broadest sense are not limited to a particular disease. Rather, the foregoing principles may be applied to any disease suitable for treatment one or more of the varying mechanisms described herein.

Figure 19:
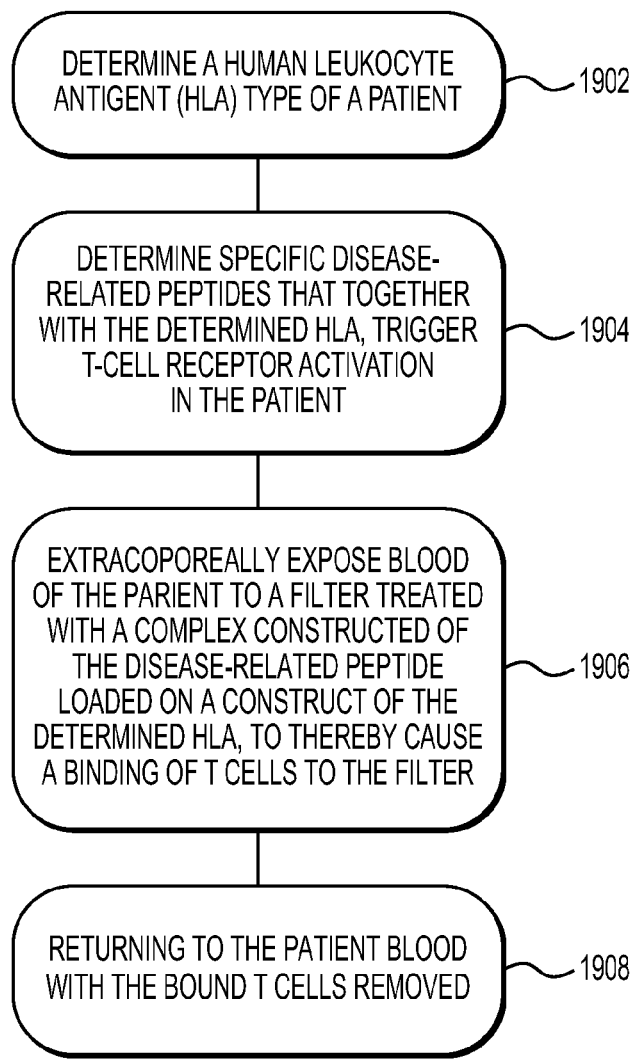
FIG. 19 illustrates in block form an exemplary method for using HLA-peptide complexes to extracorporeally remove T-cells from the blood of a patient, consistent with embodiments of this disclosure FIG. 20A schematically illustrates an HLA pentamer, consistent with embodiments of this disclosure.

Some embodiments of this disclosure may involve determining a human leukocyte antigen (HLA) type of the patient. Suitable methods and techniques for HLA typing have been described herein. In one embodiment of this disclosure, determining an HLA type of a patient may simply involve collecting a fluid sample from a patient and sending the fluid sample to a laboratory for HLA typing. In another embodiment, determining an HLA type of a patient may involve conducting HLA typing on a fluid sample obtained from the patient. In either case, a goal is to ultimately obtain at least one and preferably many or all HLA types of the patient. As described herein, there are two categories of HLAs in the human body—HLA I and HLA II. Although there are thousands of HLAs in the population, each human has six that contain three main pairs HLAs of Type I;A,B and C and 5 pairs of HLAs of Type II (DP, DM, DO, DQ, and DR). By way of example, HLA typing may be determined using methods such as DNA sequencing, microlymphocytotoxicity assays, or hybridization of DNA to oligonucleotide probes, as described previously. The foregoing are provided as examples only with the understanding that embodiments of this disclosure are not limited to any particular mechanism of determining the HLA type of a patient. Thus, block 1902 of FIG. 19 generally indicates a step of determining an HLA type of a patient.

In some embodiments, determination of an individual's HLA type may involve analyzing a blood sample collected from the individual. Alternatively, determination of an individual's HLA type may include analyzing another biological fluid obtained from the patient. Some disclosed embodiments may involve determining specific disease-related peptides that together with the determined HLA type of the patient, trigger T-cell receptor activation in the patient. Disease-associated peptides may be self-peptides, or non-foreign peptides specific to an individual or foreign peptides that cross-react to self-peptides. As used herein, the term "self-peptide" generally refers to peptides generated from degradation of proteins expressed endogenously in the patient.

As used herein, the term "T-cell receptor" (TCR) generally refers to a protein complex found on the surface of T-cells. Due to genetic recombination, TCRs exhibit remarkable diversity, with each type of T-cell receptor recognizing specific antigen peptides bound to HLA. As used herein, the term "T-cell receptor activation" generally refers to initiation of a signal cascade that activates other components of the immune system in vivo following T-cell receptor binding to an HLA-peptide complex.

Disease-associated peptides may be recognized by T-cells of an individual's immune system and initiate a T-cell attack. For example, disease-associated peptides may be presented by HLA-peptide complexes. In further embodiments, the presented peptides may be subsequently recognized by receptors of T-cells, thereby binding the T-cell receptor to the HLA-peptide complex. In some embodiments, T-cell receptors may only recognize a specific peptide. Alternatively, T-cell receptors may recognize more than one peptide. In some embodiments, T-cell recognition of specific peptides may result in transmission of one or more signals. In further embodiments, T-cell recognition of specific peptides and transmission of signals may result in activation of T-cells specific for those peptides. For example, activation of specific T-cells may initiate a cascade of events, including, but not limited to, differentiation activation and clonal expansion of the T-cells. In certain disease contexts, T-cells may be activated by recognition of an individual's self-peptides, thus causing those T-cells to migrate to and attack particular tissues within the individual.

Disease-associated peptides may be determined in various ways. As will be appreciated by one of skill in the art, determining the identity of the at least one immunogenic peptide may include, for example, procuring HLA-peptide complexes from a biological fluid of a patient, dissociating the peptide from the HLA protein, and analyzing the peptide using methods such as mass spectrometry or Edman degradation. Additionally, such peptides may be compared to a database of antigens to derive relevant information about the peptides. In some embodiments, a peptide's binding affinity for a particular HLA may be measured with methods such as, for example, surface plasmon resonance (SPR) or quartz crystal microbalance analysis (QCMA), or electrochemical analysis, or by means of biosensors. Exemplary procedures involved for determining disease-associated peptides are described above.

As previously described, disease-related peptides may be associated with a variety of diseases, such as autoimmune disease, cancer, or any other disease involving an adaptive cellular immune response, including any one of the autoimmune diseases, cancers (solid tumors and hematological cancers) and post-transplantation complications disclosed herein. For example, disease-associated peptides may be associated with a medical condition involving either the innate or adaptive immune responses of a patient, including autoimmune diseases and cancer. Disease-associated peptides may be associated with the humoral or cellular arms of the adaptive immune response. For example, disease-associated peptides may be associated with any one of the autoimmune diseases, cancers (solid tumors and hematological cancers) and post-transplantation complications disclosed herein, such as leukemia, acute leukemia, myasthenia gravis (MG), Lambert-Eaton syndrome, multiple sclerosis (MS), polycythemia vera (PCV), thrombocytosis, scleroderma, type 1 diabetes, psoriasis, or Crohn's disease. In other embodiments, disease-associated peptides may be associated with at least one of myeloproliferative diseases or viral, bacterial, fungi or parasitic infections.

Consistent with some disclosed embodiments, determining specific disease related peptides may involve identifying at least one immunogenic peptide and comparing it with a database of disease-related immunogenic peptides and their binding affinity for the corresponding HLA type of the patient determined. The database may be populated with information from any source linking peptides and their binding affinity to HLAs, including but not limited to information derived from the literature or information collected based on testing of a plurality of individuals. The database may be maintained locally, may be provided on a remote server accessed via a network, or may be provided by a third party in any manner. As previously mentioned, bioinformatics and big data analytics may be used to predict which of the identified peptides have strong affinities to the HLA's previously identified from analysis of the blood. One example of a bioinformatics database which may be employed in connection with embodiments of this disclosure include the IEDB database available via IEDB.org. Other examples include IMGT (imgt.org) and SYFPEITHI (syfpeithi.de). Such systems may allow a user to make an inquiry to determine the binding affinity of specific peptides to a specific HLA. Determining specific disease related peptides using by comparison with a database need not require access to the database in each instance. For example, a database may be queried in advance and a list of HLA-peptide affinities may be compiled so that the database need not be directly accessed for each query. In this instance, the compiled list may be considered to be its own database for purposes of embodiments of this disclosure.

In some embodiments, the database may be periodically updated based on data obtained from disbursed medical professionals and their patients. For any given target patient, one or more disease-associated peptides may be identified or analyzed and may be quantified. Aspects of this disclosure may also involve extracorporeally exposing blood of the patient to a filter treated with a complex constructed of the disease-related peptide loaded on a construct of the determined HLA, to thereby cause a binding of T-cells with T-cell receptors recognizing the HLA-peptide complex to the filter. Extracorporeal exposure may involve any mechanism of treating blood outside the body. For example, it may occur by drawing blood from a vein of an individual and exposing the blood to a filter, regardless of the particular structure of the filter.

The filter to which the blood is exposed may be treated such that a protein of choice can be connected via chemical reaction (or other mechanism) to a desired surface. The surface may be chemically designed to confer it with specific molecular and chemical properties in order for it to react with the protein. The treatment or disposition may occur when the surface is introduced to a solution including the proteins of interest, preferably in an excess amount to enable maximal saturation of the surface with proteins. By way of example, one or more of the example filters described herein by be employed for this purpose. In a broadest sense, some embodiments of this disclosure are not limited to the specific mechanism of extracorporeal exposure, and hence at block 1906 in FIG. 19, extracorporeal exposure is generally reflected without reference to a particular mechanism or a particular filter.

Consistent with embodiments of this disclosure, a filter may be designed or configured to include an HLA-peptide complex. For example, at least one immunogenic peptide associated with a certain disease may be bound to an HLA protein to form an HLA-peptide complex. In certain embodiments, the HLA protein may be recombinantly produced and the peptide may be synthetically produced. For example, a DNA construct comprising the HLA protein gene sequence may be inserted into a cell expression system, which subsequently expresses the HLA protein of interest. In another example, the peptide may be synthesized by standard procedures, including fluorenylmethoxycarbonyl protecting group chemistry. In other embodiments, both the HLA protein and peptide may be recombinantly produced using standard procedures. Alternatively or additionally, HLA-peptide complexes may be obtained endogenously from an individual, such as a patient.

The HLA protein may be in any form, including monomers and/or multimers. As used herein, the term "monomer" generally refers to HLA proteins which are found in a natural state in the patient, and which bind to a single peptide. As used herein, the term "multimer" generally refers to the linking of several HLA monomers to form a single unit, with each monomer in the unit capable of binding to one peptide. By way of example, each HLA monomer may be linked to a biotin molecule and mixed with streptavidin. As each streptavidin molecule has four binding sites for biotin, a total of four biotinylated HLA monomers may be linked to the streptavidin, thereby forming a tetramer. In another example, each HLA monomer may be linked to an a-helix motif and individual a-helices each linked to an HLA monomer may assemble to form a coiled coil motif, thereby linking multiple HLA monomers to form a multimer. In some embodiments, utilizing HLA multimers may increase the affinity of T-cells for the HLA-peptide complex, as each HLA-peptide unit in the multimer may individually bind to T-cell receptor on the T-cell.

By way of schematic representation, an HLA-peptide pentamer is shown in FIG. 20A. The pentamer is formed when a-helices 204 linked to HLA monomers 2006 bound to peptides 2008 assemble to form a coiled coil motif. The pentamer may further be linked to a fluorophore 2002. FIG. 20B shows an HLA-peptide tetramer. The tetramer is formed by linking a biotin molecule to each HLA-peptide complex and mixing the complexes with streptavidin 2010.

In some embodiments, the HLA proteins may include HLA I and/or HLA II proteins.

In some embodiments, the HLA-peptide complex may be linked to a detectable label. A detectable label may be a marker that enables the HLA complex or components of it to be discerned. Non-limiting examples of detectable labels include a fluorophore, an enzyme, a radioisotope, a heavy metal, or a nuclear magnetic resonance marker or an electrochemical label. Such markers may be associated with the HLA protein and/or the peptide. In some embodiments, the HLA-peptide complex may be linked to more than one detectable label.

By way of schematic representation, FIG. 21A depicts an HLA I protein 2102 linked to a fluorophore 2104. FIG. 21B depicts an HLA II protein 2106 linked to an enzyme 2110 via a peptide linker 2108.

Aspects of this disclosure may involve returning to the patient blood with the bound T-cells removed. The reference to blood being returned to the patient may involve some or all components of blood being returned. For example, after blood is extracted from the patient for treatment, blood components may be separated, and some may be returned to the patient while others may not. Returning blood to the patient, as used herein, encompasses both scenarios. As discussed in other locations herein, blood may be processed in stages and blood separated blood components may be recombined and returned to the patient simultaneously. Alternatively, blood components can be returned sequentially. In a broadest sense, embodiments of this disclosure are not limited to a particular timing or a particular group of blood constituents returned to the patient, as long as some components are ultimately returned. Thus, block 1908 in FIG. 19 generally refers to returning to the patient blood with bound T-cells removed.

In some embodiments, the removed T-cells may include cytotoxic, helper, or memory T-cells. For example, the removed T-cells may include CD4+ or CD8+ T-cells, or both. In some embodiments, the patient's blood may be enriched with materials prior to being returned to the patient. For example, the materials may be nutrients or a pharmaceutical composition, or both.

The disclosed method of extracorporeal filtration and removal of bound T-cells may be performed more than once to a patient during a given year. In certain embodiments, the process may be performed several times to the patient during a given year, depending on the patient's need.

In some embodiments, the filter with bound T-cells may be subjected to standard separation agents in order to enable separation of the bound T-cells from the filter. In certain embodiments, the removed T-cells may be counted. By way of example, separation of the bound T-cells may occur via physical, chemical, or biological means. In preferred embodiments, the separation methods may not damage the separated T-cells or the filter. Any suitable separation agent may be used to remove the bound T-cells. In some embodiments, the T-cells may be counted via fluorescence activated cell sorting (FACS). Generally, any suitable method for counting T-cells may be employed.

Figure 22A:
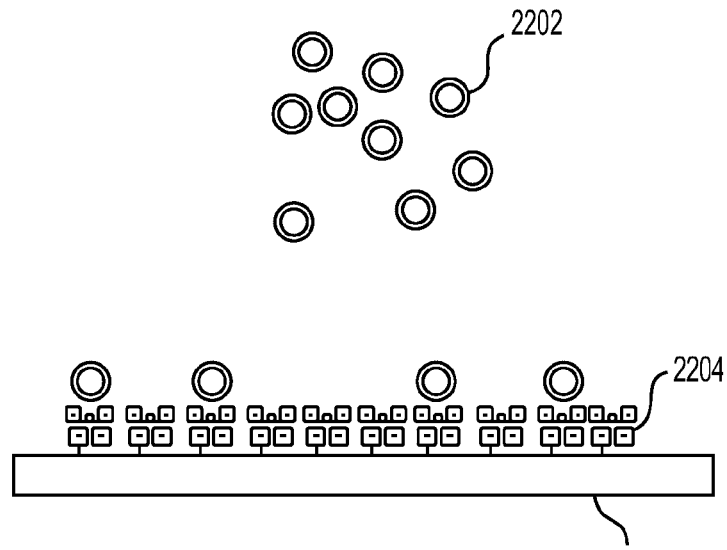
FIG. 22A schematically illustrates a process of removing bound T-cells from the filter, consistent with embodiments of this disclosure.
Figure 22B:
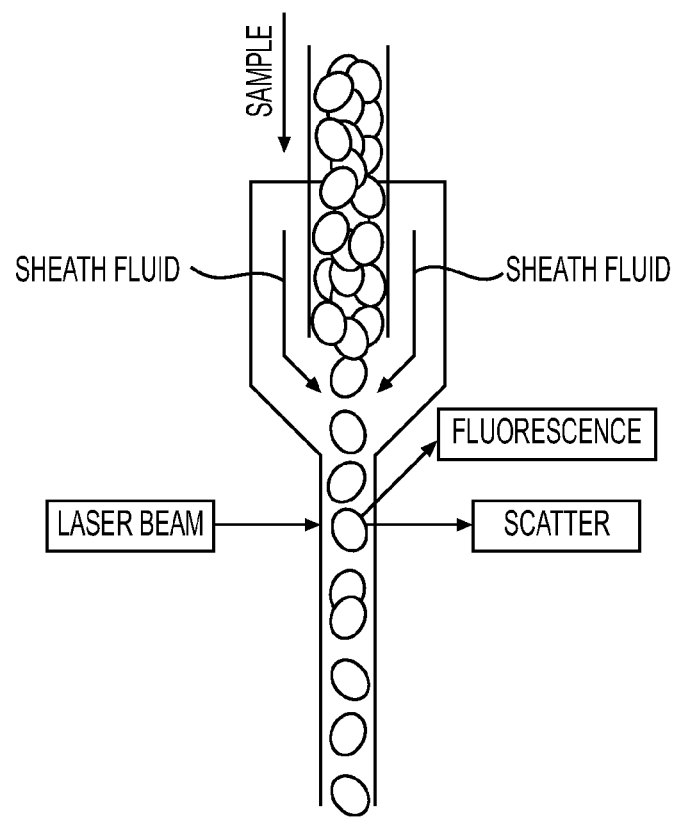
FIG. 22B schematically illustrates a process of fluorescence activated cell sorting, consistent with embodiments of this disclosure.

By way of schematic representation, FIG. 22A shows a process of removing T-cells 2202 from HLA-peptide complexes 2204 disposed on filter 2206. FIG. 22B represents a schematic of the FACS process.

In certain embodiments, the number of T-cells counted may be employed to estimate the progress of a particular disease that depends on a specific T-cell count. For example, if successive counts show a diminution in T-cells counted, such a trend may indicate that the disease is in a form of remission. In some embodiments, the number of T-cells counted may be employed to determine how best to treat a patient suffering from a particular disease. By way of example, the number of T-cells counted may be employed to modify treatment of the patient, such as by modifying the design of a next filter to be used with the patient.

Consistent with this disclosure, an anticoagulant may be administered to a patient. The term anticoagulant refers generally to a blood thinner or any medicine that helps prevent blood clots. Generally, any suitable anticoagulant may be administered to a patient.

Method for Treating a Patient with a T-Cell Associated Autoimmune Disease

The present disclosure relates to methods of treating a patient with a T-cell associated autoimmune disease. It may effectively involve predicting that as a disease triggered by activated T-cells progresses, one or more groups of T-cells that are not yet triggering the disease are likely to do so in the future. Once the prediction is made based on historical data or affinity of certain peptides to certain Human Leukocyte Antigen (HLA) proteins or of others whose disease share similar characteristics, the additional T-cells not yet triggering the disease can be removed before they cause trouble. One example of such a process is reflected at a high level in FIG. 24. This example and others are discussed below in greater detail.

While the present disclosure provides examples of methods of treating T-cell associated autoimmune diseases, it should be noted that the aspects of the disclosure in their broadest sense are not limited to T-cell associated autoimmune diseases. Rather, the foregoing principles may be applied to treat other diseases as well.

The term "treating" refers to undertaking a process in an attempt to improve a medical condition of a patient. Consistent with some disclosed embodiments, this may involve the provision of personalized medicine for patients suffering from a T-cell associated autoimmune disease.

Consistent with disclosed embodiments, a method for treating a patient with a T-cell associated autoimmune disease may involve treating a patient with multiple sclerosis, where T-cells are activatable toward myelin or a non-myelin central nervous system (CNS) protein including an aquaporin channel. Multiple sclerosis is a T-cell associated autoimmune disease where T-cells are activatable to attack proteins of the CNS, resulting in multiple and varied neurologic symptoms. Activation occurs when T-cell receptors on the T-cell recognize a peptide derived from CNS protein. Once the T-cell receptor encounters the peptide, the T-cell goes through an activation process then migrates to the CNS to initiate an immune response. In some cases, T-cells are activated toward myelin, resulting in a demyelination process in the brain and spinal cord. Myelin is a protective sheath that surrounds nerve fibers in the brain, optic nerves, and spinal cord. When the myelin sheath is damaged by these activated T-cells, nerve impulses slow or even stop, causing neurological problems. In some embodiments, the myelin includes at least one of myelin oligodendrocyte glycoprotein (MOG), myelin basic protein (MBP), myelin proteolipid protein (PLP), opalin protein, oligodendrocyte-specific protein (OSP), myelin-associated glycoprotein (MAG), or a combination thereof or other myelin associated protein. Aquaporin channels, sometimes referred to as aquaporins or water channels, are integral membrane proteins from a larger family of major intrinsic proteins that form pores in the membrane of biological cells, mainly facilitating transport of water between cells.

Consistent with some embodiments, a method for treating a patient with a T-cell autoimmune disease may include obtaining HLA-peptide complex data for a particular patient having an autoimmune disorder. The term HLA refers generally to a system or complex of proteins encoded by an individual's major histocompatibility (MHC) gene complex. HLA proteins are typically responsible for regulating an individual's immune system and may be found on the surface of human cells. For example, HLA proteins may function by recognizing foreign, non-self substances in an individual and initiating an immune response to neutralize those substances.

"HLA-peptide complex data" may refer to a characterization of some or all the peptides presented by a specific allele of HLA protein from a patient. Each peptide has different binding affinity to a specific HLA protein.

Figure 23:
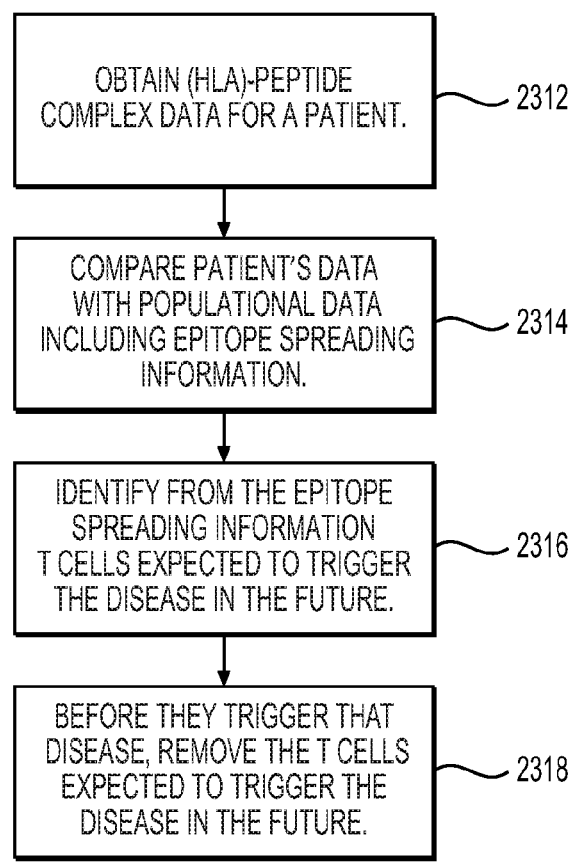
FIG. 23 illustrates in block form various steps of an exemplary method of treating a patient having a T-cell associated autoimmune disease, consistent with embodiments of this disclosure.

HLA-peptide complex data may be obtained through analysis of the particular patient's HLA-peptide complexes and may involve determining the quantity of HLA-peptide complexes in a particular patient. Thus, obtaining as reflected in box 2312 of FIG. 23 may include one or more of performing such an analysis or accessing data of such an analysis previously performed by the same or another party. Quantitative analysis of a patient HLA-peptide complex data may involve construction of a single type of HLA protein line loaded on each one a different peptide. The HLA protein can constitute between 1-100 different myelin or non-myelin peptides loaded separately onto HLA proteins. From 10-100 ml of human peripheral blood mononuclear cells (PBMCs) from a patient may be stained with a fluorescent marker such as carboxyfluorescein succinimidyl ester (CSFE). After washing the marker from the cells, PBMCs may be incubated with HLA proteins anchored to the surface for 15-40 minutes. After washing the PBMCs from the surface, a quantification of number of cells in each HLH different complex may be measured by the intensity of the fluorescent units. The quantification can be measured in any other method such as light reaction. Quantitative analysis of HLA-peptide complex data may also involve direct analysis of stripped peptides that are removed from antigen-presenting cells (APCs) of a patient. Stripping can be executed by mixing the PBMC's with acid solution for different time durations, resulting in a stripping reaction of peptides loaded onto the HLA groove. Then the peptides may be taken for mass spectroscopy analysis, which can determine the sequence or the amount of the peptide.

Obtaining HLA-peptide complex data for the particular patient may involve HLA typing and analyzing associated peptides. HLA typing may be determined through at least one of blood analysis, and peptide analysis may be performed through at least one of cerebrospinal fluid (CSF) analysis or tissue-specific disease related peptide analysis. More specifically, analyzing the associated peptide may include examining cerebrospinal fluid of the particular patient. Stripping analysis can be executed from CSF.

As used herein, the term "analysis of blood" may refer to analyzing whole blood or a fraction of whole blood. A blood fraction may refer to smaller, specific components of blood. In some embodiments, blood fractions may include plasma, white blood cells, red blood cells, serum or any other specific component of blood. As used herein, "CSF" may refer to the clear, colorless fluid found in the brain and spinal cord.

Blood, CSF, or other tissue-specific samples may be obtained from a patient and analyzed. For example, analyzing associated peptides may include stripping peptides from HLA complexes and determining peptide sequences. Peptides may be stripped from HLA complexes by any appropriate means. In some embodiments, peptides may be stripped from HLA complexes by chemical means. Peptides sequencing involves determining the amino acid composition and order of the peptide, and may be performed by means well known in the art. Once such data on a patient is collected it may be stored in a record and thereafter obtained for purposes of carrying out methods consistent with this disclosure.

In connection with some embodiments of this disclosure, obtained (HLA)-peptide complex data may relate to a patient having an autoimmune disorder triggered by first T-cells, and not triggered by second T-cells. In T-cell associated autoimmune disorders, certain T-cell subtypes are activated in earlier phases of the disease, while second T-cell subtypes may be activated in later disease stages. Such second T-cell subtypes may be later activated as a result of earlier attacks by the first T-cell subtypes, exposing more protein structures and recruiting second T-cell subtypes. By way of nonlimiting example, in a comparison of two patients with the same HLA typing, wherein the first is a newly diagnosed patient and the latter is a more advanced patient, the more advanced patient would be expected to have a greater number of activated T-cell subtypes triggering the disease.

In particular embodiments, a method for treating a patient may involve identifying additional T-cell groups that may trigger the autoimmune disorder over time. For example, additional T-cell groups may be identified using HLA typing and associated peptide analysis to anticipate how the disease may progress (e.g., determine T-cell groups that are not triggering the disease today, but which are expected to trigger the disease in the future. While certain first T-cell subtypes may be associated with earlier stages of a disease, and second T-cell subtypes may be associated with later disease stages, the autoimmune disease need not be limited to two associated T-cell subtypes. Identification of three of more T-cell subtypes may be possible through historical analysis of data from patients who exhibited similar HLA typing and peptide analysis.

Once the HLA-peptide complex is obtained for a specific patient, a method of treating the patient may involve comparing the HLA-peptide complex data of the specific patient with HLA-peptide complex data associated with a population of patients having T-cell-associated pathology, wherein the populational data includes epitope spreading information suggesting that persons with autoimmune disorders triggered by the first T-cells, will progress over time to be triggered by the second T-cells. Such comparing is reflected by way of example in block 2314 of FIG. 23. Since autoimmune diseases have unique T-cell-associated pathology, patients with the same autoimmune disease may have similar T-cell-associated pathology over the course of the disease. As a further example, comparing HLA-peptide complex data between the specific patient and populational data may include comparing patients that share mutual HLA types. The populational data may be collected over time from a database that tracks HLA related analysis from a population of individuals. Such information may be stored in a database and may be made accessible to the relevant medical community. By accessing this data, medical practitioners may be able to predict how T-cell activation will evolve in a particular patient.

More specifically, comparing the HLA-peptide complex data of the specific patient with HLA-peptide complex data associated with a population of patients having T-cell-associated pathology may include a comparison of disease-related parameters including years from onset, symptoms and treatment; HLA typing analysis; and analysis of peptides presented by corresponding HLA proteins. By comparing the HLA-peptide complex data of a specific patient with populational data of patients having similar T-cell-associated pathology, it may be possible to determine how advanced the autoimmune disease is for the particular patient and to predict the future epitope spreading for the specific patient.

The term "epitope spreading" refers generally to a diversification of epitope specificity beyond the initial immune response. While autoimmune diseases may have unique epitopes that the initial immune response is directed to, the targeted epitope may spread and diversify to other targets as the disease progresses. This epitope spreading information may be contained in the populational HLA-peptide complex data for a particular autoimmune disease. The time and rate of epitope spreading may vary between autoimmune diseases and patient populations, and may include a number of days, weeks, months, or years. For some autoimmune diseases or populations with HLA-peptide complexes, the epitope spreading may be intramolecular or intermolecular. Intramolecular spreading involves epitope spreading to other sites on the same antigen. Intermolecular epitope spreading involves epitope spreading to other antigens. Epitope spreading information within populational HLA-peptide complex data may suggest whether persons with autoimmune disorders triggered by first T-cells will progress over time to be triggered by second T-cells or additional T-cells. Such an identification of expected epitope spreading is reflected by way of example in block 2316 of FIG. 23.

In some embodiments, before the autoimmune disorder of the particular patient is triggered by the second T-cells (or by additional T-cells), the method may involve removing the second T-cells (or additional T-cells) from the particular patient. Removal of the second T-cells or the additional T-cells may be accomplished by any means available to separate the second T-cells from a biological material. Some non-limiting examples are provided herein, which employ the use of a biological filter to trap the disease-triggering T-cells. In these examples, a patient's blood may be filtered not only for T-cells that currently trigger the disease, but also for T-cells expected to trigger the disease in the future as the disease progresses. Such proactive removal is reflected, by way of example, in block 2318 of FIG. 23.

Figure 24:
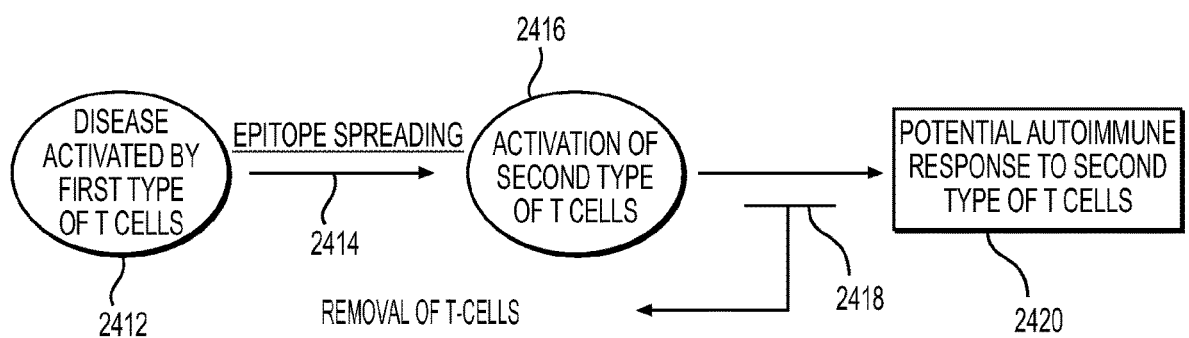
FIG. 24 illustrates a flow chart of a process of removing T-cells consistent with embodiments of this disclosure.

FIG. 24 illustrates an exemplary process of removing second T-cells before they can trigger an autoimmune disorder. As illustrated, after a disease is activated by first type of T-cells at node 2412, epitope spreading at 2414 causes activation and recruitment of a second type of T-cells at node 2416. These second T-cells are capable of either triggering or aggravating an autoimmune response in a patient. However, before the second T-cells can trigger the patient's autoimmune response at node 2420, they are removed from the patient at node 2418.

Removal of the second T-cells may include binding HLA-peptide complexes to T-cell receptors of the second T-cells. Likewise, removal of the additional T-cells may include binding HLA-peptide complexes to T-cell receptors of the additional T-cells.

In some embodiments, the second T-cells and the additional T-cells are removed by a biological filter, such as those described herein. Filters may be constructed to remove a specific type or sub populations of T-cell, or multiple types of T-cells. For example, a single filter might have bound to it multiple HLA complexes for removing more than one type of T-cell. For example, in FIGS. 12A-12D, biological filters may contain differing HLA complexes on a single filter for binding to differing T-cells. Alternatively, filters may be specific to a particular T-cell. In such an embodiment, white blood cells might be circulated through multiple filters in series in order to remove multiple types of T-cells during a single treatment. Thus, for example, in FIGS. 12A-12D more than one filter 1016 may be arranged in series with recirculation loop 1024 recirculating white blood cells from a furthest downstream filter outlet to a furthest upstream filter inlet. Alternatively, a patient may be subjected to multiple treatments each with a different filter for removing differing T-cells.

The method of treating a patient may further involve adjusting the treatment based on identified second T-cells and/or the additional T-cells. The term "treatment" as described previously and particularly in this context may refer to a process of removing pathogenic T-cells from blood. For example, it may refer generally to a process designed for depletion of pathological cells or cell fragments, or at least a reduction in the amount of pathological cells or cell fragments in a patient. Adjusting treatment may involve adapting the pathogenic T-cell removal process in order to facilitate removal of the identified second T-cells and/or additional T-cells. This may involve altering or modifying a biological filter to include HLA-peptide complexes designed to bind T-cell receptors of the second and/or additional T-cells in order to remove them from blood. Adjusting treatment may alternatively or additionally involve implementing other treatment options, such as administering pharmaceuticals or biologics, plasma exchanges, and/or physical therapy.

While in some aspects the method of treating a patient involves removing second T-cells before they can trigger or aggravate the autoimmune disorder of the patient, in some embodiments the method may involve removing the first T-cells and second T-cells simultaneously. Similarly, the method may involve removing the first T-cells and additional T-cells simultaneously. While embodiments of this disclosure may be used to treat a patient with an autoimmune disease triggered by second T-cells or additional T-cells by removing those T-cells from the patient, the first T-cells may also trigger an autoimmune disease in a patient. Therefore, it may be beneficial to remove the first T-cells simultaneously with the second T-cells or additional T-cells. Removal of the first T-cells may be accomplished using similar means as removal of the second T-cells or additional T-cells. For example, removal of the first T-cells may involve binding of HLA-peptide complexes to T-cell receptors of the first T-cells. Additionally, first T-cells may be removed by a biological filter.

Method of Estimating a Number of Pathogenic T-Cells in a Mammal

In some circumstance, such as in the course of tracking the progression of a disease or as part of a process for making a biological filter, it may be helpful to estimate an amount of disease-specific pathogenic T-cells in a patient. Obtaining a general sense of an amount of T-cells that trigger a disease can assist in designing a biological filter for removing those T-cells. And determining a general sense of the amount of pathogenic T-cells in a body at a given time allows the progression of a disease to be tracked. An increase in pathogenic T-cells between determinations tends to indicate that the disease is progressing, while a decrease tends to indicate remission. To this end, some embodiments of this disclosure include a method of estimating an amount of disease-specific pathogenic T-cells in a patient. As used herein, the term "estimating" when referring to estimating a number of disease-specific pathogenic T-cells may include predictions ranging from categorical estimates (e.g., minimal, low, medium, high, extremely high) to rough estimates (e.g., a rough numerical estimate) to more precise numerical estimates. An estimate may be based on a color change, brightness level or an intensity of color, such as may occur through the use of an assay or marker. The estimate may be based on procedures such as fluoroscopy or cell counting (e.g., via machine vision techniques). Estimating may be based on an ex vitro evaluation of a sample removed from a patient. Such a sample may include a blood, cerebrospinal fluid, or any other biological fluid or material. The estimate may reflect a number of T-cell including various T-cell subtypes in a patient or in a sample By way of example, such an evaluation may be based on bringing into contact fresh peripheral blood mononuclear cells (PBMCs) taken from a patient, with certain HLAs with disease-specific proteins and peptides loaded on it. The incubation of these two components (PBMC's and HLA protein complexes) may attract specific T-cells subtypes present in the biological fluid or material.

In accordance with embodiments of the present disclosure, a method of estimating an amount of disease-specific pathogenic T-cells in a patient may include obtaining a first biological fluid sample from the patient. Non-limiting examples of biological fluids are whole blood, serum, plasma, cerebrospinal fluid, synovial fluid, alveolar lavage fluid, pancreatic juice, gastrointestinal lavage fluid, peritoneal lavage, lymph, bone marrow, amniotic fluid, semen, pleural fluid, breast milk, pericardial fluid, saliva, feces, bile, and urine.

Figure 25:
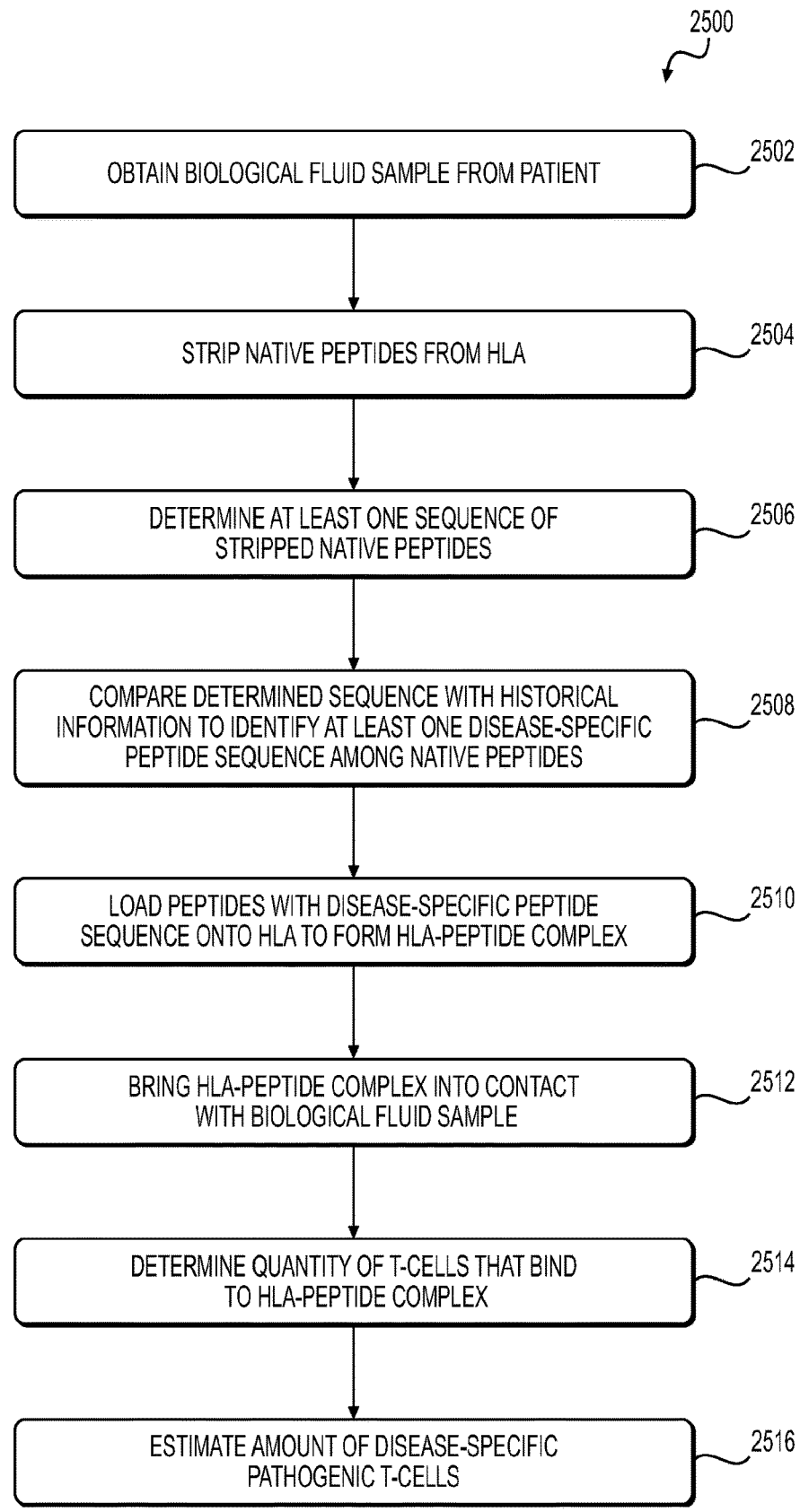
FIG. 25 is a block diagram illustrating a method for estimating pathogenic T-cells in a patient, consistent with embodiments of this disclosure.

Obtaining biological fluid from a patient may include, for example, aspiration and/or drainage with devices such as a needle or catheter that may be connected to a collection container or a tubing set. Such methods and techniques may be employed with biological fluids such as whole blood, cerebrospinal fluid, synovial fluid, alveolar lavage fluid, peritoneal lavage, lymph, or bone marrow. However, biological fluids such as gastrointestinal lavage fluid and urine might be obtained non-invasively by collection when the fluids are excreted from the body. Embodiments of the present disclosure, in their broadest sense, are not limited to a specific type of biological fluid or a specific manner of obtaining a biological fluid sample. Thus, block 2502 in the exemplary method 2500 of FIG. 25, indicating that a sample is obtained, is not so limited. For example, a sample may be obtained simply by receiving it from another who collected the sample.

The patient in which the number of disease-specific pathogenic T-cells is estimated may be afflicted with an autoimmune disease, cancer, or a post-transplantation complication or condition described herein. For example, the disease may be multiple sclerosis, type 1 diabetes, myasthenia gravis, and Crohn's disease. As the goal behind obtaining the biological fluid is to identify the disease-specific peptides or antigen peptides that are recognized by the pathogenic T-cells, it may be desirable to obtain a biological fluid that is localized at the pathological site, or a biological fluid that is within close vicinity of the pathological site (e.g., within 10-20 mm of the pathological site). For example, if the patient is an MS patient whose central nervous system is afflicted, an appropriate choice of the biological fluid might be cerebrospinal fluid, but is not so limited. If the patient has Crohn's disease afflicting the bowel system, an appropriate choice of the biological fluid might be gastrointestinal lavage fluid, but is not so limited.

Disclosed embodiments may also include stripping native peptides from a first group of human leukocyte antigens (HLAs) in the first biological fluid sample. Stripping the native peptides that are bound to the patient's HLAs may be accomplished in several different ways, including protein chemistry techniques such as altering the pH value of the biological fluid in order to disrupt the interactions between the peptides and the HLAs, denaturation of the peptides using agents such as DMSO. As an example, after the biological fluid sample has been obtained from the patient, the cells in the sample may be separated, for example, by centrifugation after which the cell fraction may be collected as a pellet. The collected cell fraction may be reconstituted in a suitable buffer prior to lysis. Various cell lysis techniques may be used, such as mechanical disruption (e.g., French press), liquid homogenization, high frequency sound waves (e.g., sonication), freeze/thaw cycles and manual grinding, and chemical lysis (e.g., with sodium dodecyl sulfate or SDS). The cell lysis procedure may result in the disruption of the cell membrane in order to release the proteins within the cell, including the native peptides that are bound to the HLAs.

Next, the HLA-native peptide complexes may be isolated from the pool of proteins using techniques such as fast protein liquid chromatography (FPLC), high-performance liquid chromatography (HPLC) where the protein mixture is fractionated into individual proteins based on characteristics such as polarity, charge, hydrophobicity, molecular weight or affinity to a specific ligand. Alternatively, the HLA-native peptide complexes may be isolated using immunoprecipitation. Immunoprecipitation may be performed, for example, by introducing into the protein mixture antibodies known to bond to HLA complexes. Such antibodies may include, for example, Anti HLA antibodies, anti HLA type 1 antibodies (A, B and C), anti HLA type 1 A antibodies, anti HLA type 2 antibodies (DR, DP, DQ), anti HLA DR antibodies, anti HLA DRb15:01 antibodies and others that facilitate immunoprecipitation. Accordingly, immunoprecipitation results in the separation of a mixture of various HLAs and various bound native peptides from the rest of the proteins and peptides released from the cells.

The removal of the native peptides from the HLAs may be done selectively in order to preserve the integrity of the HLAs that are later used in the method, for example the interactions between the peptides and the HLAs are disrupted due to changes to the chemical properties of the peptides only but not the HLAs, and only the peptides but not the HLAs are denatured. Alternatively, the removal of the peptides from the HLAs may be done universally and the original properties of the HLAs are later restored. The removal of the native peptides from the HLAs may result in a mixture of pathogenic and non-pathogenic peptides. As generally reflected in block 2504 in FIG. 25, native peptides may be stripped from HLAs. Because there are many ways to strip peptides from HLAs and this disclosure is not limited to any particular process, stripping in block 2504 is no limited to any particular process.

Some disclosed embodiments may include determining at least one sequence of the stripped native peptides. Sequences of the native peptides stripped from HLAs in may be determined by peptide sequencing techniques such as mass spectrometry and Edman degradation using a protein sequenator (sequencer). Sequencing may result in a unique code or identifier for each peptide. In other embodiments, the HLA-peptide complexes may be derived endogenously from the patient. In a broadest sense, disclosed embodiments are not limited to a particular method of performing the sequencing. Thus, in block 2506 of FIG. 25, determining at least one sequence is not limited to a particular method of sequencing. Indeed, determining at least one sequence, as used herein, includes sending a sample to a lab that returns sequence results, regardless of the processes used in the lab. Typically, but not always, many different peptides may be stripped from HLAs and their sequences determined.

Some disclosed embodiments may include comparing the determined at least one sequence with historical information to identify at least one disease-specific peptide sequence among the native peptides. A peptide with a "disease-specific sequence" refers to any peptide, whether or not currently known, that has an impact on a disease. Such peptides might already be known to impact a disease, or knowledge of impact may be identified in the future through bioinformatics or other analysis. In addition, a peptide with a disease specific sequence includes peptides whose sequences are not yet known but are later identified. As previously mentioned, each peptide may have its own unique sequence, reflected for example as a code or other identifier. The sequences of the native peptides may then be compared with historical information. As used herein, "historical information" may include any data reflecting previously identified structures or relationships. For example, bioinformatics and big data analytics may be used to match sequenced native peptides with peptide sequences historically know to correlate to a disease.

For example, such analyses may match native peptides with known reference sequences associated with a protein linked to a disease (e.g., myelin related proteins for MS) or other information such as disease symptoms that are known to be associated with the sequence. To compare the at least one sequence of the stripped native peptides with reference sequences in order to identify at least one disease-specific peptide sequence among the native peptides, bioinformatics tools such as NCBI BLAST (https://blast.ncbi.nlm.nih.gov/Blast.cgi) or any other algorithms and programs for comparing primary biological sequence information may be employed. These sources may contain the amino-acid sequences of proteins or peptides. By comparing one or more query amino acid sequences with a library or database of reference amino acid sequences and identifying library sequences that resemble the query sequence above a certain threshold, a match may be determined. As used herein, the term "reference sequences" refers to the biological sequence information of known disease-specific peptides. Block 2508 of FIG. 25 generally indicates the comparison of a determined sequence of a native peptide with historical information. Because, as previously discussed, there are many ways to undertake a comparison, block 2508 does not specify a particular way. In a broadest sense, comparing may occur by sending the determined sequence(s) to a third-party vendor for analysis.

Some disclosed embodiments may involve loading onto a second group of HLAs, a plurality of peptides sharing the at least one disease-specific peptide sequence to form a plurality of HLA-peptide complexes. A peptide with a "disease specific sequence" refers to any peptide, whether or not currently known, that has an impact on a disease. Such peptides might already be known to impact a disease, or knowledge of impact may be identified in the future through bioinformatics or other analysis. In addition, a peptide with a disease specific sequence includes peptides whose sequences are not yet known but are later identified. The peptides that are loaded may, for example, be selected as the top pathogenic peptides identified during the comparing process described previously. Methods and techniques involved in loading peptides onto HLAs are described herein and are not mentioned again to avoid repetition. The second group of HLAs may be the same as the first group or may be a different group. Copies of the disease-specific peptides that are loaded may be recombinantly produced using molecular biology methods and techniques. In some embodiments, the HLA-peptide complexes include a plurality of synthetically or recombinantly produced peptides sharing the at least one disease-specific sequence. In other embodiments, the HLA-peptide complexes may be obtained endogenously from the patient. In a broadest sense, disclosed embodiments are not limited to a particular mechanism of loading peptides onto HLAs. Thus, in block 2510 of FIG. 25, loading is generally indicated without reference to any particular loading mechanism.

Some disclosed embodiments may further include bringing the plurality of HLA-peptide complexes into contact with a second biological fluid sample. For example, the HLA-peptide complexes may be bound to or otherwise deposited on a medium such as one or more test strips or surfaces, with each different HLA-peptide complex located in a separate area. A biological material such as blood, cerebrospinal fluid, or any other material disclosed herein may be stained on the test areas. Alternatively, a biological fluid may be flowed over the test areas. This may result in T-cell receptors in the biological material to bind to HLA-peptide complexes in the test areas. The amount of T-cells that bind may be a function of the binding affinity of the particular T-cell to a particular HLA-peptide complex. Because a biological sample may be brought into contact with the HLA-peptide complex in various ways, 2512 in FIG. 25 generally refers to contact without specifying a particular method of contact. In a broadest sense, the bringing into contact can be outsourced to a lab consistent with the meaning of the phrase "bringing into contact" as used herein.

Disclosed embodiments may also include determining, for the plurality of HLA-peptide complexes brought into contact with the second biological fluid sample, a quantity of T-cells that bind to the plurality of HLA-peptide complexes. As previously discussed, the binding affinity of HLA-peptide complexes to TCRs may be revealed by a quantity of T-cells that bind to particular HLA-peptide complex test areas. An amount of T-cells that bind to each area may be quantified in a number of ways. Cells may be counted for more precise quantification or markers can be used to generally indicate an amount of bound T-cells by color indicators or intensity measurements. Many ways of quantifying an amount of cells are usable, and therefore block 2514 of FIG. 25 generally refers to determining without specifying a specific mechanism. In a broadest sense, determining may simply involve sending materials to a third-party vendor for analysis.

In some embodiments, based on the determined quantity of T-cells that bind to of the plurality of HLA-peptide complexes, an amount of disease-specific pathogenic T-cells may be estimated in a biological fluid volume within the patient. For example, in a general sense, the amount of bound T-cells on the previously described test area may serve as a general indicator of the amount of disease specific T-cells in the patient's blood, cerebrospinal fluid, or other body fluid or material. Estimating, as used herein, encompasses both categorical estimates and numerical estimates. A categorical estimate includes indicators such as high or low. Numerical estimates may provide an estimated quantification, such as a number or volume. Such estimates may be derived from an amount of T-cells detected in a test area. That amount may be extended, through correlation to estimate an amount of T-cells in a patient's biological fluid volume. Generally, estimating is reflected in block 2516 of FIG. 25, and encompasses all forms of categorical and numerical estimations, regardless of how performed. Sending materials to a third party who performs some or all of the process of estimation falls within the scope of estimating, as that term is used herein.

In some disclosed embodiments, a quantity of T-cells that bind to the plurality of HLA-peptide complexes have a plurality of peptides sharing the at least one disease-specific peptide sequence. In another embodiment, the quantity of T-cells that bind to the plurality of HLA-peptide complexes include a plurality of peptides sharing a plurality of disease-specific peptide sequences.

Disclosed embodiments may also include HLAs that may be linked to a detectable marker, in order to be detected and quantified. Examples of suitable detectable markers include at least one of a fluorophore, an enzyme, a radioisotope, a heavy metal, and a nuclear magnetic resonance marker.

Methods of estimating an amount of disease-specific pathogenic T-cells in a patient may also be varied by incorporating one or more steps in addition to the steps described above. For example, bioinformatics and big data analytics, such as the Immune Epitope Database and Analysis Resource (iedb.org), may be used to predict which of the identified disease-specific peptides have strong affinities to the HLA's in a patient's biological fluid sample that have been isolated and identified, and to determine the binding affinity of the specific peptides to a specific HLA. A list of disease-specific peptides predicted to have strong affinities to a patient's HLAs and their respective predicted binding affinities may be created for specific HLA-peptide pairs and/or for different combinations of the HLAs and disease-specific peptides. When building a biological filter as discussed further below, focus may be placed upon HLA-peptide complexes with binding affinities that are above a threshold e.g., top 10 HLA-peptide complexes. Accordingly, an exemplary method of estimating an amount of disease-specific pathogenic T-cells may further include a step of measuring, estimating, or predicting a binding affinity of each of the plurality of HLA-peptide complexes for the disease-specific pathogenic T-cells prior to determining the quantity of T-cells that bind to the plurality of HLA-peptide complexes. Measuring or estimating actual binding affinities may be performed using techniques like Surface Plasmon Resonance (SPR) & Quartz Crystal microbalance Analysis (QCMA) or sensors based on QCMA concept or Enzyme Linked Immuno-Sorbent Assay (ELISA).

Another exemplary method of estimating an amount of disease-specific pathogenic T-cells may further include a step of validating that correct disease-specific pathogenic T-cells are bound to the plurality of HLA-peptide complexes. The validation may be done, for example, by removing the bound disease-specific peptides from the HLA-peptide complexes and having the peptides sequenced (most accurate), or evaluating the molecular weight of the bound disease-specific peptides (e.g. mass spectrometry, light scattering techniques (SLS, MALS) or SDS-PAGE electrophoresis) and comparing the molecular weight measured to the known molecular weight of the correct disease-specific peptides.

According to some disclosed embodiments, a method of estimating an amount of disease-specific pathogenic T-cells may further include an evaluation of the progress, state, or status of the patient's disease, or an evaluation of the efficacy of a treatment regimen or how well the patient is responding to the treatment regiment, based on the estimated amount of disease-specific pathogenic T-cells. As an example, a method of estimating an amount of disease-specific pathogenic T-cells may further include a step of assessing a status of a disease based on the determined quantity of T-cells that bind to the plurality of HLA-peptide complexes. In one embodiment, assessing the status of the disease may include comparing the determined quantity of T-cells that bind to the plurality of HLA-peptide complexes with a quantity of T-cells determined from a population of patients having the disease. Another exemplary method of estimating an amount of disease-specific pathogenic T-cells may further include a step of assessing efficacy of a treatment regimen of a disease by comparing the determined quantity of T-cells that bind to the plurality of HLA-peptide complexes and a previously determined quantity of T-cells that bind to the plurality of HLA-peptide complexes. Such an assessment is beneficial in that the treatment regimen may be adjusted in accordance with the needs of the patient. For example, if the quantity of T-cells bound to the HLA-peptide complexes has not decreased, adjustments may be made to the treatment regimen by increasing the dosage of a drug or to change to a new treatment regimen altogether. Alternatively, if the quantity of T-cells bound to the HLA-peptide complexes has successfully decreased, the dosage of a drug may be reduced, or the treatment regimen may be terminated altogether. Accordingly, some disclosed embodiments may include adjusting the treatment regimen based on the comparison of the determined quantity of T-cells that bind to the plurality of HLA-peptide complexes and the previously determined quantity of T-cells that bind to the plurality of HLA-peptide complexes.

In yet another example, a method of estimating an amount of disease-specific pathogenic T-cells may further include manufacturing a biological filter containing the plurality of HLA-peptide complexes. Manufacturing a biological filter may include, for example, synthesizing a plurality of peptides sharing the at least one disease-specific sequence, using, for example, techniques described herein. Manufacturing a biological filter may further include, for example, synthesizing HLAs, mixing the synthesized HLAs with the synthesized plurality of peptides sharing the at least one disease-specific sequence to form synthetic HLA-peptide complexes, and applying the synthesized HLA-peptide complexes to an inert surface medium of the biological filter. Methods and techniques involved in applying or anchoring the HLA-peptide complexes to the inert surface medium of the biological filter are described above. As discussed above, various HLA-peptide combinations that capture T-cells may be identified, and their binding affinities may be measured, estimated, or predicted. Based on the binding affinities, the HLA-peptide complexes having highest binding affinities to the disease-specific pathogenic T-cells may be synthesized to be incorporated in the filter.

In certain embodiments, prior to manufacturing a biological filter, a test kit may be provided. The test kit may include a test strip, where each HLA-peptide complex (all different combinations) may be anchored to a different area of a test surface (or to different test surfaces) such as glass or silicon. Preferably, only one HLA-peptide complex type may be anchored on each surface region or area of surface such that each region may contain a unique HLA peptide complex. This enables testing of the HLA-peptide complexes that are most relevant to a particular patient. A biological fluid such as blood may be used to stain each area, causing the binding of T-cells to the associated HLA-peptide complexes. The bound T-cells in each area may then be counted or estimated using, for example, an automated spectrophotometer reader.

As described above, the methods and systems of this disclosure may be used on patients with a host of diseases, including diseases including autoimmune diseases, cancers, and post-transplantation complications or conditions, including one of these diseases and conditions disclosed herein. In a particular embodiment, the patient may have multiple sclerosis, and the at least one disease-specific peptide sequence is a sequence of a peptide derived from myelin associated protein. In another embodiment, the patient may have type 1 diabetes, and the at least one disease-specific peptide sequence may be a sequence of an insulin peptide or other protein associated with beta cell proteins. The patient may have myasthenia gravis, and the at least one disease-specific peptide sequence may be a sequence of an acetylcholine receptor peptide. In another embodiment, the patient may have Crohn's disease, and the at least one disease-specific peptide sequence may be a sequence of a gastrointestinal tract peptide, which may be derived from the liver, pancreas, colon, rectum, stomach, gallbladder, or small and large intestines.

EXAMPLES

Overview of Examples 1-7

Figure 27:
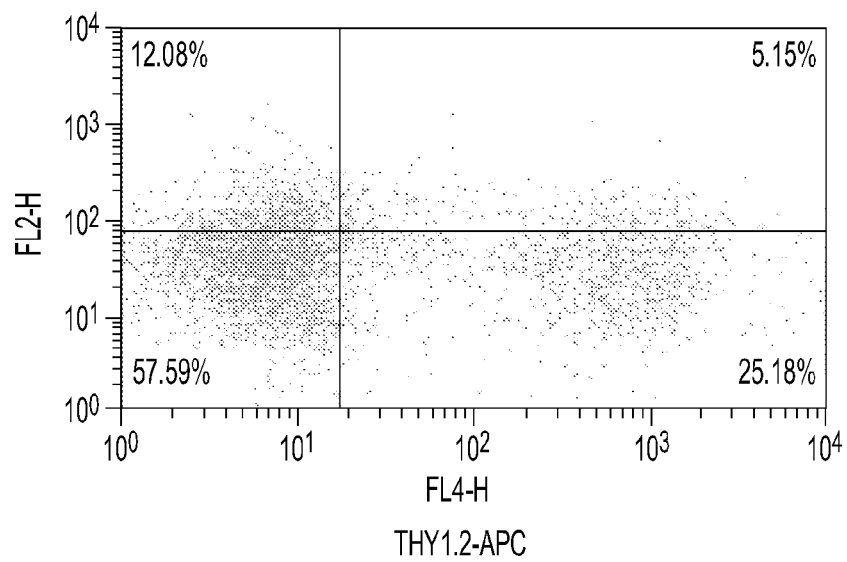
FIG. 27 is a FACS histogram illustrating a double staining of MOG-activated T-cells with T-lymphocyte marker (Thy1.2-APC) before separation and staining for proteins already conjugated to PE (proteins –PE), consistent with disclosed embodiments.

Experiments described in Examples 1-7 were designed to demonstrate the proof of concept in a Multiple sclerosis (MS) mouse model, i.e., the ability of the proteins to recognize and capture a certain population of T-cells that cause demyelination from an extract of various WBCs in a solution, and to be able to measure the quality of such separation. In FIG. 27, the right upper quadrant (RUQ) that was stained, which represented percentage of T-cells that recognized the peptide MOG, was 5.15%. This fraction represents the number of T-cells whose receptors recognize the peptide MOG, and it is relatively low. Under normal conditions, one clone of T-cells constitutes a very small portion of the entire population of T=cells (Lythe et al. J. Theor. Biol., 2016, 389:214-224). However, the presence of MOG in the proliferation assay helped to receive higher percentages of T-cells that recognize MOG, and hence the percentage in FIG. 27 is 5.15%.

Figure 28A:
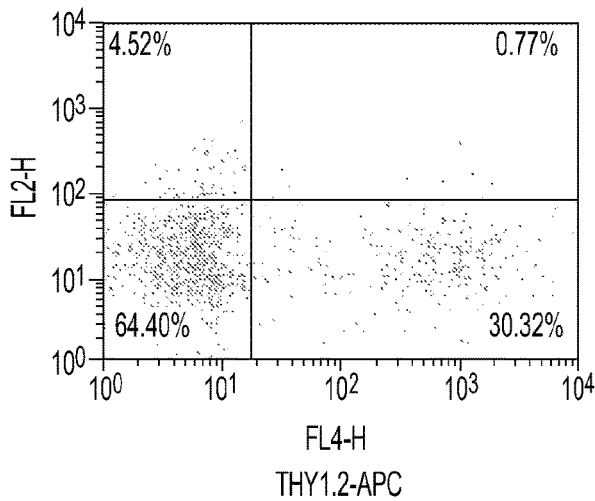
FIGS. 28A and 28B are FACS histograms illustrating the number of MOG-activated T-cells that did not attach to the column after separation from the protein complex, consistent with disclosed embodiments.
Figure 28B:
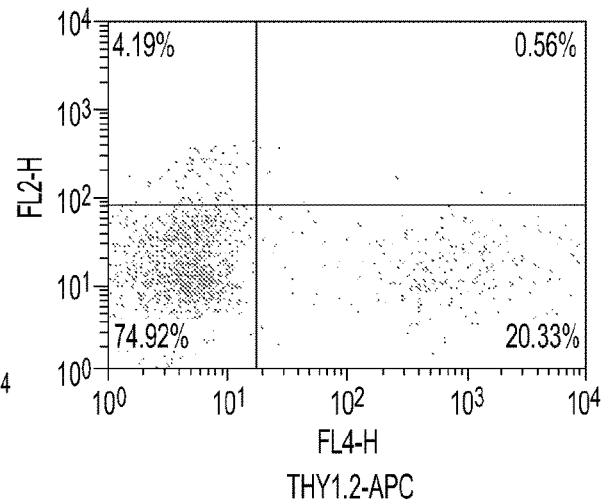

Following the recognition and the separation procedure, opposing trends were observed—a decrease in the fraction of the specific T-cells in the mixture of cells that did not bind to the protein complexes (commercially available HLA-tetramers), and, in contrast, an increase in the fraction of these specific harmful T-cells in the cell population that binds to these protein complexes. These results are presented in FIGS. 28A-28B and FIGS. 29A-29B. In FIGS. 28A-28B, RUQs have declined significantly from 5.15% to 0.77% and 0.56%. In contrast, in FIGS. 29A-29B, which examine the cell population inside the columns, the percentage of specific T-cells within the column after the first separation is 5.82% (see FIG. 29A RUQ). This number is very close to the percentage obtained in FIG. 27 (5.15%), therefore demonstrating that even in one separation the entire amount of the harmful T-cells was obtained and proving that the formed protein-T-cells were stable. This set of results establishes that the proteins used in the procedure recognized and captured specific T-cells from various cell populations, and with very high efficiency. The results establish that the proteins used in the procedure are highly specific and efficient in recognizing and capturing the specific pathogenic T-cells from various populations of WBCs. This specific removal of T-cells prevented Experimental Autoimmune Encephalitis in the treatment group.

Example 1: Induction of Experimental Autoimmune Encephalitis (EAE) in Mice

A model of Experimental Autoimmune Encephalitis (EAE) in mice. EAE in mice is a widely used animal model that imitates MS in humans. EAE was induced in six mice at the age of 6-7 weeks, by injecting a myelin component called MOG, emulsified in complete Freund's adjuvant, and Pertussis toxin given at day of induction and 48 hours later. The injection of MOG induces specific T-cells that are capable of producing neurological deficits resembling the signs of MS in humans. 9 days later, the abdominal lymph nodes were removed and white blood cells (WBCs) were produced. The cells were co-cultured with specific cytokines: IL-2, IL-12, and IL-23 in the presence of MOG during three days in a CO2 incubator at 37° C. The cytokines and MOG act together as proliferation factors for the T-lymphocytes that recognize only MOG.

Example 2: Adoptive Transfer of EAE

The proliferating cells from the previous step were divided to two groups: 1. Cells without separation (as is); and 2. Cells following the separation of the harmful T-cells, using the following procedure:
  a. Incubation with the targeting proteins, which are bound to a fluorochrome molecule, PE.
  b. Adding to the cells magnetic beads that recognize the fluorochrome molecule, PE. This step resulted in a complex of PE-proteins-T-cells-magnetic-beads.
  c. The complex from b. was then passed within a column, to which only the PE-proteins-T-cells-magnetic-beads will bind. This procedure was repeated twice.

Cells from Group 1 were injected to three mice (control group), and cells from Group 2 were injected to three mice (treatment group). The harmful cells were separated and deleted from Group 2.

Figure 26:
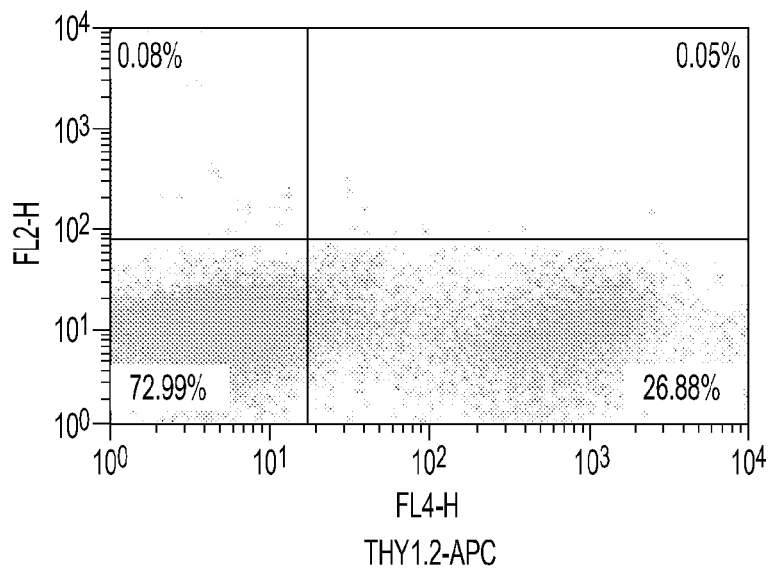
FIG. 26 is a FACS histogram illustrating a single staining of T-cells in lymph nodes with Thy1.2 after in vitro incubation, consistent with disclosed embodiments. A positive staining for Thy1.2 (LF4-H) is shown on the right lower quadrant (26.88%).

Example 3: Evaluation of the Number of T-Cells in Lymph Nodes Following In Vitro Incubation There are various populations of WBCs within the lymph nodes, such as B cells and macrophages. A flow cytometry analysis machine was used for recognition of the cells. Thy1.2, a unique marker for T-lymphocyte only, was used in order to estimate the percentage of Tlymphocytes in the extract. FIG. 26 illustrates the results using single staining with Thy1.2. Positive staining for Thy1.2 (LF4-H) appears in the right lower quadrant of the graph. Thus, 26.88% of the cells in the extract were found to be T-lymphocytes. Non-T-lymphocytes cells appear in the lower left quadrant (72.99%). The left and right upper quadrants are irrelevant, as this staining was done before adding PE-proteins. The cells examined were WBCs within the lymph nodes before the first separation by the column.

Example 4: Evaluation of the Number of MOG-Activated T-Cells Before Separation Next, the cells were double stained with the same T-lymphocyte marker (Thy1.2-APC) as in FIG. 26, and a second marker that binds proteins that are already conjugated to PE (proteins-PE). Cells that were double stained appear in the right upper quadrant of FIG. 2. The cells examined were white blood cells within the lymph nodes before the first separation by the column. As can be seen in FIG. 2, 5.15% of the cells are double stained, i.e. T-lymphocytes that are connected to the proteins. Staining in the left upper quadrant (12.08%) represents positive staining of the proteins only.

Example 5: Evaluation of the Number of MOG-Activated T-Cells after Two Separations Next, the cell population was analyzed within the column, using the MOG-PE complex for isolating specific T-cells. The protein complex was run through the column twice (FIG. 28A: first time; FIG. 28B: second time), in order to monitor the efficiency of the separation. In each of these two runs, a new column was used, and the cell fraction running through the column was analyzed (i.e. the fraction that does not bind to the column). Double stained cells retained by the magnetic beads in the column were subjected to flow cytometry analysis, with results illustrated in FIGS. 28A and 28B

Example 6: Evaluation of the Number of MOG-Activated T-Cells within the Column (Two Separations)

Figure 29A:
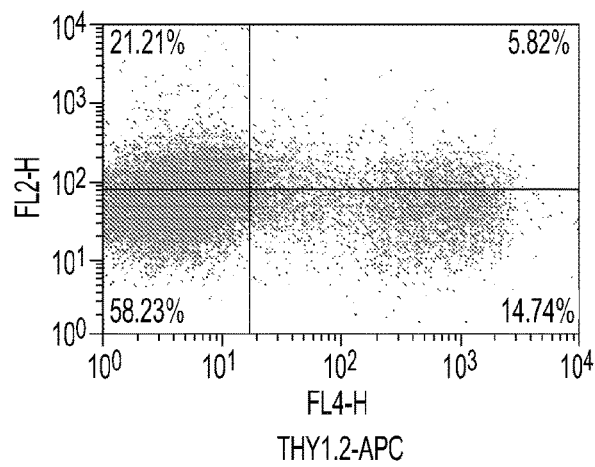
FIGS. 29A and 29B are FACS histograms illustrating the number of MOG-activated T-cells binding within the column after separation with the protein complex, consistent with disclosed embodiments.
Figure 29B:
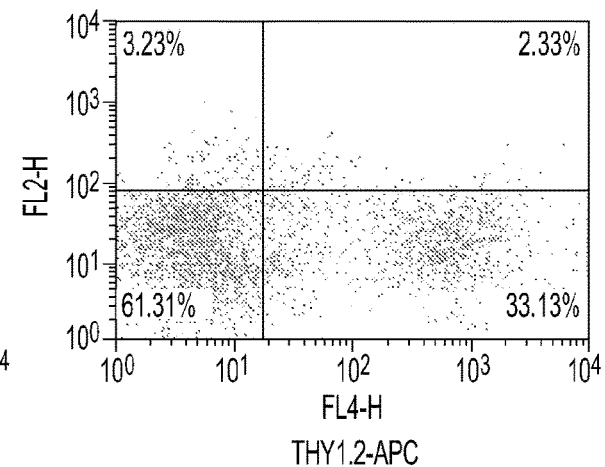

The cell population binding to the column was also analyzed, following the same procedure for the isolation of specific T-cells. As described above, the complex was run through the column twice (FIG. 29A: first time; FIG. 29B: second time). FIGS. 29A and 29B show the results for cells within the first column (FIG. 29A), and cells within the second column (FIG. 29B).

Example 7: Pre-Clinical Results

Nine days after the injection of cells to healthy mice, the scores in two groups were:

Control Group 1: The three mice received the following clinical scores: 1, 1, and 1.5 (see Table 1, below, for details on the scores). The mean clinical score was 1.2.

Treatment Group 2: Three mice that had received cells following the deletion of harmful T-cells: 0, 0 and 0 (see Table 1, below, for details on the scores. The mean clinical score was 0.

Important note: It was known in advance that EAE induced with MOG and then transfer of the cells to healthy mice would not yield a full-blown disease, but rather a milder form of a disease. This is the reason that higher scores of the disease in Control Group 1 could not be observed.

TABLE 1

Experimental Autoimmune Encephalomyelitis (EAE) evaluation of clinical signs

| Score | Signs | Description |
|---|---|---|
| 0 | Normal behavior | No neurological signs. |
| 1 | Distal limp tail | The distal part of the tail is limp and droops. |
| 1.5 | Complete limp tail | The whole tail is loose and droops. |
| 2 | Righting reflex | Animal has difficulties to return on his fee twhen it is laid on his back |
| 3 | Ataxia | wobbly walk-when the mouse walks the hind legs are unsteady |
| 4 | Early paralysis | The mouse has difficulties standing on its hind legs but still has remnants of movement. |
| 5 | Full paralysis | The mouse cannot move its legs at all, it looks thinner and emaciated. Incontinence |
| 6 | Moribund/Death | |

Example 8: Observational Clinical Study in MS Patients

The purpose of the study was to characterize and quantify special sub-population of white blood cells (WBCs in MS patients in comparison to subjects free of MS and other autoimmune diseases.

The primary objective of the study was to establish a pilot database of MS patients, to determine their HLA type and their unique MS related presented peptides repertoire. The dataset was accumulated in order to enable the design of a unique biological probe, able to recognize and capture specific WBCs from patients collected blood and quantify the specific MS-related WBCs collected from each patient.

Blood collection: Total of 60 patients (20 newly diagnosed and 30 known MS patients along with 10 subjects free of MS and other autoimmune diseases) that were found to be eligible were invited to participate in the study. All three groups attended at least one visit and when blood was drawn, blood samples were sent to a tissue typing laboratory for HLA typing and for preservation of cells for in-vitro assays according to protocols as described and approved by an Ethics Committee. The HLA genotyping results were documented, and the abundance of each HLA genotype was calculated.

PBMCs purification: Upon arrival of the blood samples at the research laboratory, the samples were used for either PBMCs separation and purification or as a whole blood for filtration procedures. A peripheral blood mononuclear cell (PBMC) is any peripheral blood cell having a round nucleus. These cells consist of lymphocytes (T-cells, B cells, NK cells) and monocytes, whereas erythrocytes and platelets have no nuclei, and granulocytes (neutrophils, basophils, and eosinophils) have multi-lobed nuclei. In humans, lymphocytes make up the majority of the PBMC population, followed by monocytes, and only a small percentage of dendritic cells. PBMCs were extracted and purified using UNISEP tubes (Novamed, Israel) standard protocol and stored in serum free freezing medium (Biological industries, Israel) at −80° C. for future analysis.

Overview of Examples 9-12

Examples 9-12 describe the construction, expression, purification, and characterization of the proteins responsible for recognizing, capturing, and removing pathogenic T-cells.

Example 9: In Silico Construction of Proteins

Sequence alignment of MHC class II molecules from human, rat, and mouse species provided a starting point for protein studies described herein. As previously described (Burrows et. al., Protein Eng., 1999, 12(9):771-778; Chang et. al., J. Biol. Chem., 2001, 276(26):24170-24176) expression vectors for human, rat and mice pathogenic cell-removing proteins were designed.

Each protein was designed specifically according to the future experimental animal model and its genetic background (strain). For the human recombinant protein (BI2.002), the HLA class II: DRB*1501 β1 subunit fused to DRA*0101 a1 subunit was used as it is one of the most common alleles in MS patients. For mice (BI4.001) and rat (BI3.002), the homologue sequence to the human DR1501: 0101 sequence: C57 BL6 MHC class II I-Ab β1α1 subunits and MHC class II RT1I β1α1 (correspondingly) was used.

A 30-amino acid huMBP-(85-99)-peptide, followed by a linker sequence, cartridge was also inserted into the β1α1 coding sequence between Arg-5 and Pro-6 of the β1 chain. Lastly, the inventors added 9 nucleotides encoding to 3 amino acids: two Glycine and Cysteine in the C-terminus of all 3 proteins.

The genes encoding for the BIX.XX-GGC protein were cloned into the NcoI/XhoI restriction sites of pET21d (+) expression vector synthetically by Genescript (USA) and transformed into BL21(DE3)-competent expression host (BioLab).

Example 10: Expression and In Vitro Folding

The pET21d+/BIX.XX-GGC vectors were transformed into the E. coli BL21(DE3) competent cells (BioLab, Israel) for protein expression. Recombinant protein production was induced by the addition of isopropyl b-D-thiogalactoside (IPTG) (BioLab, Israel) and harvested by centrifugation.

Proper folding of the pathogenic cell-removing proteins required the formation of disulfide bonds. Protein that requires disulfide bonds for proper folding tend to form aggregates also known as inclusion bodies. Protein aggregates in the bacterial cytosol are formed due to the reducing environment in the cytosol in which disulfide bonds tend to be unstable. In order to extract the pathogenic cell-removing proteins, the cell pellets were lysed using a microfluidizer and the non-soluble inclusion bodies that contain the pathogenic cell-removing proteins were sedimented by centrifugation.

The pellet containing misfolded protein was denatured and purified using protein chromatography anion exchange (AIEX) column and refolded in a slow multistep dialysis process. The final yield of purified protein varied between 15 and 30 mg/liter of bacterial culture was analyzed using circular dichroism. Mass analysis of multi angle light scattering (MALS) coupled in line to AIEX column shows that the HIS-tagged version of the protein is a monomer in solution (Data not shown).

Example 11: Coomassie Staining

Gels were stained by an Instant Blue Coomassie staining solution (Expedeon) and exposed with ChemiDoc XRS+ camera (Bio-Rad).

Figure 30A:
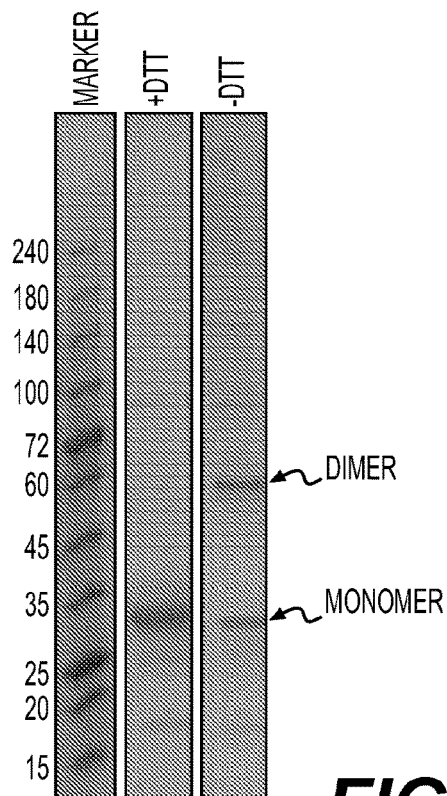
FIG. 30A is a representative SDS-PAGE of a BIX.XX-GGC protein after purification at reducing (–DTT) and non-reducing (+DTT) conditions, consistent with disclosed embodiments.
Figure 30B:
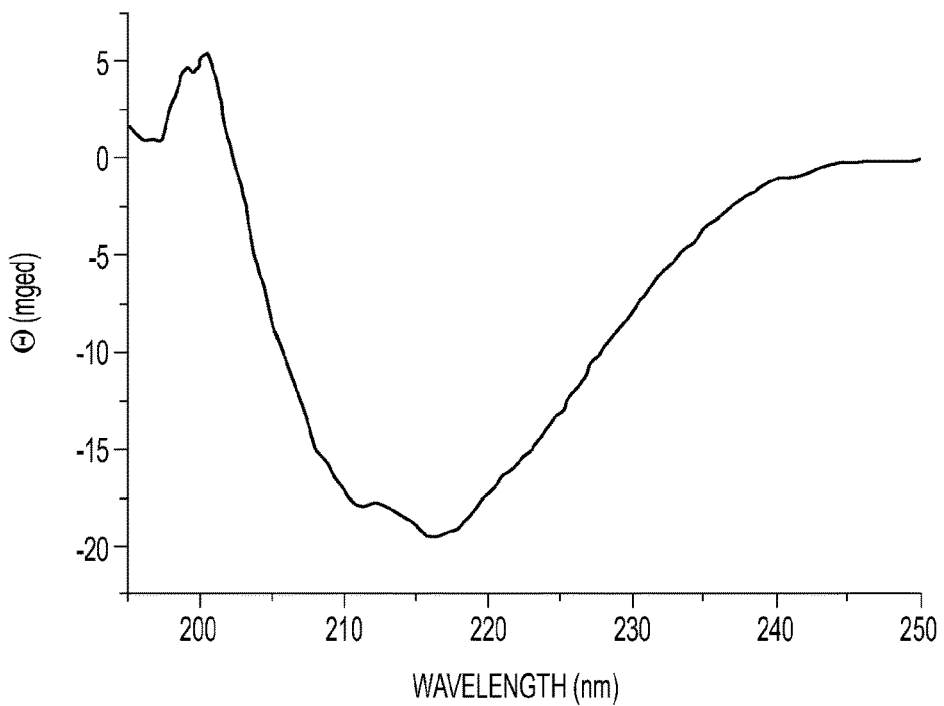
FIG. 30B is a representative CD spectra of a BIX.XX-GGC protein consistent with disclosed embodiments.

Coomassie staining of SDS-PAGE in reducing conditions shows that BI proteins are in the level of 85-95% purity (FIG. 30A +DTT). In the reducing conditions, all BI proteins run in SDS PAGE as monomers. However, in the non-reducing condition gels, fraction of monomeric pathogenic cell-removing proteins is around 50% and the rest are mostly dimers (FIG. 30B –DTT). Since those dimers occur through disulfide bond of the reduced cysteine residue (at the end of the protein chain), those dimers lose their ability to bind to the surface, as this cysteine residue is essential for surface binding.

Example 12: Circular Dichroism (CD) and Thermal Transition Measurements and Analysis CD spectra of the pathogenic cell-removing proteins were recorded using a J-810 spectropolarimeter (Jasco) in a 0.1 cm path length, quartz cuvette (Hellma, Mulheim, Germany). All measurements were performed in PBS. Data are presented as molar ellipticity, after baseline subtraction of PBS. Presented spectra were the average of 5 scans from 260 to 190 nm. Secondary structure was estimated using online DICHROWEB software. For stability testing, CD signals at 220 nm at several temperatures range between 4° C. to 90° C. were recorded for all pathogenic cell-removing proteins, for creating denaturation curves.

Circular dichroism measurements show that the proteins exhibit the secondary structure expected for these proteins according to literature (Chang et. al., J. Biol. Chem., 2001, 276(26):24170-24176, FIG. 30B). Proteins mostly contain a combination of beta sheets and alpha helixes. According to denaturation curve, the melting points (Tm) for all proteins were higher than the experimental temperatures (25° C. or 37° C.) indicating that all proteins are stable, and their structure remains so at these temperatures.

Overview of Examples 13-15

Examples 13-15 describe the surface modification of silicon wafers with BI X.XXX-GGC proteins, surface characterization, and atomic force microscopy of the modified silicon wafers.

Example 13: Surface Modification

Figure 31:
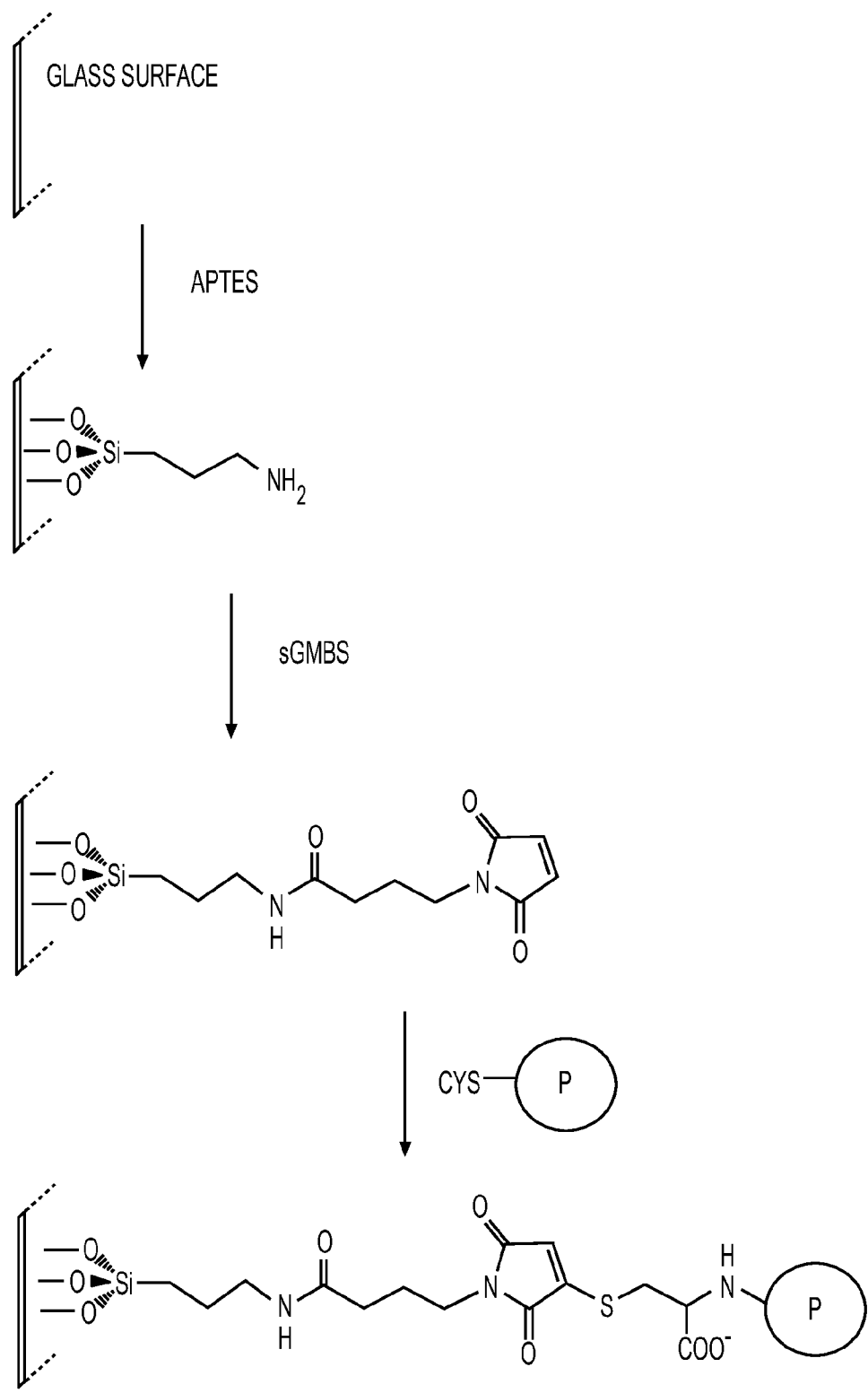
FIG. 31 is a schematic representation of a silicon wafer coating procedure, consistent with disclosed embodiments.
Figure 32A:
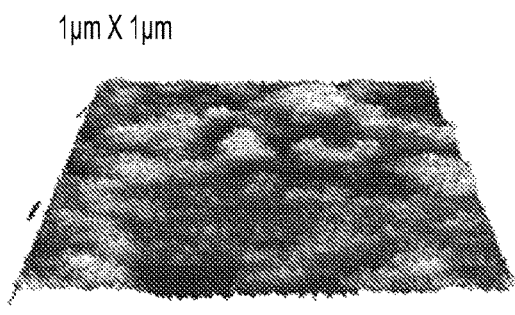
FIG. 32A schematically illustrates an Si wafer coated with the BIX.XX-GGC protein at 1 um×1 um field consistent with disclosed embodiments (AFM scanning).
Figure 32B:
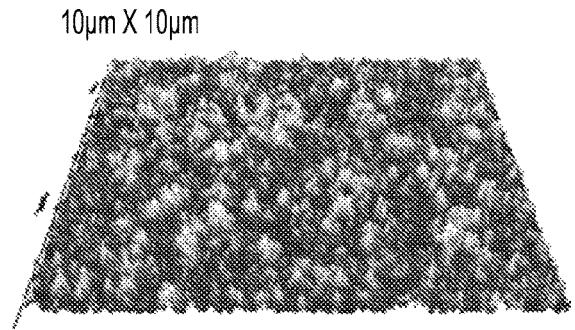
FIG. 32B schematically illustrates an Si wafer coated with the BIX.XX-GGC protein at 10 um×10 um field consistent with disclosed embodiments (AFM scanning).

Referring to FIG. 31, silicon substrate wafers were coated with BI X.XXX-GGC proteins in three step reaction. First, the wafers were coated with 3-amino-propyl-tri-ethoxy-silane (APTES), then with 4-maleimidobutyric acid sulfo-N-succinimidyl ester (sGMBS) cross-linker and lastly, the proteins were covalently linked to the aminosilane-functionalized gate nitride surface via the cysteine thiol group in the C-terminus of the pathogenic cell-removing proteins. Last, each protein-coated wafer was coated with a sucrose protective layer the protein layer.

Example 14: Surface Characterization

Ellipsometric measurements were carried out on a variable-angle spectroscopic ellipsometer (VB-200 VASE, Woollam Co.) around the Brewster angle for silicon (75°).

Ellipsometry measurements show APTES layer thickness of ~6-8 Å GMBS layer thickness of ~6 Å and final thickness of a protein coated Si slide (APTES+GMBS+Protein) of ~25 Å for mouse BI X.XXX-GGC protein, ~40 Å for rat BI X.XXX-GGC protein and ~50 Å for human BI X.XXX-GGC protein, corresponding to the diameter of the monomer (Data not shown).

Example 15: Atomic Force Microscopy (AFM)

Atomic force microscopy (AFM) measurements were carried out on an AFM cantilevers (Nano-Wizards 3, JPK Instruments, Berlin, Germany) with silicon tips (MSNL10, nominal tips radius ~2 nm, Bruker) for the final Si wafer product, coated with BI X.XXX-GGC proteins.

AFM analysis indicated that rat BI X.XXX-GGC protein coated Si slides and the human BI X.XXX-GGC protein coated Si-slides were coated with a very dense and homogenous layer, therefore indicating full protein binding capacity to the filter with no aggregation (see illustrations in FIGS. 32A-32B). The mouse BI X.XXX-GGC protein coated Si slide show lower density in the AFM measurements.

Overview of Examples 16 and 17

Examples 16 and 17 describe the in vitro testing of the preclinical prototype for extracorporeal blood filtration.

Example 16: PBMC and Whole Blood (WB) Filtration

Before assembly of each filtration unit, each filtration wafer was washed with TDW and dried with either N2(g) or O2(g), in order to remove the sucrose layer. After assembly of the filtration device to the peristaltic pump, the tubing was washed with saline supplemented with heparin. Tube with 5 ml of either whole blood from a patient or PBMCs purified from the same amount of blood (i.e. 5 ml blood) was connected to the filtration device and the peristaltic pump was used to establish a closed circle where the blood/PBMCs were circulated at a flow rate of 1 ml/min for 1 h. Once the filtration process ended the filter unit, PBMCs and the blood were taken for further analysis.

Example 17: Environmental Scanning Electron Microscopy (ESEM)

All scans were taken using FEI Environmental Scanning Electron Microscope Quanta 200 (FEI company, USA). In order to achieve better scan contrast, some of the samples were coated with gold/gold-palladium coating using Polaron SC7640 Sputter Coater (Quorum Technologies Ltd. UK) prior to the scan. The scans were performed on protein-coated Si wafers after incubation/filtration with PBMC or whole blood samples.

Overview of Examples 18-23: Preclinical Extracorporeal Blood Filtration with an MS Rat/Mice Model Examples 18-23 demonstrate the filtration capabilities of the biological filters having silicon wafers coated with pathogenic cell-removing proteins, as applied onto an rodents MS model (mice and rats).

Example 18: Preclinical Prototype Design and Assembly

Biological filters with flow chambers that enable extracorporeal blood filtration using silicon wafer coated with pathogenic cell-removing proteins were constructed and their filtration capabilities were evaluated. Initially, an animal model that can be connected to the filtration device was chosen. Mice and rats are the most common animal models used for studying MS. However, due to blood volume limitation of the filtration device, a rat model was chosen using Lewis rats with a minimal weight of 160 g on the day of filtration. The animal's minimal size allowed sufficient blood to be withdrawn for filtration without inducing a fatal effect to the animal.

The pre-clinical prototype contained two separate filtration units to filter two different sources (PBMCs, whole blood or two animals) simultaneously. The prototype had three crucial parts, base plate and two filtration heads. Each head subunit included: a socket to hold the filter, and inlet and outlet ports with luer lock connectors for fast and efficient assembly of medical tubing. The base and head were made from Polyetherimide (ULTEM 1000) that has both biocompatibility and sufficient strength properties. All the prototype subunits were shaped by means of a Computer Numerically Controlled (CNC) milling machine and assembled and sealed before each filtration procedure. The filtration unit was connected via Tygon® and Pharmed® tubing to Minipuls 3 (Gilson) peristaltic pump to allow efficient blood/fluid flow from and to the tested subject.

Example 19: Animal Models, Experimental Autoimmune Encephalomyelitis (EAE), and Clinical Assessment of EAE C57BL/6JOlaHsd mice were supplied by Envigo (Israel) originally from the Jackson Laboratory (Bar Harbor, Maine). Mice were held in an animal care facility according to approved rules for the use of animals in research. LEW/SsNHsd rats were supplied by ENVIGO from a nucleus colony obtained from the National Institutes of Health, Bethesda, Maryland, USA. Female rats from 7-10 weeks of age were used. All animals were cared for and handled according to the principles stated in the Declaration of Helsinki on the use of animals in research and National Ethics committee.

Experimental autoimmune encephalomyelitis (EAE) is the most common animal model and often serves as a "proof-of-principle" model for the efficacy of novel treatment strategies. EAE induction is especially useful to investigate neuroinflammatory pathways of MS disease as it shares many clinical and pathophysiological features involving the adaptive immune system. EAE model can be induced in many animals (e.g. mice, rats, mini-swine, guinea pigs, chickens, or primates), however the mice model was used for its ease of implementation and its fast and robust results. EAE utilizes the immune system reaction against brain-specific antigens which induces inflammation and destruction of antigen carrying structures (cells and myelin sheaths etc.) resulting the MS-like pathological features comparable to those observed in MS patients.

The subject animal was immunized with a subcutaneous injection of an emulsion consisting of the chosen antigen and complete Freund's adjuvants (CFA) (MOG35-55 peptide (Ray Biotech Inc., USA) in the mice model and g.pMBP68-82 (Genscript, USA), in rat model) accompanied by an intraperitoneal injection of Pertussis toxin on the day of immunization and two days later.

After the encephalitogenic challenge, the animals were observed daily. Clinical signs of EAE appeared 12-16 days after induction. The degree of clinical disease was scored as follows: 0—no paralysis; 0.5—decrease in tail tonicity; 1—paralysis of the tail; 1.5—Hind limb paresis, uncoordinated movement; 2—One hind limb paralyzed; 2.5—Both hind limbs paralyzed weakness in forelimbs; 3—Hind limbs paralyzed, one forelimb paralyzed; 3.5 Hind limbs paralyzed, both forelimbs paralyzed 4—quadriplegic animal in a moribund state; 5—death.

The safety and tolerability of the blood filtration procedure was also evaluated. Ten EAE rats were filtered on different days (d4, d6, d8, d4+d8) and compared to 5 untreated EAE rats. No mortality was observed as a result of the filtration up to 30 days post filtration procedure. The body weight loss was similar to the control group and no changes in the blood chemistry and hematology parameters were observed post filtration.

Based on a safety assessment study, a preliminary pilot clinical study with n=34 rats, divided into 5 groups as listed in Table 2, was performed:

TABLE 2

Groups of rats in preliminary pilot clinical study

| | Treatment | N |
|---|---|---|
| A | EAE untreated | 8 |
| B | EAE, sham filtration (d4, 5 or 6) | 8 |
| C | EAE, full filtration d4 | 6 |
| D | EAE, full filtration d5 | 6 |
| E | EAE, full filtration d6 | 6 |

No mortality was documented in all the groups. The weight loss was similar for all groups, and no differences were observed in the blood tests (data not shown).

Figure 33A:
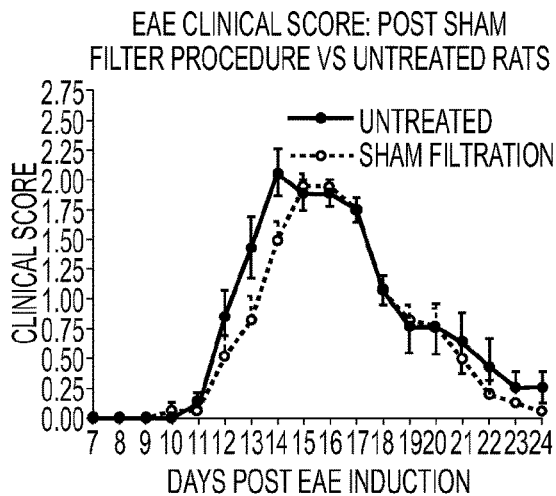
FIGS. 33A-33D are graphs showing clinical scores post-filtration in rat EAE model (scored on a 0-5 scale) as measured immediately post procedure (FIG. 33A), at day 4 (FIG. 33B), day 5 (FIG. 33C), and day 6 (FIG. 33D) post procedure, consistent with disclosed embodiments.
Figure 33B:
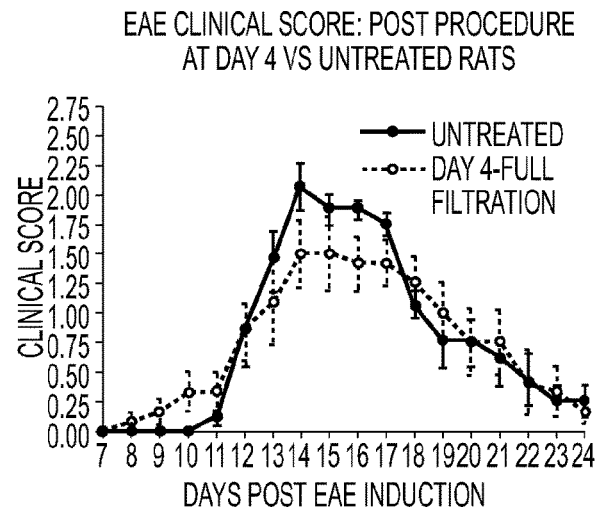
Figure 33C:
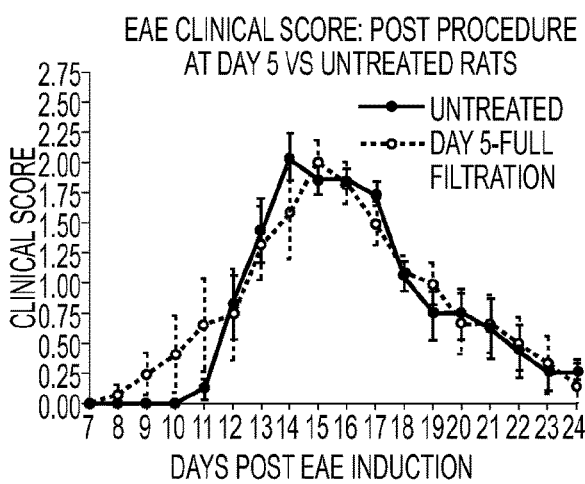
Figure 33D:
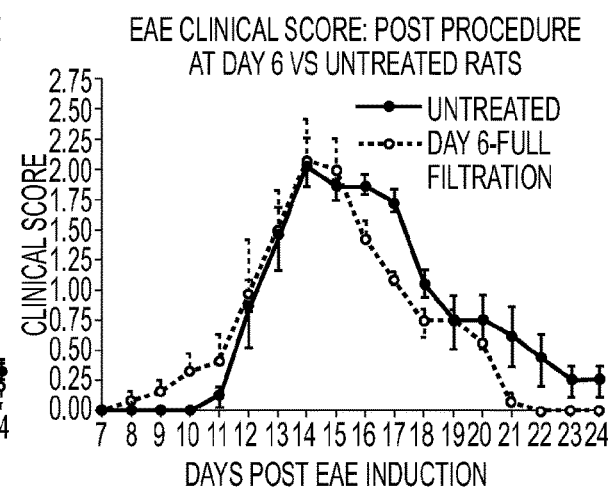
Figure 34A:
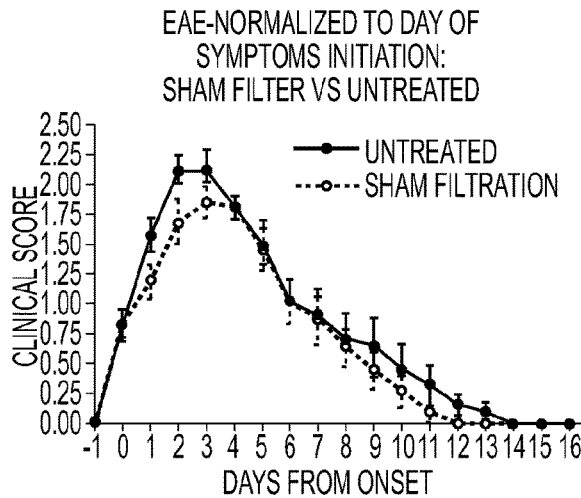
FIGS. 34A-34D are graphs showing clinical scores adjusted to day of onset post-filtration in rat EAE model (scored on a 0-5 scale) as measured immediately post procedure (FIG. 34A), at day 4 (FIG. 34B), day 5 (FIG. 34C), and day 6 (FIG. 34D) post procedure, consistent with disclosed embodiments.
Figure 34B:
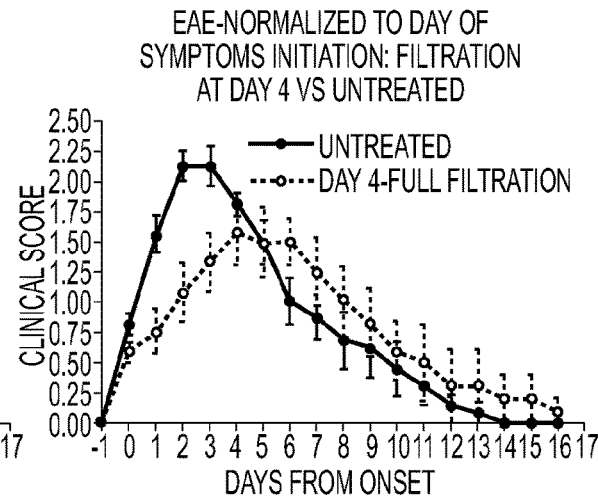
Figure 34C:
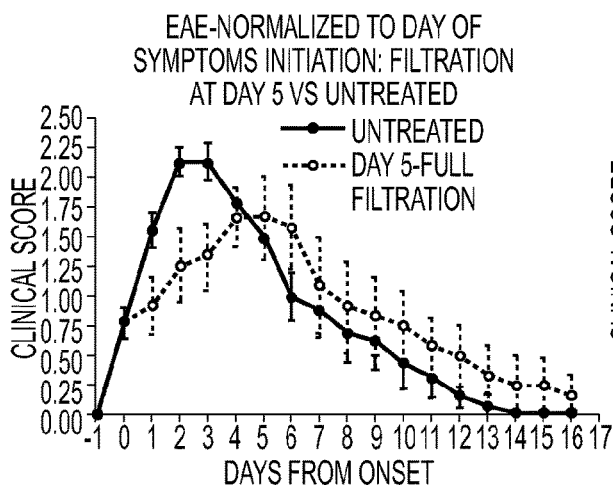
Figure 34D:
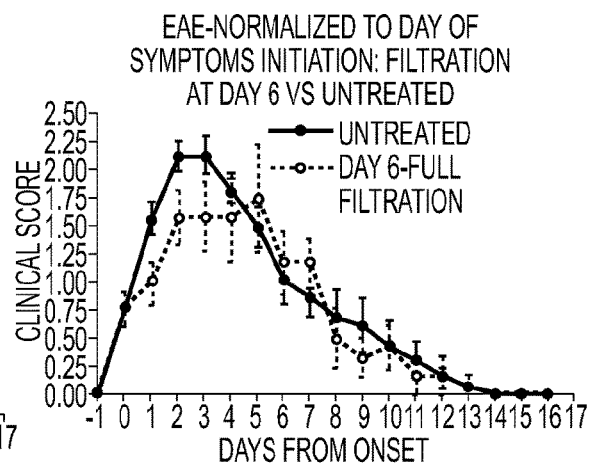

Disease activity was assessed starting from day 8 until the spontaneous remission. No improvement in disease activity was seen in rats undergoing sham filtration when compared to the untreated rats (FIG. 33A). Day 4 filtration showed a milder disease induction with a lower peak on day 14 (1.5±0.28 vs. 2.06±0.2) respectively (FIG. 33B). Single 1 h filtration on day 6 showed a same onset and time to peak, but a significant faster recovery starting at day 16, 48 hours prior to control group, with $p<0.01$ for days 16 and 17 (FIG. 33D). Animals that were filtered on day 5 showed similar results to the untreated group (FIG. 33C), with a minor non-significant shift in disease progression to the peak.

Interestingly, there is one more way to analyze the clinical scores results. Since the disease onset varies from one rat to another (day 8-14) it is common to determine day of onset separately for each animal and to set this day as day 0 (as described previously by Pollak et. al., Neuroimmunology 2003; Lange et. al. Ann Rheum Dis 2005; Ringheim G. E et. al. Frontiers in Neurology, 4. 2013). It can be seen that all 3 groups showed decrease in peak score versus the untreated animals (Table 3 and FIGS. 34A-34D) suggesting that the procedure had more effect than was observed in FIGS. 33A-33D.

TABLE 3

Comparison analysis by day of onset.

| | Untreated | Day 4 | Day 5 | Day 6 | Sham filter |
|---|---|---|---|---|---|
| Peak clinical score | 2.125 | 1.58 | 1.66 | 1.75 | 1.88 |
| Day of peak from onset | 2 | 4 | 4 | 5 | 3 |
| % change | NA | −25.5% | −21.6% | −17.6% | −11.8% |

Example 19: Blood Chemistry and Hematologic Analysis

Blood was obtained from rats by retro-orbital sinus puncture and collected twice at day 4 post-EAE induction and 48 h post-filtration procedure. Blood and serum were sent to analysis by American Medical Laboratories (Israel), for full blood hematological and chemistry panel.

Example 20: Extracorporeal Blood Filtration

LEW/SsNHsd rats were anesthetized with isoflurane\O2 mixture using isoflurane vaporizer during the whole filtration procedure. Two tail cannulations were made per animal using 27G cannula, arterial cannulation for blood withdrawal and venous cannulation for blood retention. Each rat was connected through the arterial cannulation to the filtration device inlet port, enabling blood flow into the filtration unit and through the outlet port to a peristaltic pump that returned the blood to the test subject via the venous cannulation at a flow rate of 0.8-1 ml/min.

In order to prevent animals from developing hypovolemic shock or blood clotting during the procedure, the filtration unit and tubing set were pre-washed with heparinised physiological water (0.9% Sodium Chloride injection solution supplemented with 25 units/ml Heparin).

Example 21: EAE Induction in Mice and PBMCs Enrichment

In order to establish a more robust and less complicated way of obtaining cells for R&D needs, the mice model for MS was used as a more feasible resource. EAE was induced to C57/6JOLaHsd female mice (as described above), and spleens were removed for isolation and activation of splenocytes. Induction of disease was peptide specific, using mouse MOG35-55 as an encephalitogenic peptide, and the same peptide was used for in vitro enrichment and expansion of the specific clone of T-helper cells in the presence of IL-2, IL-12 and IL-23 for 72 h.

Example 22: FACS

Flow cytometry acquisitions were performed on a BD FACS Canto II using standard protocols for staining of about 1-2×106 cells per sample. At least 250,000 events were recorded for each sample and the data analysis was performed using FCS express version 6.0 (De Novo software). All antibodies and tetramers used for the FACS labeling are listed in Table 4, below.

Example 23: Fluorescent Microscopy

In order to visualize attachment of cells to the 2D filter, antibodies (Table 4) were applied on the biological filter post-filtration, according to the manufacturer's recommendations for Immunohistochemistry staining. Surfaces were visualized using LEICA confocal imaging system SP5.

TABLE 4

List of antibodies and tetramers used in the analysis.

| | protein | Fluorophore | Manufacturer | Clone |
|---|---|---|---|---|
| Human | Anti CD4 | APC | BioLegend | OKT4 |
| human | Anti CD19 | FITC | BioLegend | SJ25C1 |
| Human | DRA1*0101-DRB1*15:01-MBP85-99 | PE | Proimmune | |
| Mouse | Anti CD4 | APC | BioLegend | GK1.5 |
| | Anti CD19 | FITC | BioLegend | 6D5 |
| | I-A$^b$-MOG35-55 | PE | MBL | TS-M704-1 |
| Rat | Anti CD3 | FITC | BioLegend | 1F4 |
| | Anti CD4 | APC | BioLegend | W3/25 |

Overview of Examples 24 and 25

Examples 24 and 25 describe the observational clinical study in human patients.

The immune system is traditionally divided into two main arms, innate and adaptive immunity. While the first is non-specific and serves as the first line of defense against pathogens, the last is considered to be a specific, iterating arm. Adaptive immunity is composed of both cellular and humoral components. While B-cells recognize their specific targets in their soluble form through antibodies, T-cells recognize their targets only when they are presented on HLA molecules expressed by nucleated cells (type I) or by antigen presenting cells (type II).

In autoimmune diseases, the immune system identifies self-antigens as foreign, thus attacking the body in a wide spectrum of diseases, ranging from organ specific (e.g. thyroid or pancreas) to systemic diseases (e.g. systemic lupus erythematosus). Current treatments for autoimmune diseases are focused on a global and general immunosuppression that entails major side effects and causing the individual to be more prone to infectious diseases.

Thus, in the context of multiple sclerosis (MS), some embodiments described herein are aimed at removing the specific T-cells that recognize myelin-associated proteins and that are involved in disease initiation and progression in MS. Biological filter embodiments described herein are able to recognize, capture and remove those target cells from the peripheral blood of MS patients.

The first mission was expression and purification of the trap proteins. Partial HLA type II recombinant proteins, homologous to human DR, were designed and expressed as described in the following examples. Based on physiological interactions between T-cell and antigen presenting cells (APCs), those peptide-loaded proteins can recognize and bind to the corresponding T-cell receptor of the relevant clone.

The next milestone was anchoring of the proteins to a biocompatible surface. As described, a coating of a uniform-monolayer with the target proteins was successfully constructed. All optical and biochemical validations were positive, including ellipsometry for measurements of layer thickness.

In order to show a real-time live filtration of cell suspension, a prototype device was designed, with a 2D filter embedded, connected to a peristaltic pump, circulating the sample. This prototype device was used in both the pre-clinical experiments and the ex-vivo, human blood validations of the blood filtration platform technology described herein. In the pre-clinical experiments as described, the procedure showed to be safe and tolerable in both naïve and EAE induced rats. The proof-of-concept experiment in rats also identified the following observations:

1. In order to perform the filtration, rats must be under anesthesia for at least 1.5 hours. It is important to emphasize that longer periods of anesthesia are a significant risk factor for survival and therefore, this time should not be further prolonged in order to achieve more efficient removal of relevant T-cells.

2. The device prototype is a preliminary prototype, with flow limitations and a possible exposure to air, all of which may influence the quality of filtration.

Figure 35A:
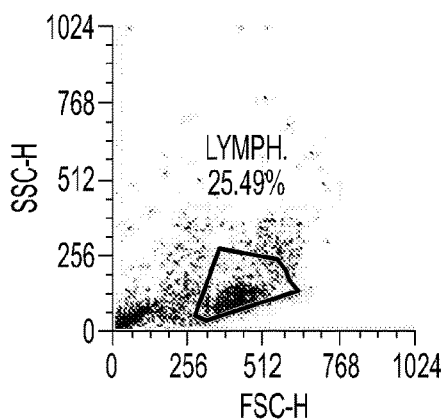
FIGS. 35A-35F are a representative flow cytometry analyses of human derived PBMCs, consistent with disclosed embodiments.
Figure 35B:
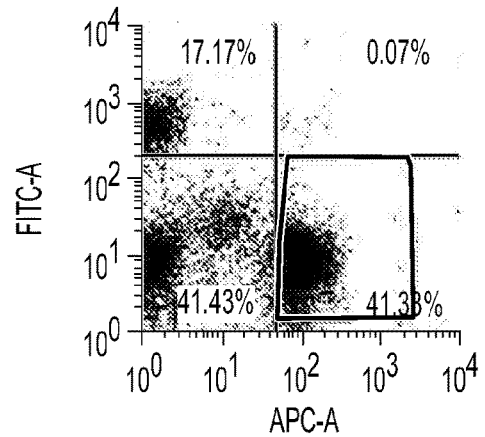
Figure 35C:
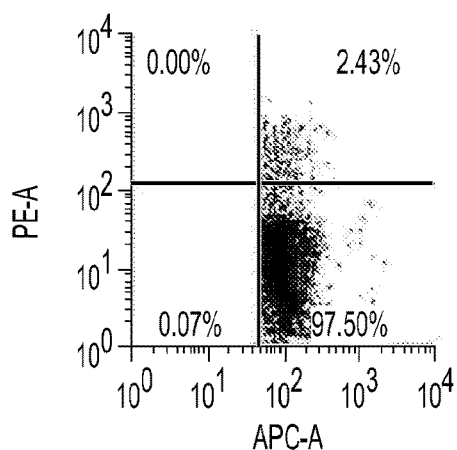
Figure 35D:
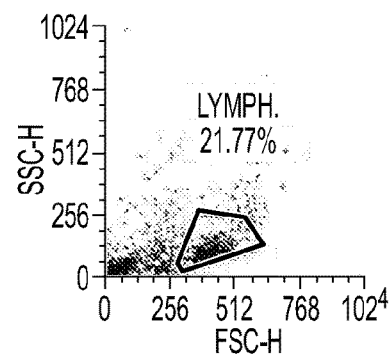
Figure 35E:
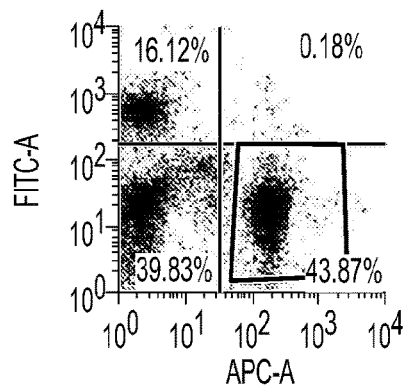
Figure 35F:
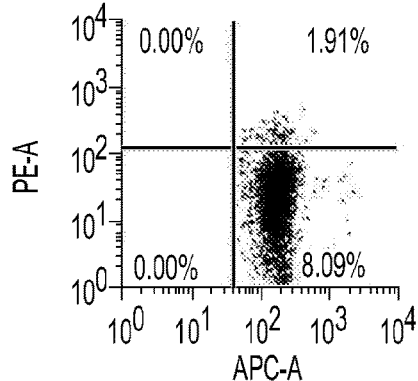
Figure 38A:
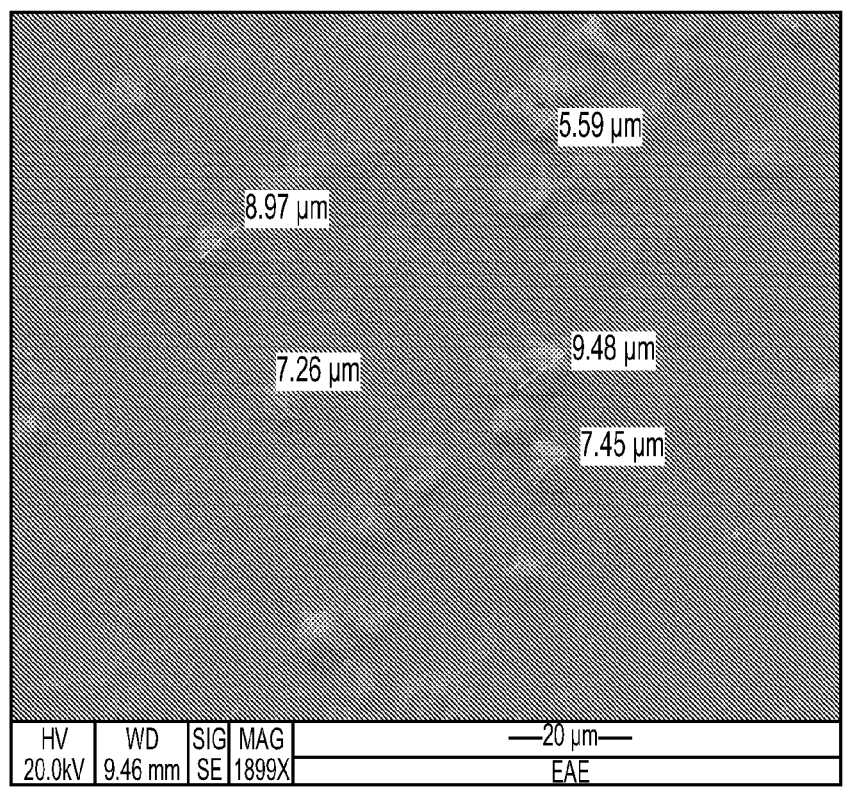
FIGS. 38A-38C are magnifications of filter surfaces after filtration of mice cells, consistent with disclosed embodiments.
Figure 38B:
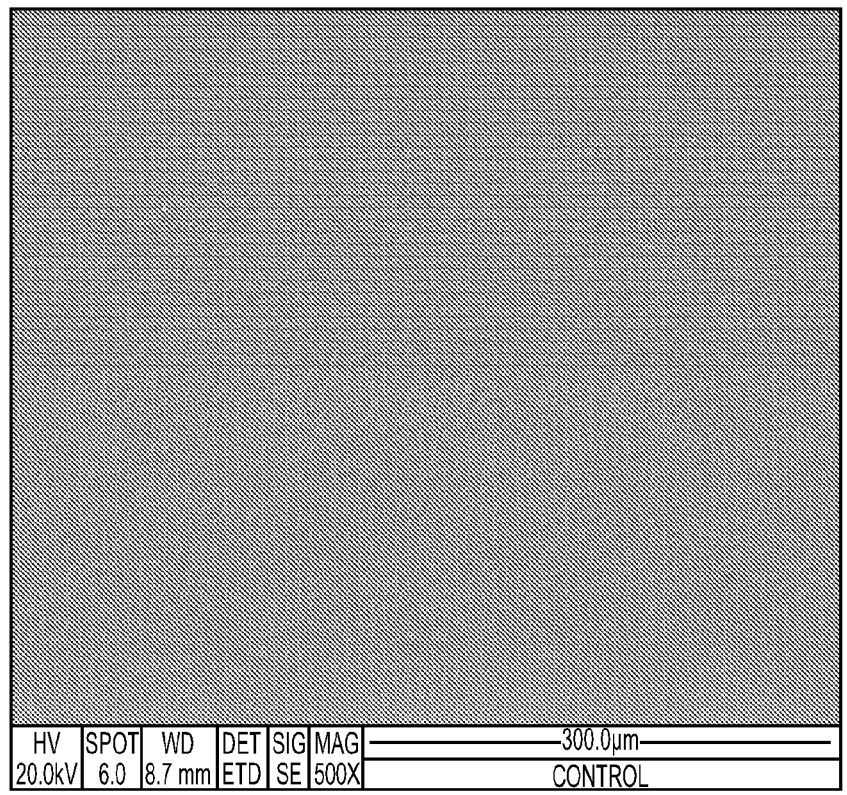
Figure 38C:
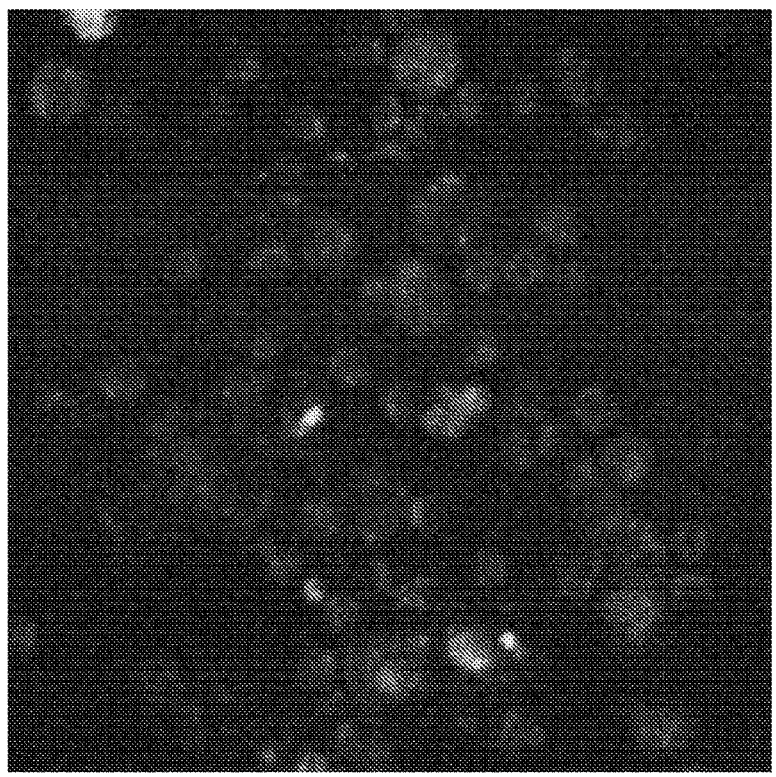
Figure 39:
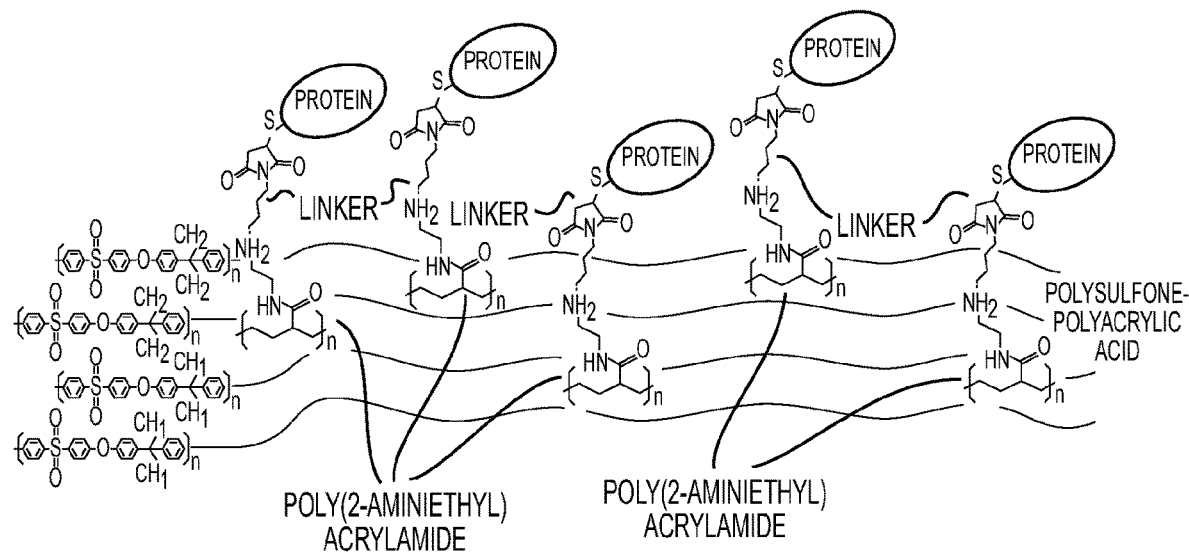
FIG. 39 is a schematic illustration of protein binding to a membrane composition, consistent with disclosed embodiments.
Figure 40A:
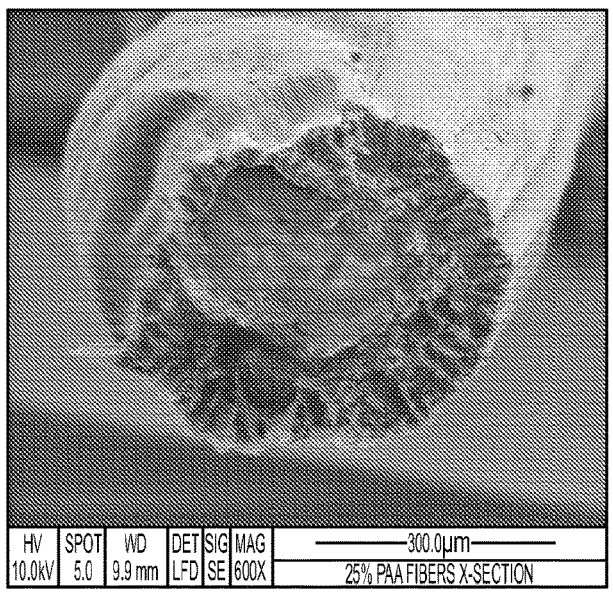
FIGS. 40A-40C illustrate scanning electron microscopy (SEM) results of polysulfone-polyacrylic acid (PAA) fibrils, consistent with disclosed embodiments
Figure 40B:
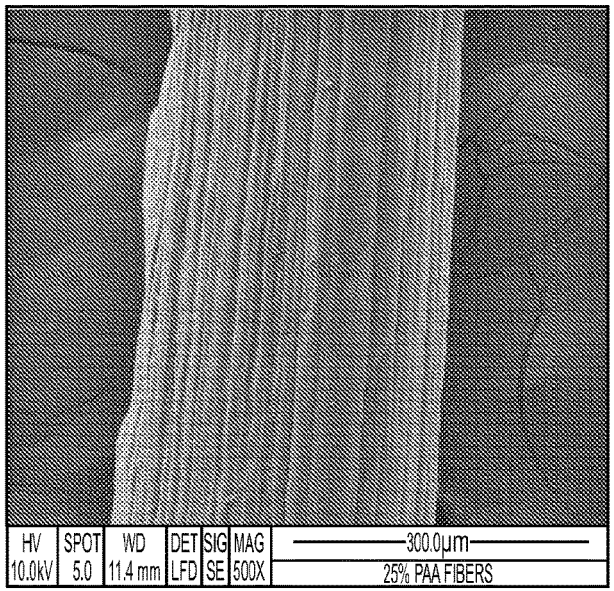
Figure 40C:
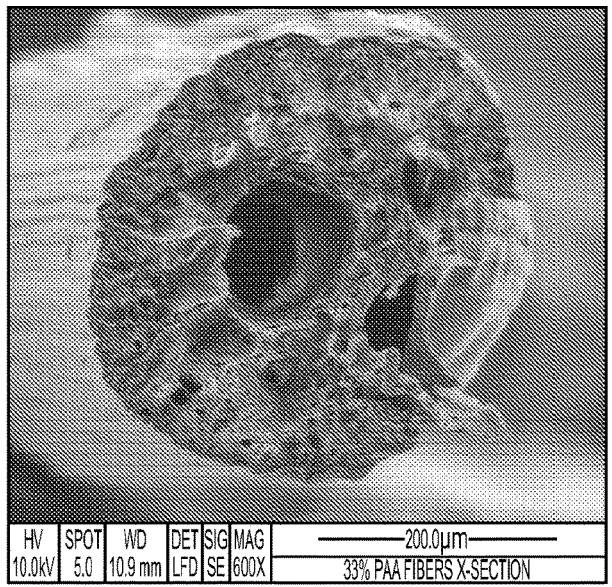
Figure 43:
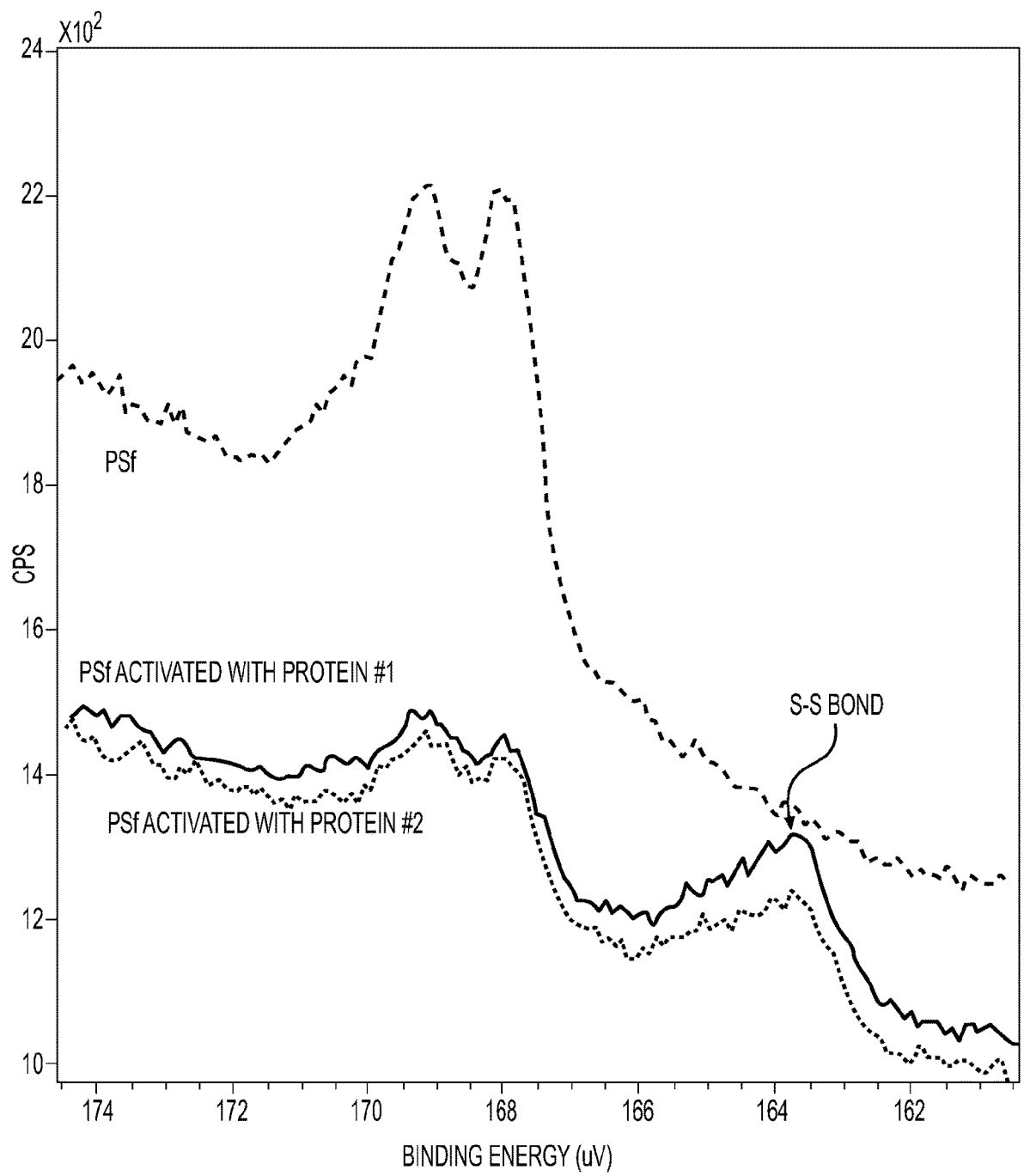
FIG. 43 is a graph showing X-ray photoelectron spectroscopy (XPS) results of protein activated PSf sheets, consistent with disclosed embodiments.

3. From the accumulated data it was observed that whole blood filtration is less effective than the PBMC's filtration in which only PBMC's come into contact with the filter. Experiments conducted on human PBMC's from MS patients were much more effective even within 1 hour of filtration (FIGS. 35A-35F, FIG. 36). In FIGS. 11A-11F, first lymphocytes were gated according to forward and side scatter. Next, FITC labelled CD19 cells were excluded (representing B-cells) versus APC labelled CD4+ cells (representing helper T-cells) and finally PE-positive (representing clone specific T-helper cells out of the total helper T-cells subpopulation) were calculated. Shown here are the analyses of PBMCs pre-filtration (FIGS. 35A-35C) vs. post-filtration PBMCs of the same patient (FIGS. 35D-35F)

Therefore, it may be assumed that the whole blood filtration in rats was less efficient for filtration.

4. Even though filtration on day 4 post-disease induction results showed superiority relative to days 5 or 6, in days 5 and 6, most T-cells had managed to migrate from the circulation to the CNS and induced the disease. While in the day 4 filtration the filter managed to remove a significant fraction of EAE related T-cells from the circulation causing moderate effect.

Examples 24 and 25 validated the approach ex vivo, showing the ability of the prototype device to remove more than 40% of the specific T-cell clone by filtration of PBMCs derived from six different MS patients within a one hour of filtration. This was validated by cytometric analyses as described.

Both the ex vivo and in vivo experiments suggest that a more appropriate approach in humans may involve a leukapheresis procedure that will start with a production of PBMC fraction, followed by specific MS-related T-cell depletion using the biological filter and reposition of the filtered PBMCs back to the patient, thus, preserving the patient's immune system integrity.

Example 24: HLA Genotyping of MS Patients

Up to this point a total of 26 subjects have been recruited to the observational clinical trial described in the methods. Of them: Eight newly diagnosed MS patients (group A), 16 diagnosed MS patients for more than three years (Group B) and two control subjects with no known history of autoimmunity (Group C). Main purposes of this cohort were to obtain data regarding HLA type I & II haplotypes and their prevalence among the study groups and establishing a small reservoir biobank of aliquoted frozen samples of PBMC from those subjects. Cells were thawed when needed for evaluation of a specific binding to the biological filter. Main interim summary of allelic frequencies of different HLA type I (A, B and C) and type II (DR and DQ) are presented in Tables 5 and 6, below. For example, it is known that DRb15:01 is found among 30-50% of MS patients in the US (Hollenbach et al. J Autoimmun., 2015, 64:13-25) and between 17-24% among Israeli Jews (Kwon et al., Arch Neurol., 1999, 56(5):555-560) with a higher prevalence when compared to the general (Non-MS patients) population.

So far, of this cohort, 25% of MS patients carry the "notorious" allele (allelic frequency of 12.5%), and their PBMCs collected were used to evaluate filter performance. The foregoing is just an example. other target proteins may be identifiable from the collected data combined with the known data available in the literature for target genetic groups among MS patients.

TABLE 5

HLA type I allelic frequencies among MS patients (N = 24)
HLA type I

| A | | | B | | | C | | |
|---|---|---|---|---|---|---|---|---|
| Allele | Num | % | Allele | Num | % | Allele | Num | % |
| 01:01 | 7 | 14.58 | 13:02 | 5 | 11.63 | 07:01 | 9 | 18.75 |
| 02:05 | 6 | 12.50 | 18:01 | 5 | 11.63 | 12:03 | 8 | 16.67 |
| 02:01 | 6 | 12.50 | 08:01 | 4 | 9.30 | 06:02 | 7 | 14.58 |

TABLE 6

HLA type II allelic frequencies among MS patients (N = 24)
HLA type II

| DRB | | | DQB | | |
|---|---|---|---|---|---|
| Allele | Num | % | Allele | Num | % |
| 07:01 | 8 | 16.67 | 03:01 | 13 | 27.08 |
| 11:04 | 6 | 12.50 | 02:02 | 8 | 16.67 |
| 15:01 | 6 | 12.50 | 06:02 | 5 | 10.42 |

Example 25: Validation of Filtration of MS Patients' Blood

Thus far, 26 subjects were recruited to the observational clinical study. Of them, six patients expressed the target allele DRb15:01. Blood was collected from those patients in order to perform an ex vivo validation of the blood filtration technology described herein. Upon arrival of the heparinized blood from the hospital, a portion of the blood was taken for PBMCs isolation and the rest was used as is. Simultaneously both samples, the whole blood (WB) and the PBMCs purified fractions were circulated for 1 hour through the prototype chamber in a constant flow rate of 1 ml/min using a peristaltic pump. Samples were taken pre- and post-filtration for analysis using flow cytometry.

Commercially available tetramers (see Table 4), directed against and able to bind specifically only to T-cells expressing the T-Cell Receptor against human MBP85-99, presented on HLA type II, DRb15:01 were used. This enabled the detection the specific target T-cells intended to be removed. A decrease in the percentage of those specific cells of the entire CD4+ T-cells, indicate recognition, capturing and removal of those cells by the prototype filter during the procedure. FACS analyses showed an average removal of 42% of target cells, ranging from 21% to 65% following one hour of filtration of the isolated PBMCs fraction (T-test for paired samples gave a p<0.01, FIGS. 35A-35F). In addition, at the same time no significant changes were observed neither in total B-cell subpopulation nor total helper T-cell subpopulation due to filtration of PBMCs.

In vitro filtration of whole blood gave non-specific results, due to technical limitations of the filtration procedure, the exposure of the blood to the air, a non-specific binding of the blood components to the device (excluding the filter surface itself) and limitation of performing FACS analysis to the WB samples post filtration.

Two patients (204, 211, see FIG. 36) showed the highest pre-filtration levels of the clone specific CD4+ T-cells. Interestingly, those patients were under Tysabri, which blocks the migration of lymphocytes from the peripheral blood to the CNS by binding to and blocking integrin α4.

These circumstances suggest that concomitant Tysabri therapy of Tysabri may induce potency and effectiveness of filtration.

After filtration with WB or PBMCs, the human BIX.XX-GGC protein-coated Si slides were washed with water, coated with gold and analyzed with ESEM. The results show binding of cells to the filter, with diameters of 6-9 nm, and some larger cells with diameter of 12 nm (FIGS. 37A-37B). FIG. 37A is an SEM photograph of human BIX.XX-GGC protein-coated Si slides after filtration with patient whole blood. FIG. 37A is an SEM photograph of human BIX.XX-GGC protein-coated Si slides after filtration with patient PBMCs.

In another experiment, after filtration, the filters were washed with RPMI and dyed with antibodies against CD4 (T-cell marker), CD19 (B-cell marker) and with tetramers for dying specific T-cells that recognize the HLA complex. The results showed binding of T-cells to the filter, and the specific T-cells were identified as well (data not shown). 2-4×$10^6$ cells extracted from EAE mice splenocytes were diluted in RPMI medium (Biological industries, Israel) and filtered on a mouse BIX.XX-GGC protein-coated Si slide for 1.5 hours. The slides were washed with PBS and water, dried and coated with gold for ESEM measurements. ESEM showed binding of cells to the filter, with a diameter of 6-8 microns. Incubation of cells extracted from splenocytes of healthy mice showed almost no binding to the filter compared with the cells from the EAE induced mice, indicating the specificity of the filter (see images in FIGS. 37A-37B).

For confocal microscopy measurements, slides were washed with PBS after incubation with the cells, and then stained with commercial dyed tetramers for staining specific T-cells that recognized the MHC II complex (FIGS. 38A-38C). FIG. 38A is an ESEM photograph of the BIX.XX-GGC protein-coated Si slide after filtration of cells extracted from splenocytes of an EAE mouse. FIG. 38B is an ESEM photograph of the BIX.XX-GGC protein-coated Si slide after filtration of cells extracted from splenocytes of a healthy mouse. FIG. 38C is a confocal microscopy picture of tetrameric staining of BIX.XX-GGC protein-coated Si slides after filtration of cells extracted from splenocytes of an EAE mouse.

Example 26: Preparation of Polysulfone/Polyelectrolyte-Based Polymeric Matrix for Capturing Biomolecules and Biomaterials In this example, a matrix comprising a combination of high performance thermoplastic polymer (e.g. polysulfone and derivatives) and polyelectrolyte (e.g. polyacrylic acid and poly(2-aminoethyl)acrylamide) was produced from a soluble, miscible blend of polyacrylic acid (PAA) (5-40%) and polysulfone (PSf) (60-95%). The matrix can be thin films, filaments, hollow fibers or any other polymeric structure that is accessible to aqueous solutions. After solidification and creating the solid surface, the carboxyl group of PAA can directly interact or can be transformed to other functional group (e.g. amine or maleimide group) that interact with other chemical or biological molecules or macromolecules to produce/design a final surface for capturing specific elements (e.g. proteins, cells or other components).

Polysulfone-poly(2-aminoethyl) acrylamide membrane (film or fibers) preparation: The dry/wet static technique was the preparation technique employed to produce the hollow fiber membranes, a schematic diagram of which is provided in FIG. 39. In this figure, membrane films/fibers compose of a polymeric combination of polysulfone and polyacrylic acid that is modified during production to poly(2-aminoethyl)acrylamide and is further activated with maleimide linkers that covalently bind the protein of interest in a specific manner. First, a casting solution was prepared as follows: 8% of additive (PAA) was dissolved in dry DMF (Dimethyl Formamide) at 100° C. and the solution was stirred at 500 rpm using a magnetic stirrer for 2 hours, until a homogenous solution was obtained. In parallel, 16% of solid PS was dissolved in dry, pure DMF solvent. After obtaining a homogeneous mixture, PS was added to PAA solution drop by drop. The mixed materials were stirred at 100° C. and 700 rpm until miscible mixture was formed. Then, the whole solution was introduced in a sonication bath maintained at 40° C. until the mixture became a miscible blend. The percentage of the mixture composition used to prepare blend solution was variable, depending on strength requirement of final product. 5-40% mass percentage of polyacrylic acid (PAA) was mixed with polysulfone (PSf). The PSf-PAA blend was pushed through a syringe on water wet glass sheet or into a water bath, while parallel draw with tweezers was used to create the fibers. The glass sheet can be wet with MilliQ water (18.3 MΩ·cm) at 18° C., or with physiological solution. Using this procedure, fibers of 0.2-0.3 μm width were produced as hollow fibers. The thickness of the middle-pore was determined by the PAA percentage in the PSf-PAA blend. For 25% PAA the diameter of the pore was ~200 micron and for 33% PAA the diameter was ~100 micron (FIGS. 41A-41C). Fibers composed of 25% PAA (FIGS. 41A-41B) or 33% PAA (FIG. 41C) create hollow fiber structure in a width of 200-300 micron.

Films of PSf-PAA can also be performed from the described PSf-PAA blend by immersing blend solution, that is dropped on a glass sheet, in a coagulation bath containing a sufficient volume (that completely cover the slide) of MilliQ water (18.3 MΩ·cm) at temperature of 18° C. Very thin films can also be performed from this blend (final concentration of both component in DMF solution is 0.5-3% w/v) using spin coater carrying on a glass or silicon basis sheet with aminopropyl triethoxysilane as an adhesion layer. Membranes/fibers being washed with water and stored until their use. PSf-PAA membranes/fibers are then reacted with ethylenediamine to create functional amine group instead of the carboxyl group of the PAA and generating PSf-poly(2-aminoethyl) acrylamide fibers/films. Different protocols for creating fibers and hollow fibers are available in literature (e.g., Choi et al, European Polymer Journal, 2010, 46(8): 1713-1725). The procedures employed herein were adopted for their ease of use and the fact that they do not require a special facility or special equipment.

Maleimide activation with linker elongation: Sulfo-N-succinimidyl 4-maleimidobutyrate (sGMBS) was utilized as the maleimide linker. The sGMBS is a carbohydrate with active ester at the terminal that interacts with the anime nucleophilic group on the poslysulfone-poly(2-aminoethyl) acrylamide membrane. sGMBS sodium salt is dissolved in PBS (pH=7.2) to a concentration of 1 mM immediately before use and incubated for 18-22 h at 25° C. with polysulfone-poly(2-aminoethyl) acrylamide membrane.

Protein-maleimide interaction: The protein of interest (e.g. HLA-derived protein) is produced as a recombinant protein in a certain organism (e.g. bacteria, yeast, insect or mammalian cells) with a reduced cysteine residue at the protein termini (e.g. C-terminus). 10 μM of pure protein diluted in PBS (pH=7.2) was incubated with polysulfone-poly(2-aminoethyl) acrylamide membrane activated with maleimide functional group, for 2 h at 25° C. This procedure resulted in a protein's mono-layer on the surface (FIGS. 41A-41B, 42A-42B, 43), with a thickness of ~40-50 Angstrom (as measured by AFM and ellipsometer on silicon slides), with a stable thioether bond between the protein and the matrix. FIG. 18A shows the AFM topography of the dense protein's monolayer. FIG. 18B is an AFM profile graph recorded from a protein coated silicon slide show a layer thickness of 4.5 nm. The graph in FIG. 19 displays three samples: PSf non-activated, PSf activated sheets with protein 1 and PSf activated sheets with protein 2 (2 variants of human GGC protein). Both protein-activated PSf sheets display a peak at ~163.5 eV correspond to disulfide bond (S—S) that appears only in the structured functional protein.

Protein-coated membrane activity: These covalently modified protein membranes can be utilized for several applications in the biology/biochemistry/medicine fields. It can be used for analytical tests for quantifying and characterizing the protein partner/target (e.g. other proteins, cells or other bio or non-bio molecules). Based on the protein interactions with its partner, specific medicinal application can be applied, for example apheresis or dialysis special filters that rely on interactions of specific cells with the protein coated membrane, allowing removal of those cells from patient blood stream or fraction of the blood (e.g. PBMCs).

The foregoing description, including the examples, has been presented for purposes of illustration. It is not exhaustive and is not limited to precise forms or embodiments disclosed. Modifications and adaptations of the embodiments will be apparent from consideration of the specification and practice of the disclosed embodiments. For example, while certain components have been described as being coupled to one another, such components may be integrated with one another or distributed in any suitable fashion.

Moreover, while illustrative embodiments are described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and, accordingly, all suitable modifications and equivalents may be resorted to, falling within the scope of the disclosure.

Disclosed embodiments may include any one of the following bullet-pointed features alone or in combination with one or more other bullet-pointed features, whether implemented in connection with a filter, a device, a system, computer readable media or a method:

an inert surface medium human leukocyte antigen (HLA) proteins disposed on the inert surface medium antigen peptides bound to the HLA proteins on the inert surface medium antigen peptides and the HLA proteins selected to enable antigen-specific T-cell receptors to bind to a complex of the antigen peptides and the HLA-proteins when T-cells are brought into contact with the complex, thereby securing specific T-cells to the inert surface medium via the complex an inert surface medium including sheet material, mesh structures, fibers, gels, a liquid, or beads an inert surface medium including polysulfone or polysulfone derivatives, glass matrices, silicon matrices, polydimethylsiloxane (PDMS), polycarbonate, polyetherimide (Ultem), or Tritan an inert surface medium including polysulfone an inert surface medium including a polyelectrolyte.

HLA proteins disposed on an inert surface medium through covalent bonding, non-covalent interactions or adsorption HLA proteins disposed on an inert surface through a maleimide analog an inert surface medium including polyethylene glycol (PEG) or PEG derivatives, polystyrene, avidin and/or streptavidin HLA proteins disposed on an inert surface medium in a manner such that anchoring locations for HLA proteins are spaced from each other by at least a width of an HLA binding groove HLA proteins including at least one of a monomer or a multimer truncated HLA proteins HLA proteins engineered to include a cysteine as the C-terminal residue a C-terminal cysteine linked to an HLA protein through a peptide linker HLA proteins HLA-typed to match a patient antigen peptides synthetically produced and loaded onto HLA proteins to form HLA-peptide complexes capable of selectively binding antigen-specific T-cell receptors HLA proteins recombinantly produced an antigen peptide derived from a protein associated with multiple sclerosis an antigen peptide derived from myelin oligodendrocyte glycoprotein (MOG), myelin basic protein (MBP), myelin proteolipid protein (PLP), opalin protein, oligodendrocyte-specific protein (OSP), myelin-associated glycoprotein (MAG), or a combination thereof an antigen peptide is $MBP_{87\text{-}99}$, $MBP_{85\text{-}99}$, $MBP_{83\text{-}96}$, $MBP_{217\text{-}231}$, $MBP_{88\text{-}102}$, $MBP_{282\text{-}296}$, $PLP_{91\text{-}110}$, $PLP_{131\text{-}151}$, $PLP_{283\text{-}252}$, $PLP_{263\text{-}277}$, $PLP_{58\text{-}72}$, $PLP_{13\text{-}27}$, $OPALIN_{46\text{-}60}$, $OPALIN_{27\text{-}41}$, $OPALIN_{127\text{-}141}$, $MOG_{210\text{-}224}$, $MOG_{29\text{-}43}$, $MOG_{176\text{-}190}$, $MOG_{225\text{-}239}$, $OSP_{74\text{-}88}$, $OSP_{114\text{-}128}$, $MAG_{8\text{-}22}$, $MAG_{467\text{-}481}$, $MAG_{529\text{-}543}$, or a combination thereof a filter including a plurality of layers configured to permit fluid flow therebetween a filter medium for hosting material that selectively binds antigen-specific T-cell receptors a filter hosting material including human leukocyte antigen (HLA)-myelin-peptide complexes selected to bind with myelin-specific T-cell receptors, to thereby enable specific binding of a population of T-cells that recognize the HLA-myelin peptide complexes HLA-myelin-peptide complexes each including an antigen peptide and an HLA protein
a filter medium including an inert surface
a filter medium including a bead
a filter medium including sheet material
a filter medium including a fluid
a filter medium including polysulfone or polysulfone derivatives, glass matrices, silicon matrices, polydimethylsiloxane (PDMS), polycarbonate, polyetherimide (Ultem), or Tritan
a filter medium including a polyelectrolyte
HLA-myelin-peptide complexes disposed on a filter medium through covalent bonding, non-covalent interactions or adsorption
HLA-myelin-peptide complexes disposed on a medium through a maleimide analog
HLA-myelin-peptide complexes disposed on a medium through a maleimide analog
HLA-myelin-peptide complexes disposed on a filter medium in a manner such that anchoring locations for the complexes are spaced from each other by at least a width of an HLA binding groove
employing HLA proteins that are either HLA I and/or HLA II
hosting material including complexes of HLA proteins and antigen peptides derived from a non-myelin multiple sclerosis-associated protein
a first stage region being configured to retain a blood separator capable of separating white blood cells from other fractions of whole blood
a blood separator having an inlet, a white blood cell outlet, and a blood fraction outlet configured to enable return of the other fractions to the patient
a first pump for conveying blood from a patient through the first stage region
a second stage region configured to retain a biological filter including human leukocyte antigen (HLA)-peptide complexes
a second stage having at least one inlet and at least one outlet, and wherein the first stage region and the second stage region are oriented to enable flow from the white blood cell outlet of the blood separator to the at least one inlet of the biological filter a second pump for recirculating white blood cells from at least one outlet of a biological filter to at least one inlet of the biological filter a plurality of electrically controllable valves for directing blood through a first stage region and a second stage region at least one processor configured to control the first pump to cause blood to flow through the first stage region until a quantity of white blood cells are separated and conveyed to the second stage region deactivating a first pump when a quantity of white blood cells is separated and conveyed to a second stage region activating a second pump and control a plurality of valves to recirculate a quantity of white blood cells through a biological filter for a sufficient time to separate pathogenic T-cells from non-pathogenic white blood cells returning non-pathogenic white blood cells to a patient a plurality of electrically controllable valves includes at least one valve controllable by at least one processor to prevent white blood cells from being returned to a patient while a second pump is activated to recirculate a quantity of white blood cells through a biological filter of a second stage a plurality of electrically controllable valves includes at least one valve controllable by at least one processor to prevent white blood cells from traveling from a first stage region to a second stage region while a second pump is activated to recirculate a quantity of white blood cells through a biological filter of the second stage at least one processor is configured to control a plurality of electrically controllable valves to cause white blood cells to be processed in batches in a second stage region to permit a first batch of white blood cells to recirculate in the second stage region and thereafter be returned to the patient before the at least one processor permits a second batch of white blood cells to enter the biological filter of the second stage a blood separator configured to separate blood using apheresis a blood separator configured to separate blood using centrifugation a blood separator configured to separate blood using filtration wherein the blood separator configured to mechanically bind white blood cells to a cell-specific matrix a blood separator configured to permit binding of white blood cells to cell-specific antibodies a blood blending device, and wherein the at least one processor is configured to control the blood blending device to blend fractions of whole blood and/or the non-pathogenic white blood cells prior to returning to the patient a biological filter including a plurality of layers, each layer having human leukocyte antigen (HLA)-peptide complexes thereon a second stage region sized so that a biological filter may contain about 3-50 ml of a blood fraction collected wherein at least one of a first pump and a second pump is a peristaltic pump a blood storage chamber, wherein blood from a patient is stored in the blood storage chamber prior to separation in a blood separator an arterial blood pressure control unit at least one processor configured to control at least one valve to add erythrocytes and saline before returning other fractions of whole blood to a patient at least one processor configured to control at least one valve to supply anticoagulant to a stage region a biological filter configured to selectively bind pathogenic T-cells a tubing set for use in removing pathogenic T-cells from a patient's blood a tubing set including a first stage region having a blood separator for use in separating white blood cells from other fractions of whole blood and having an inlet, a white blood cell outlet, and a blood fraction outlet a tubing set having a second stage region including a biological filter containing human leukocyte antigen (HLA)-peptide complexes and having at least one primary inlet, at least one primary outlet, at least one recirculation inlet, and at least one recirculation outlet a tubing set having a recirculation loop interconnecting the at least one recirculation outlet with a recirculation inlet at least one blood withdrawal tube for conveying blood from a patient to the at least one inlet of the first stage region at least one intermediate tube for conveying blood from a white blood cell outlet of a first stage region to a primary inlet of a second stage region at least one first stage bypass tube for conveying a blood fraction from a blood fraction outlet of a first stage region for return to a patient at least one white cell return tube for conveying white blood cells from a primary outlet of a second stage region for return to a patient a primary inlet of a second stage region that is common with a recirculation inlet of a second stage region a primary outlet of a second stage region that is common with a recirculation outlet of the second stage region at least one processor configured to receive first data associated with treatment of a plurality of patients sharing a common HLA and common peptides triggering activation of disease-related T-cells, wherein the first data includes a progression of common peptides that activate the T-cells over time, in that at a later progression of a disease, a greater number of different peptides activates the disease-related T-cells than at an earlier time at least one processor configured to receive second data associated with a specific patient with the common HLA and the common peptides and who is at a stage of the disease where a first set of peptides activates a first subpopulation of the disease-related T-cells and a second set of peptides does not activate a second subpopulation of the disease-related T-cells at least one processor configured to determine using first data that the second set of peptides in the specific patient corresponds to the later progression of the disease at least one processor configured to aid in taking remedial action to remove a second subpopulation of disease-related T-cells from a specific patient before a second set of peptides activates the second subpopulation of the disease-related T-cells outputting an instruction to remove a second subpopulation of the disease-related T-cells from the specific patient outputting information for use in building a filter that includes a second set of peptides expected to trigger an adverse condition in the future analyzing information related to HLA typing and associated peptides stripping peptides from HLA complexes and determining peptide sequences HLA typing based on blood analysis and wherein information related to peptides is based on analysis of tissue-specific and disease-related biological fluid examining cerebrospinal fluid peptide data comparing disease-related parameters including years from onset, symptoms and treatment; HLA typing analysis; and analysis of peptides presented by corresponding HLA proteins a first set of peptides and a second set of peptides are variations of a same peptide a first set of peptides and a second set of peptides are different from each other at least one processor configured to identify additional sets of common peptides that do not activate the disease-related T-cells determining that additional sets of peptides correspond to a further progression of a disease removing additional subpopulations of disease-related T-cells from the patient before the additional sets of peptides activate the additional subpopulations of the disease-related T-cells outputting an instruction to remove the additional subpopulations of the disease-related T-cells outputting data for use in building a filter that includes the additional sets of peptides at least one processor configured to adjust treatment of the patient based on the identified additional sets of peptides adjusting treatment of a patient based on the identified second set of peptides removing a first subpopulation of the disease-related T-cells and the second subpopulation of the disease-related T-cells simultaneously removing a first subpopulation of disease-related T-cells, a second subpopulation of the disease-related T-cells and an additional subpopulation of the disease-related T-cells simultaneously treating multiple sclerosis focusing on peptides that are derived from myelin or a non-myelin CNS protein including an aquaporin channel focusing on peptides that are derived from myelin oligodendrocyte glycoprotein (MOG), myelin basic protein (MBP), myelin proteolipid protein (PLP), opalin protein, oligodendrocyte-specific protein (OSP), myelin-associated glycoprotein (MAG), or a combination thereof focusing on peptides that are derived from or are $MBP_{87-99}$, $MBP_{85-99}$, $MBP_{83-96}$, $MBP_{217-231}$, $MBP_{88-102}$, $MBP_{282-296}$, $PLP_{91-110}$, $PLP_{131-151}$, $PLP_{283-252}$, $PLP_{263-277}$, $PLP_{58-72}$, $PLP_{13-27}$, $OPALIN_{46-60}$, $OPALIN_{27-41}$, $OPALIN_{127-141}$, $MOG_{210-224}$, $MOG_{29-43}$, $MOG_{176-190}$, $MOG_{225-239}$, $OSP_{74-88}$, $OSP_{114-128}$, $MAG_{8-22}$, $MAG_{467-481}$, $MAG_{529-543}$, or a combination thereof drawing biological fluid from the patient, the biological fluid containing the specific cells extracorporeally flowing biological fluid through a medium hosting material that selectively binds to only the specific cells, to thereby trap the specific cells with the medium returning biological fluid, absent trapped specific cells, to a patient biologically filtering at least one of whole blood or a blood fraction biologically filtering cerebrospinal fluid biologically filtering bone marrow biologically filtering a synovial fluid biologically filtering a fluid obtained from an alveolar lavage biologically filtering a peritoneal fluid an inert surface includes polyethylene glycol (PEG) or PEG derivatives, polystyrene, avidin and/or streptavidin a biological filtering medium including at least one of polysulfone, polysulfone derivatives, a glass matrix, a silicon matrix, polydimethylsiloxane (PDMS), polycarbonate, polyetherimide (Ultem), or Tritan a biological filtering medium including polysulfone a biological filtering medium including a polyelectrolyte a biological filtering medium including at least one of sheet material, a liquid, mesh structures, fibers, gel, or beads a biological filtering medium including human leukocyte antigen (HLA)-peptide complexes, and wherein each HLA-peptide complex includes an HLA protein and a peptide a biological filtering medium including HLA proteins include HLA I and/or HLA II or a truncated form thereof a biological filtering medium including HLA engineered to include a cysteine residue at the C-terminus a biological filtering medium including HLA-peptide complexes disposed on the medium through a maleimide analog a biological filtering medium including an antibody a biological fluid is circulated through a biological filtering medium and returned to the patient using a peristaltic pump a biological filtering medium includes a fluid specific T-cells filtered biologically include at least one of CD4+ cells or CD8+ cells a biological filter configured to trap T-cells with T-cell receptors that are specific for antigen peptides derived from a protein associated with an autoimmune disease a biological filter configured to treat multiple sclerosis a biological filter configured to trap pathogenic cells associated with a cancerous disease including hematological cancers or solid cancers determining a human leukocyte antigen (HLA) type of the patient as part of constructing a biological filter identifying at least one immunogenic peptide associated with a disease of the patient recombinantly, synthetically, or endogenously producing HLA-peptide complexes corresponding to the determined HLA type of the patient and the at least one immunogenic peptide binding HLA-peptide complexes to an inert surface medium of a biological filter manufacturing HLA-peptide complexes including an HLA protein and an immunogenic peptide manufacturing HLA-peptide complexes including recombinantly produced HLA proteins and synthetically produced immunogenic peptides manufacturing HLA-peptide complexes include recombinantly produced HLA proteins and immunogenic peptides collecting HLA-peptide complexes obtained endogenously from a patient examining cerebrospinal fluid to identify an immunogenic peptide examining cerebrospinal fluid to identify a plurality of immunogenic peptides HLA typing determined through blood analysis and peptide identification determined through at least one of cerebrospinal fluid analysis or tissue-specific disease related peptide analysis a biological filter including at least one of sheet material, a liquid, mesh structures, fibers, a gel, or beads an inert surface medium including at least one of polysulfone, a polysulfone derivative, a glass matrix, a silicon matrix, polydimethylsiloxane (PDMS), polycarbonate, polyetherimide (Ultem), or Tritan an inert surface medium including at least one of polyethylene glycol (PEG), a PEG derivative, polystyrene, avidin or streptavidin an HLA-peptide complex covalently bound to an inert filter surface through a maleimide analog flowing blood from a patient over HLA-peptide complexes bound to an inert surface medium to thereby capture pathogenic cells using a biological filter to capture pathogenic cells associated with at least one of Leukemia, Acute Leukemia, cancer, Myasthenia gravis (MG), Lambert-Eaton myasthenic syndrome, Multiple Sclerosis (MS), Polycythemia Vera (PCV), Thrombocytosis, Scleroderma, type 1 diabetes, psoriasis, Crohn's disease, or Multiple Sclerosis further comprising, flowing blood from the patient over the HLA-peptide complexes bound to the inert surface medium to thereby capture pathogenic cells associated with at least one of myeloproliferative diseases or viral, bacterial, fungi, or parasitic infections wherein identifying the at least one immunogenic peptide includes comparing the peptide with a database of disease-related immunogenic peptides and their binding affinity for a corresponding HLA wherein the HLA type is HLA I and/or HLA II method comprising determining a human leukocyte antigen (HLA) type of a patient identifying at least one immunogenic peptide associated with a disease of the patient recombinantly or endogenously producing HLA proteins corresponding to a determined HLA type of a patient binding the HLA proteins to an inert surface medium synthesizing at least one identified peptide associated with a disease of a patient loading identified peptides on HLA proteins bound to an inert surface medium simultaneously loading and binding HLA proteins bound to an inert surface medium sequentially loading and binding HLA proteins bound to an inert surface medium determining specific disease-related peptides that together with a determined HLA, trigger T-cell receptor activation in the patient extracorporeally exposing blood of a patient to a filter treated with a complex constructed of the disease-related peptide loaded on the determined HLA, to thereby cause a binding of T-cells to the filter returning to a patient blood with bound T-cells removed exposing a filter with bound T-cells to a separation agent to remove the T-cells and counting the removed T-cells counted T-cells using flow cytometry including fluorescence activated cell sorting (FACS)

estimating disease progress based on a number of T-cells counted modifying treatment of a patient based on T-cell count Linking HLA-peptide complexes to a detectable label Linking HLA-peptide complexes to a label including at least one of a fluorophore, an enzyme, a radioisotope, a heavy metal, or a nuclear magnetic resonance marker administering an anticoagulant during biological filtering identifying at least one immunogenic peptide associated with a disease of the patient comparing an identified at least one immunogenic peptide with a database of disease-related immunogenic peptides and their binding affinity for the corresponding HLA type of a patient bound HLA proteins recombinantly produced to peptides synthetically produced bound HLA proteins and peptides recombinantly produced HLA proteins and peptides obtained endogenously from a patient and used to make a biological filter specific disease-related peptides incorporated into a biological filter are associated with an autoimmune disease, cancer, or any other disease involving an adaptive cellular immune response disease-related peptides incorporated into a biological filter are associated with multiple sclerosis HLA monomers or multimers in a biological filter HLA typing is determined through blood analysis biological filter designed to capture at least one of CD4+ cells or CD8+ cells performing biological filtering several times per year on a patient enriching blood with nutrients or a pharmaceutical composition before returning biologically filtered blood to a patient obtaining human leukocyte antigen (HLA)-peptide complex data for a particular patient having an autoimmune disorder triggered by first T-cells, and not triggered by second T-cells comparing the HLA-peptide complex data of a specific patient with HLA-peptide complex data associated with a population of patients having T-cell associated pathology, wherein the populational data includes epitope spreading information suggesting that persons with autoimmune disorders triggered by the first T-cells, will progress over time to be triggered by the second T-cells before an autoimmune disorder of a particular patient is triggered by second T-cells not currently triggering a disease, remove the second T-cells from the patient obtaining HLA-peptide complex data for a particular patient includes HLA typing and analyzing associated peptides HLA typing is determined through blood analysis and the peptide analysis is performed through at least one of cerebrospinal fluid analysis or tissue-specific disease related peptide analysis analyzing an associated peptide includes examining cerebrospinal fluid comparing the HLA-peptide complex data of the specific patient with HLA-peptide complex data associated with a population of patients having T-cell associated pathology includes a comparison of disease-related parameters including years from onset, symptoms and treatment; HLA typing analysis; and analysis of peptides presented by corresponding HLA proteins comparing HLA-peptide complex data of a specific patient with HLA-peptide complex data associated with a population of patients having T-cell associated pathology includes comparing patients that share mutual HLA types intermolecular or intramolecular epitope spreading identifying more than two T-cell groups that may trigger the autoimmune disorder over time, and removing them before they trigger disease before the autoimmune disorder of the particular patient is triggered by additional T-cell groups, remove T-cells of the additional T-cell groups from the particular patient adjusting treatment of a patient based on identified second T-cells removing second T-cells includes binding HLA-peptide complexes to T-cell receptors of the second T-cells wherein an autoimmune disease is multiple sclerosis and T-cells are activatable toward myelin or a non-myelin CNS protein including an aquaporin channel wherein the myelin includes at least one of myelin oligodendrocyte glycoprotein (MOG), myelin basic protein (MBP), myelin proteolipid protein (PLP), opalin protein, oligodendrocyte-specific protein (OSP), myelin-associated glycoprotein (MAG)

Removing more than one type of T-cells with a biological filter removing the first T-cells and the second T-cells simultaneously removing cells of an additional T-cell group includes binding HLA-peptide complexes to T-cell receptors of the cells of the additional T-cell group wherein the cells of an additional T-cell groups are removed by a biological filter removing first T-cells, second T-cells and cells of the additional T-cell groups simultaneously adjusting treatment of a patient based on identified additional T-cell groups predicted to cause damage in the future stripping native peptides from a first group of human leukocyte antigens (HLAs) in a first biological fluid sample determining at least one sequence of stripped native peptides comparing a determined at least one peptide sequence stripped from a patient, with historical information to identify at least one disease-specific peptide sequence among the native peptides loading onto a second group of HLAs, a plurality of peptides sharing the at least one disease-specific peptide sequence to form a plurality of HLA-peptide complexes bringing the plurality of HLA-peptide complexes into contact with a second biological fluid sample determining, for a plurality of HLA-peptide complexes brought into contact with a second biological fluid sample, a quantity of T-cells that bind to the plurality of HLA-peptide complexes based on the determined quantity of T-cells that bind to of the plurality of HLA-peptide complexes, estimating an amount of disease-specific pathogenic T-cells in a biological fluid volume within the patient measuring, estimating, or predicting a binding affinity of each of the plurality of HLA-peptide complexes for disease-specific pathogenic T-cells prior to determining the quantity of T-cells that bind to the plurality of HLA-peptide complexes validating that correct disease-specific pathogenic T-cells are bound to a plurality of HLA-peptide complexes assessing a status of a disease based on the determined quantity of T-cells that bind to the plurality of HLA-peptide complexes comparing a determined quantity of T-cells that bind to the plurality of HLA-peptide complexes with a quantity of T-cells determined from a population of patients having the disease assessing efficacy of a treatment regimen of a disease by comparing the determined quantity of T-cells that bind to the plurality of HLA-peptide complexes and a previously determined quantity of T-cells that bind to the plurality of HLA-peptide complexes adjusting a treatment regimen based on a comparison of a determined quantity of T-cells that bind to the plurality of HLA-peptide complexes and a previously determined quantity of T-cells that bind to the plurality of HLA-peptide complexes manufacturing a biological filter containing the plurality of HLA-peptide complexes manufacturing a biological filter includes synthesizing a plurality of peptides sharing the at least one disease-specific sequence manufacturing a biological filter further includes synthesizing HLAs, mixing the synthesized HLAs with the synthesized plurality of peptides sharing the at least one disease-specific sequence to form synthetic HLA-peptide complexes, and applying the synthesized HLA-peptide complexes to an inert surface medium Linking HLAs to a detectable marker a detectable marker includes at least one of a fluorophore, an enzyme, a radioisotope, a heavy metal, and a nuclear magnetic resonance marker a plurality of HLA-peptide complexes includes a plurality of synthetically or recombinantly produced peptides sharing the at least one disease-specific sequence HLA-peptide complexes include a plurality of synthetically or recombinantly produced peptides sharing the at least one disease-specific sequence or are obtained endogenously from a patient at least one sequence of stripped native peptides is determined using a mass spectrometer a quantity of T-cells that bind to the plurality of HLA-peptide complexes is determined using flow cytometry a quantity of T-cells that bind to the plurality of HLA-peptide complexes have a plurality of peptides sharing the at least one disease-specific peptide sequence a quantity of T-cells that bind to the plurality of HLA-peptide complexes include a plurality of peptides sharing a plurality of disease-specific peptide sequences wherein a patient has multiple sclerosis, and wherein at least one disease-specific peptide sequence is a sequence of a peptide derived from myelin associated protein wherein the patient has type 1 diabetes, and wherein the at least one disease-specific peptide sequence is a sequence of an insulin peptide or other protein associated with beta cell proteins wherein the patient has myasthenia gravis, and wherein the at least one disease-specific peptide sequence is a sequence of an acetylcholine receptor peptide wherein the patient has Crohn's disease, and wherein the at least one disease-specific peptide sequence is a sequence of a gastrointestinal tract peptide wherein the biological fluid is whole blood, a blood fraction, cerebrospinal fluid, synovial fluid, alveolar lavage fluid, peritoneal lavage, lymph, or bone marrow Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A biological filter for cytoreduction of multiple sclerosis-associated T-cells, the filter comprising:
   a filter medium having hosting material that selectively binds antigen-specific T-cell receptors disposed thereon; and
   wherein the hosting material includes human leukocyte antigen (HLA)-myelin-peptide complexes selected to bind with myelin-specific T-cell receptors, to thereby enable specific binding of a population of T-cells that recognize the HLA-myelin peptide complexes.

2. The filter of claim 1, wherein the HLA-myelin-peptide complexes each include an antigen peptide and an HLA protein.

3. The filter of claim 1, wherein the filter medium includes an inert surface.

4. The filter of claim 1, wherein the filter medium includes a bead.

5. The filter of claim 1, wherein the filter medium includes sheet material.

6. The filter of claim 1, wherein the filter medium includes a fluid.

7. The filter of claim 1, wherein the filter medium includes polysulfone or polysulfone derivatives, glass matrices, silicon matrices, polydimethylsiloxane (PDMS), polycarbonate, polyetherimide (Ultem), or a copolymer made from three monomers: dimethyl terephthalate (DMT), cyclohexanedimethanol (CHDM), and 2,2,4,4-tetramethyl-1,3-cyclobutanediol (CBDO).

8. The filter of claim 7, wherein the filter medium further includes a polyelectrolyte.

9. The filter of claim 1, wherein the HLA-myelin-peptide complexes are disposed on the filter medium through covalent bonding, non-covalent interactions or adsorption.

10. The filter of claim 1, wherein the HLA-myelin-peptide complexes are disposed on the medium through a maleimide analog.

11. The filter of claim 3, wherein the inert surface includes polyethylene glycol (PEG) or PEG derivatives, polystyrene, avidin or streptavidin.

12. The filter of claim 1, wherein the HLA-myelin-peptide complexes are disposed on the filter medium in a manner such that anchoring locations for the complexes are spaced from each other by at least a width of an HLA binding groove.

13. The filter of claim 1, wherein the HLA protein is truncated.

14. The filter of claim 1, wherein the HLA protein is further engineered to include a cysteine as the C-terminal residue.

15. The filter of claim 14, wherein the C-terminal cysteine is linked to the HLA protein through a peptide linker.

16. The filter of claim 1, wherein the HLA protein is HLA I and/or HLA II.

17. The filter of claim 1, wherein the HLA protein is HLA-typed to match a patient.

18. The filter of claim 1, wherein the myelin peptide is derived from myelin oligodendrocyte glycoprotein (MOG), myelin basic protein (MBP), or myelin proteolipid protein (PLP), opalin protein, oligodendrocyte-specific protein (OSP), myelin-associated glycoprotein (MAG), or a combination thereof.

19. The filter of claim 18, wherein the antigen is $MBP_{87-99}$, $MBP_{85-99}$, $MBP_{83-96}$, $MBP_{217-231}$, $MBP_{88-102}$, $MBP_{282-296}$, $PLP_{91-110}$, $PLP_{131-151}$, $PLP_{252-283}$, $PLP_{263-277}$, $PLP_{58-72}$, $PLP_{13-27}$, $OPALIN_{46-60}$, $OPALIN_{27-41}$, $OPALIN_{127-141}$, $MOG_{210-224}$, $MOG_{29-43}$, $MOG_{176-190}$, $MOG_{225-239}$, $OSP_{74-88}$, $OSP_{114-128}$, $MAG_{8-22}$, $MAG_{467-481}$, $MAG_{529-543}$, or a combination thereof.

20. The filter of claim 1, wherein the filter comprises a plurality of layers configured to permit fluid flow therebetween.

21. The filter of claim 1, wherein the hosting material further includes complexes of HLA proteins and antigen peptides derived from a non-myelin multiple sclerosis-associated protein.

* * * * *